United States Patent
Cybulski et al.

(10) Patent No.: US 12,035,889 B2
(45) Date of Patent: Jul. 16, 2024

(54) TISSUE MODIFICATION DEVICES AND METHODS OF USING THE SAME

(71) Applicant: InSyte Medical Technologies, Inc., King of Prussia, PA (US)

(72) Inventors: James S. Cybulski, Menlo Park, CA (US); Fred R. Seddiqui, Los Altos, CA (US)

(73) Assignee: Trice Medical, Inc., Malvern, PA (US)

( * ) Notice: Subject to any disclaimer, the term of this patent is extended or adjusted under 35 U.S.C. 154(b) by 1750 days.

(21) Appl. No.: 16/000,731

(22) Filed: Jun. 5, 2018

(65) Prior Publication Data
US 2018/0317752 A1    Nov. 8, 2018

Related U.S. Application Data

(63) Continuation of application No. 13/055,662, filed as application No. PCT/US2009/051446 on Jul. 22, (Continued)

(51) Int. Cl.
*A61B 1/012*    (2006.01)
*A61B 1/00*    (2006.01)
(Continued)

(52) U.S. Cl.
CPC .......... *A61B 1/012* (2013.01); *A61B 1/00071* (2013.01); *A61B 1/00087* (2013.01);
(Continued)

(58) Field of Classification Search
CPC .......... A61B 2017/00398; A61B 2017/00017; A61B 2017/2927; A61B 2017/07285;
(Continued)

(56) References Cited

U.S. PATENT DOCUMENTS

| 3,871,358 A | 3/1975 | Fukuda et al. |
| 4,519,391 A | 5/1985 | Murakoshi |

(Continued)

FOREIGN PATENT DOCUMENTS

| AU | 2015204444 | 1/2018 |
| CN | 2557085 Y | 6/2003 |

(Continued)

OTHER PUBLICATIONS

Keller C.A., Hinerman, R., Singh, A., Alvarez, F., "The Use of Endoscopic Argon Plasma Coagulation in Airway Complications After Solid Organ Transplantation," Chest, 2001, vol. 119, No. 6, pp. 1968-1975.

*Primary Examiner* — Khadijeh A Vahdat
*Assistant Examiner* — Marina Delaney Templeton
(74) *Attorney, Agent, or Firm* — Knobbe, Martens, Olson & Bear LLP

(57) ABSTRACT

Tissue modification devices are provided. Aspects of the devices include an elongated member having a proximal end and a distal end. The distal end of the elongated member is dimensioned to pass through a minimally invasive body opening and includes a distal end integrated visualization sensor and tissue modifier. In some instances, the devices further include an integrated articulation mechanism that imparts steerabilily to at least one of the visualization sensor, the tissue modifier and the distal end of the elongated member. Also provided are methods of modifying internal target tissue of a subject using the tissue modification devices.

19 Claims, 29 Drawing Sheets

Related U.S. Application Data 2009, now abandoned, which is a continuation of application No. 12/422,176, filed on Apr. 10, 2009, now abandoned.

(60) Provisional application No. 61/082,774, filed on Jul. 22, 2008.

(51) Int. Cl.
| | |
|---|---|
| *A61B 1/015* | (2006.01) |
| *A61B 1/05* | (2006.01) |
| *A61B 1/06* | (2006.01) |
| *A61B 1/07* | (2006.01) |
| *A61B 1/313* | (2006.01) |
| *A61B 1/317* | (2006.01) |
| *A61B 17/00* | (2006.01) |
| *A61B 17/32* | (2006.01) |
| *A61B 18/00* | (2006.01) |
| *A61B 18/14* | (2006.01) |
| *A61B 90/00* | (2016.01) |
| *A61B 90/30* | (2016.01) |

(52) U.S. Cl.
CPC ...... *A61B 1/00091* (2013.01); *A61B 1/00114* (2013.01); *A61B 1/00167* (2013.01); *A61B 1/00183* (2013.01); *A61B 1/05* (2013.01); *A61B 1/051* (2013.01); *A61B 1/0676* (2013.01); *A61B 1/0684* (2013.01); *A61B 1/3135* (2013.01); *A61B 1/317* (2013.01); *A61B 18/1485* (2013.01); *A61B 1/015* (2013.01); *A61B 1/07* (2013.01); *A61B 2017/00261* (2013.01); *A61B 2017/320069* (2017.08); *A61B 2017/32007* (2017.08); *A61B 2017/320071* (2017.08); *A61B 2018/00982* (2013.01); *A61B 2018/1407* (2013.01); *A61B 2090/306* (2016.02); *A61B 90/361* (2016.02); *A61B 2218/002* (2013.01); *A61B 2218/007* (2013.01)

(58) Field of Classification Search
CPC ........... A61B 2017/00473; A61B 2017/00367; A61B 2017/00075; A61B 2017/320032; A61B 2017/00261; A61B 2017/320016; A61B 2017/32002; A61B 2017/320028; A61B 2017/32004; A61B 2017/320024; A61B 2017/320082; A61B 2017/320072; A61B 2017/320074; A61B 2017/320077; A61B 2017/320093; A61B 2017/22075; A61B 2090/0811; A61B 2018/00577; A61B 2018/00601; A61B 2018/1253; A61B 2018/00994; A61B 2018/1475; A61B 2018/00184; A61B 2018/00196; A61B 2018/00208; A61B 34/76; A61B 34/71; A61B 18/14; A61B 18/082; A61B 17/32002; A61M 2205/106

See application file for complete search history.

(56) References Cited

U.S. PATENT DOCUMENTS

| | | | |
|---|---|---|---|
| 4,624,243 A | 11/1986 | Lowery et al. | |
| 4,651,201 A | 3/1987 | Schoolman | |
| 4,674,498 A * | 6/1987 | Stasz ................. | A61B 18/1402 606/48 |
| 4,697,210 A | 9/1987 | Toyota et al. | |
| 4,845,555 A | 7/1989 | Yabe et al. | |
| 4,903,696 A * | 2/1990 | Stasz ................. | A61B 18/1206 606/39 |
| 4,919,112 A | 4/1990 | Siegmund | |
| 5,088,676 A | 2/1992 | Orchard et al. | |
| 5,170,775 A | 12/1992 | Tagami | |
| 5,178,130 A | 1/1993 | Kaiya | |
| 5,188,093 A | 2/1993 | Lafferty et al. | |
| 5,190,028 A | 3/1993 | Lafferty et al. | |
| 5,228,430 A | 7/1993 | Sakamoto | |
| 5,291,010 A | 3/1994 | Tsuji | |
| 5,312,407 A | 5/1994 | Carter | |
| 5,373,312 A | 6/1994 | Bala | |
| 5,351,678 A | 10/1994 | Clayton et al. | |
| 5,354,302 A | 10/1994 | Ko | |
| 5,365,267 A | 11/1994 | Edwards | |
| 5,368,015 A | 11/1994 | Wilk | |
| 5,369,525 A | 11/1994 | Bala et al. | |
| 5,373,317 A | 12/1994 | Salvati et al. | |
| 5,373,392 A | 12/1994 | Bala | |
| 5,395,312 A | 3/1995 | Desai | |
| 5,406,940 A | 4/1995 | Melzer et al. | |
| 5,423,312 A | 6/1995 | Siegmund et al. | |
| 5,494,483 A | 2/1996 | Adair | |
| 5,512,036 A | 4/1996 | Tamburrino et al. | |
| 5,547,455 A | 8/1996 | McKenna et al. | |
| 5,569,158 A | 10/1996 | Suzuki et al. | |
| 5,577,992 A | 11/1996 | Chiba et al. | |
| 5,582,575 A | 12/1996 | Heckele et al. | |
| 5,601,525 A | 2/1997 | Okada | |
| 5,630,784 A | 5/1997 | Siegmund et al. | |
| 5,735,792 A | 4/1998 | Vanden Hoeck et al. | |
| 5,757,458 A | 5/1998 | Miller et al. | |
| 5,818,527 A | 10/1998 | Yamaguchi et al. | |
| 5,836,943 A | 11/1998 | Miller | |
| 5,864,359 A | 1/1999 | Kazakevich | |
| 5,868,664 A | 2/1999 | Speier et al. | |
| 5,873,816 A | 2/1999 | Kagawa et al. | |
| 5,873,817 A | 2/1999 | Adair | |
| 5,879,285 A | 3/1999 | Ishii | |
| 5,888,193 A | 3/1999 | Breidental et al. | |
| 5,928,137 A | 7/1999 | Green | |
| 5,929,901 A | 7/1999 | Adair et al. | |
| 5,941,817 A | 8/1999 | Crawford | |
| 5,976,076 A | 11/1999 | Kolff et al. | |
| 5,986,693 A | 11/1999 | Adair et al. | |
| 6,001,084 A | 12/1999 | Riek et al. | |
| 6,043,839 A | 3/2000 | Adair et al. | |
| 6,068,603 A | 5/2000 | Suzuki | |
| 6,080,101 A | 6/2000 | Tatsuno et al. | |
| 6,099,465 A | 8/2000 | Inoue | |
| 6,126,592 A | 10/2000 | Proch et al. | |
| 6,129,662 A | 10/2000 | Li et al. | |
| 6,211,904 B1 | 4/2001 | Adair et al. | |
| 6,234,955 B1 | 5/2001 | Silverman et al. | |
| 6,261,226 B1 | 7/2001 | McKenna et al. | |
| 6,275,255 B1 | 8/2001 | Adair et al. | |
| 6,310,642 B1 | 10/2001 | Adair et al. | |
| 6,315,712 B1 | 11/2001 | Rovegno | |
| 6,316,215 B1 | 11/2001 | Adair et al. | |
| 6,322,494 B1 | 11/2001 | Bullivant et al. | |
| 6,371,909 B1 | 4/2002 | Hoeg et al. | |
| 6,387,043 B1 | 5/2002 | Yoon | |
| 6,390,972 B1 | 5/2002 | Speier et al. | |
| 6,419,627 B1 | 7/2002 | Ben Nun | |
| 6,419,654 B1 | 7/2002 | Kadan | |
| 6,424,369 B1 | 7/2002 | Adair et al. | |
| 6,447,445 B1 | 9/2002 | Hirano | |
| 6,452,626 B1 | 9/2002 | Adair et al. | |
| 6,458,140 B2 | 10/2002 | Akin et al. | |
| 6,459,481 B1 | 10/2002 | Schaack | |
| 6,464,633 B1 | 10/2002 | Hosoda et al. | |
| 6,468,274 B1 | 10/2002 | Alleyne et al. | |
| 6,478,730 B1 | 11/2002 | Bala et al. | |
| 6,517,498 B1 * | 2/2003 | Burbank ......... | A61B 17/32056 606/45 |
| 6,527,753 B2 | 3/2003 | Sekine et al. | |
| 6,561,973 B1 | 5/2003 | Bala | |
| 6,675,033 B1 | 1/2004 | Lardo et al. | |
| 6,679,838 B2 | 1/2004 | Bala | |
| 6,692,432 B1 | 2/2004 | Yarush et al. | |
| 6,695,772 B1 | 2/2004 | Bon et al. | |

(56) References Cited

U.S. PATENT DOCUMENTS

| | | |
|---|---|---|
| 6,750,037 B2 | 6/2004 | Adair et al. |
| 6,764,439 B2 | 7/2004 | Schaaf et al. |
| 6,832,984 B2 | 12/2004 | Stelzer et al. |
| 6,862,036 B2 | 3/2005 | Adair et al. |
| 6,863,651 B2 | 3/2005 | Remijan et al. |
| 6,885,801 B1 | 3/2005 | Shankar et al. |
| 6,982,740 B2 | 1/2006 | Adair et al. |
| 6,982,742 B2 | 1/2006 | Adair et al. |
| 7,002,621 B2 | 2/2006 | Adair et al. |
| 7,030,904 B2 | 4/2006 | Adair et al. |
| 7,060,028 B2 | 6/2006 | Luloh et al. |
| 7,108,657 B2 | 9/2006 | Irion et al. |
| 7,156,559 B2 | 1/2007 | Gauthier, Jr. et al. |
| 7,160,247 B2 | 1/2007 | Deppmeier et al. |
| 7,214,183 B2 | 5/2007 | Miyake |
| 7,269,344 B2 | 9/2007 | Nishioka et al. |
| 7,435,010 B2 | 10/2008 | Gauthier, Jr. et al. |
| 7,453,984 B2 | 11/2008 | Chen et al. |
| 7,491,168 B2 | 2/2009 | Raymond et al. |
| 7,572,578 B2 | 2/2009 | Blanchard |
| 7,689,268 B2 | 3/2010 | Marshik-Geurts et al. |
| 7,699,773 B2 | 4/2010 | Forkey et al. |
| 7,708,689 B2 | 5/2010 | Deppmeier et al. |
| 7,857,755 B2 | 12/2010 | Kupferschmid et al. |
| 7,918,787 B2 | 4/2011 | Saadat |
| 7,942,814 B2 | 5/2011 | Remijan et al. |
| 8,016,839 B2 | 9/2011 | Wilk |
| 8,038,602 B2 | 10/2011 | Gill et al. |
| 8,046,057 B2 | 10/2011 | Clarke |
| 8,052,609 B2 | 11/2011 | Harhen |
| 8,142,346 B2 | 3/2012 | Shoroji et al. |
| 8,170,319 B2 | 5/2012 | Shukla |
| 8,277,411 B2 | 10/2012 | Gellman |
| 8,317,689 B1 | 11/2012 | Remijan et al. |
| 8,475,361 B2 | 7/2013 | Barlow et al. |
| 8,885,034 B2 | 11/2014 | Adair et al. |
| 2001/0036015 A1 | 11/2001 | Eguchi |
| 2001/0053873 A1 | 12/2001 | Schaaf et al. |
| 2002/0007110 A1 | 1/2002 | Irion |
| 2002/0087047 A1 | 7/2002 | Remijan et al. |
| 2002/0111564 A1* | 8/2002 | Burbank ............ A61B 10/0233 606/45 |
| 2002/0120261 A1* | 8/2002 | Morris ............... A61M 25/1002 606/41 |
| 2002/0177847 A1 | 11/2002 | Long |
| 2003/0040668 A1 | 2/2003 | Kaneko et al. |
| 2003/0120156 A1 | 6/2003 | Forrester et al. |
| 2003/0181905 A1 | 9/2003 | Long |
| 2003/0220574 A1 | 11/2003 | Markus et al. |
| 2003/0233024 A1 | 12/2003 | Ando |
| 2004/0102772 A1 | 5/2004 | Baxter et al. |
| 2004/0162554 A1* | 8/2004 | Lee ........................ A61B 18/14 606/45 |
| 2004/0162572 A1 | 8/2004 | Sauer |
| 2004/0215061 A1 | 10/2004 | Kimmel et al. |
| 2005/0038317 A1 | 2/2005 | Ratnakar |
| 2005/0113641 A1 | 5/2005 | Bala |
| 2005/0154262 A1 | 7/2005 | Banik et al. |
| 2005/0197536 A1 | 9/2005 | Banik et al. |
| 2005/0197658 A1 | 9/2005 | Platt |
| 2005/0213267 A1 | 9/2005 | Azrai et al. |
| 2005/0234296 A1 | 10/2005 | Saadat et al. |
| 2005/0277808 A1 | 12/2005 | Sonnenschein et al. |
| 2006/0004258 A1 | 1/2006 | Sun et al. |
| 2006/0004354 A1 | 1/2006 | Suslov |
| 2006/0030861 A1 | 2/2006 | Simonson et al. |
| 2006/0063973 A1 | 3/2006 | Makower et al. |
| 2006/0069313 A1 | 3/2006 | Couvillon et al. |
| 2006/0089633 A1 | 4/2006 | L. Bleich et al. |
| 2006/0106282 A1 | 5/2006 | Bala |
| 2006/0111613 A1 | 5/2006 | Boutillette et al. |
| 2006/0149129 A1 | 7/2006 | Watts et al. |
| 2006/0206007 A1 | 9/2006 | Bala |
| 2006/0206118 A1 | 9/2006 | Kim et al. |
| 2006/0241648 A1 | 10/2006 | Bleich et al. |
| 2006/0258951 A1 | 11/2006 | Bleich et al. |
| 2006/0276690 A1 | 12/2006 | Farris, III et al. |
| 2006/0281972 A1 | 12/2006 | Pease et al. |
| 2006/0293562 A1 | 12/2006 | Uchimura et al. |
| 2007/0038117 A1 | 2/2007 | Bala |
| 2007/0049794 A1 | 3/2007 | Glassenberg et al. |
| 2007/0073109 A1 | 3/2007 | Irion |
| 2007/0075654 A1 | 4/2007 | Kishinevsky |
| 2007/0093689 A1 | 4/2007 | Steinberg |
| 2007/0123888 A1 | 5/2007 | Bleich et al. |
| 2007/0129604 A1 | 6/2007 | Hatcher et al. |
| 2007/0129719 A1 | 6/2007 | Kendale et al. |
| 2007/0135874 A1 | 6/2007 | Bala |
| 2007/0161855 A1 | 7/2007 | Mikkaichi et al. |
| 2007/0167678 A1 | 7/2007 | Moskowitz et al. |
| 2007/0167681 A1 | 7/2007 | Gill et al. |
| 2007/0179340 A1 | 8/2007 | Jorgensen |
| 2007/0213734 A1 | 9/2007 | Bleich et al. |
| 2007/0213735 A1 | 9/2007 | Bleich et al. |
| 2007/0219412 A1 | 9/2007 | DiGiovanni et al. |
| 2007/0225556 A1 | 9/2007 | Ortiz et al. |
| 2007/0249904 A1 | 10/2007 | Amano et al. |
| 2007/0287886 A1 | 12/2007 | Saadat |
| 2008/0009747 A1 | 1/2008 | Saadat et al. |
| 2008/0009860 A1* | 1/2008 | Odom ................. A61B 18/1445 606/51 |
| 2008/0033465 A1 | 2/2008 | Schmitz et al. |
| 2008/0051629 A1 | 2/2008 | Sugiyama et al. |
| 2008/0051812 A1 | 2/2008 | Schmitz et al. |
| 2008/0062429 A1 | 3/2008 | Liang et al. |
| 2008/0064925 A1 | 3/2008 | Gill et al. |
| 2008/0103504 A1 | 5/2008 | Schmitz et al. |
| 2008/0108869 A1 | 5/2008 | Sanders et al. |
| 2008/0147018 A1 | 6/2008 | Squilla et al. |
| 2008/0200758 A1 | 8/2008 | Orbay et al. |
| 2008/0207992 A1 | 8/2008 | Scheller et al. |
| 2008/0214896 A1 | 9/2008 | Krupa et al. |
| 2008/0262302 A1 | 10/2008 | Azarbarzin et al. |
| 2008/0287961 A1 | 11/2008 | Miyamoto et al. |
| 2008/0300462 A1 | 12/2008 | Intoccia et al. |
| 2009/0043165 A1 | 2/2009 | Kucklick et al. |
| 2009/0076329 A1 | 3/2009 | Su et al. |
| 2009/0253967 A1 | 10/2009 | Gill et al. |
| 2009/0264706 A1 | 10/2009 | Bala |
| 2010/0022824 A1 | 1/2010 | Cybulski et al. |
| 2010/0056862 A1 | 3/2010 | Bakos |
| 2010/0063352 A1 | 3/2010 | Matsuura |
| 2010/0063356 A1 | 3/2010 | Smith |
| 2010/0087798 A1 | 4/2010 | Adams et al. |
| 2010/0094231 A1 | 4/2010 | Bleich et al. |
| 2010/0121139 A1 | 5/2010 | OuYang et al. |
| 2010/0121155 A1 | 5/2010 | OuYang et al. |
| 2010/0165335 A1 | 7/2010 | Tearney |
| 2010/0165336 A1 | 7/2010 | Terney |
| 2010/0217080 A1 | 8/2010 | Cheung et al. |
| 2010/0256446 A1 | 10/2010 | Raju |
| 2010/0274081 A1 | 10/2010 | Okoniewski |
| 2010/0284580 A1 | 11/2010 | OuYang et al. |
| 2010/0286477 A1 | 11/2010 | OuYang et al. |
| 2011/0034769 A1 | 2/2011 | Adair et al. |
| 2011/0227509 A1 | 9/2011 | Saleh |
| 2011/0263933 A1 | 10/2011 | Schaaf |
| 2011/0276113 A1 | 11/2011 | Cybulski |
| 2012/0071721 A1 | 3/2012 | Remijan et al. |
| 2012/0088968 A1 | 4/2012 | Gambhir et al. |
| 2012/0095458 A1 | 4/2012 | Cybulski et al. |
| 2012/0265009 A1 | 10/2012 | OuYang et al. |
| 2013/0046142 A1 | 2/2013 | Remijan et al. |
| 2013/0144122 A1 | 6/2013 | Adair et al. |
| 2013/0296648 A1 | 11/2013 | OuYang et al. |
| 2013/0303846 A1 | 11/2013 | Cybulski et al. |
| 2015/0112324 A1 | 4/2015 | Cybulski |
| 2015/0157387 A1 | 6/2015 | OuYang et al. |
| 2015/0196193 A1 | 7/2015 | Kienzle et al. |
| 2015/0196197 A1 | 7/2015 | Kienzle et al. |
| 2015/0313634 A1 | 11/2015 | Gross et al. |
| 2016/0045224 A1 | 2/2016 | Hendershot, III |
| 2016/0296108 A1 | 10/2016 | Kienzle et al. |
| 2017/0042408 A1 | 2/2017 | Washburn et al. |

(56) References Cited

U.S. PATENT DOCUMENTS

| | | |
|---|---|---|
| 2017/0042573 A1 | 2/2017 | Savvouras et al. |
| 2017/0086666 A1 | 3/2017 | Kienzle et al. |
| 2017/0265879 A1 | 9/2017 | Washburn et al. |

FOREIGN PATENT DOCUMENTS

| | | |
|---|---|---|
| CN | 1612708 A | 5/2005 |
| CN | 1779836 A | 5/2006 |
| CN | 101040775 A | 9/2007 |
| CN | 103961177 A | 8/2014 |
| CN | 104367296 A | 2/2015 |
| CN | 106455907 A | 2/2017 |
| EP | 1252859 A2 | 10/2002 |
| EP | 2317931 A2 | 5/2011 |
| EP | 2335550 A2 | 6/2011 |
| EP | 2451338 A2 | 5/2012 |
| EP | 3094231 | 11/2016 |
| GB | 2431539 A | 4/2007 |
| JP | H1033462 A | 2/1998 |
| JP | 2001-161630 | 6/2001 |
| WO | WO 2000/09001 | 2/2000 |
| WO | WO 2006/107877 | 10/2006 |
| WO | WO 2007/106740 | 9/2007 |
| WO | WO 2008/016927 | 2/2008 |
| WO | WO 2008/098251 | 8/2008 |
| WO | WO 2010/011781 | 1/2010 |
| WO | WO 2011/006052 | 1/2011 |
| WO | WO 2014/137530 | 9/2014 |
| WO | WO 2015/106288 | 7/2015 |
| WO | WO 2016/130844 | 8/2016 |
| WO | WO 2017/027749 | 2/2017 |
| WO | WO 2017/161777 | 9/2017 |

* cited by examiner

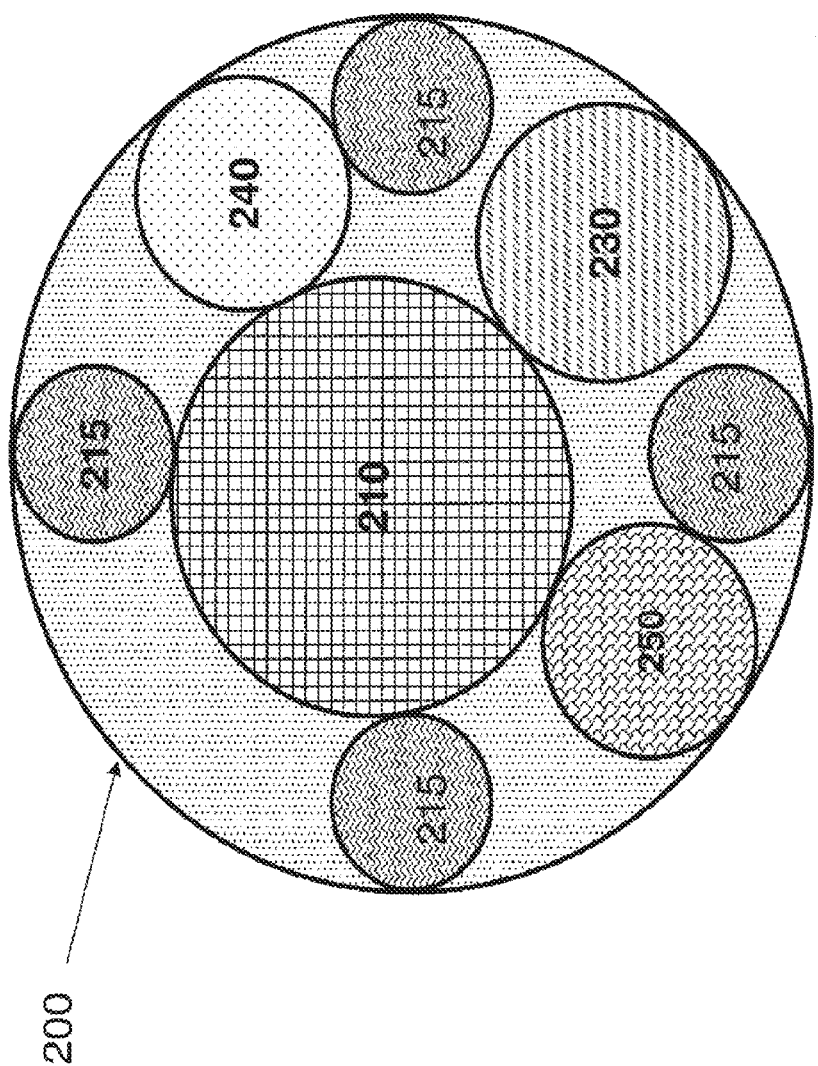

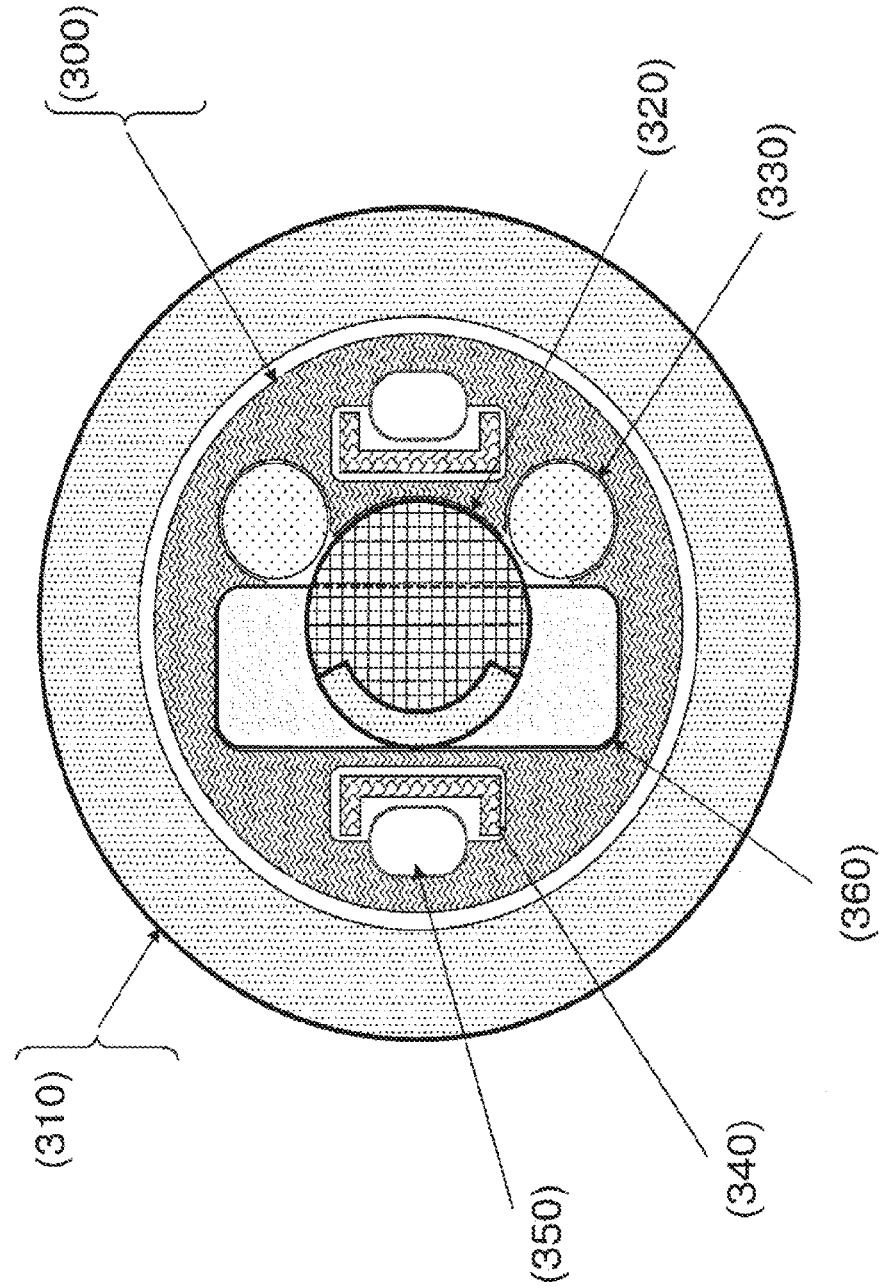

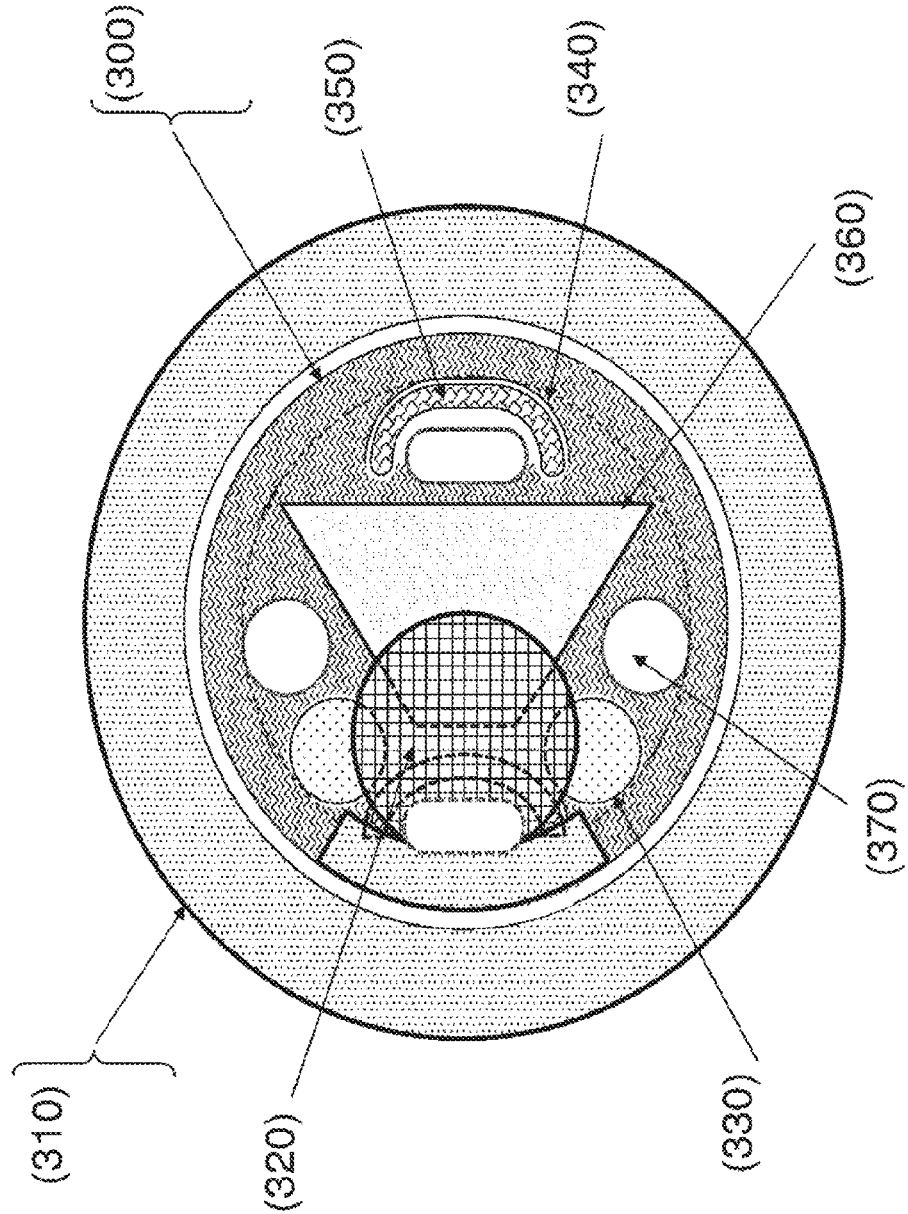

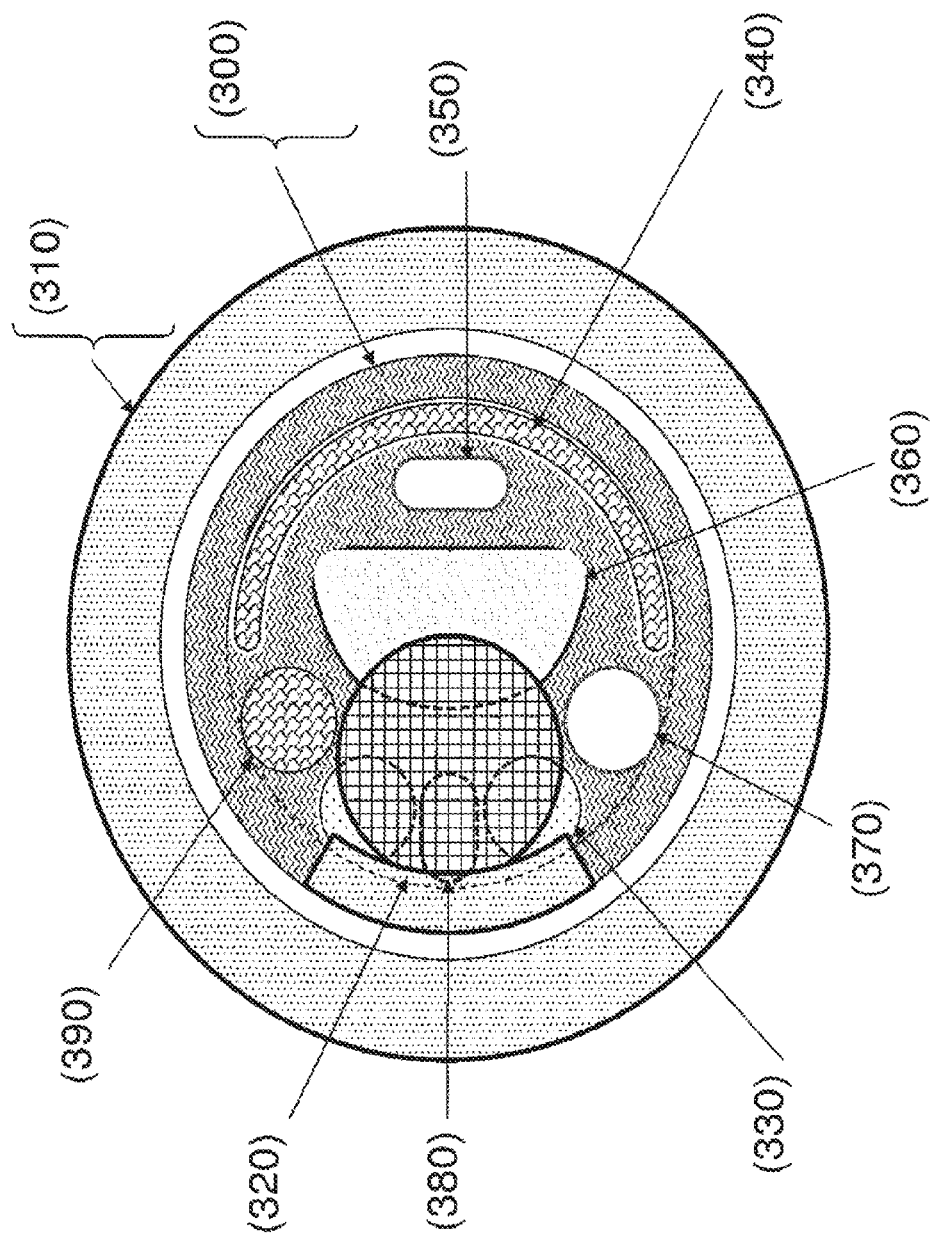

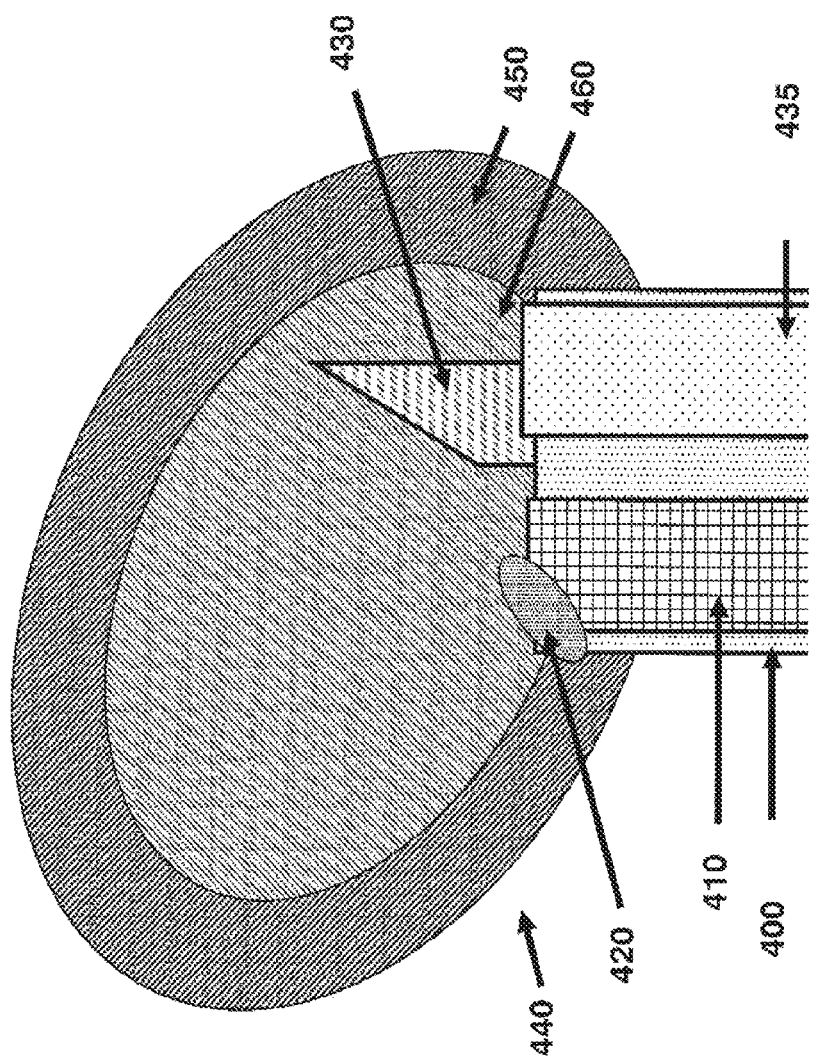

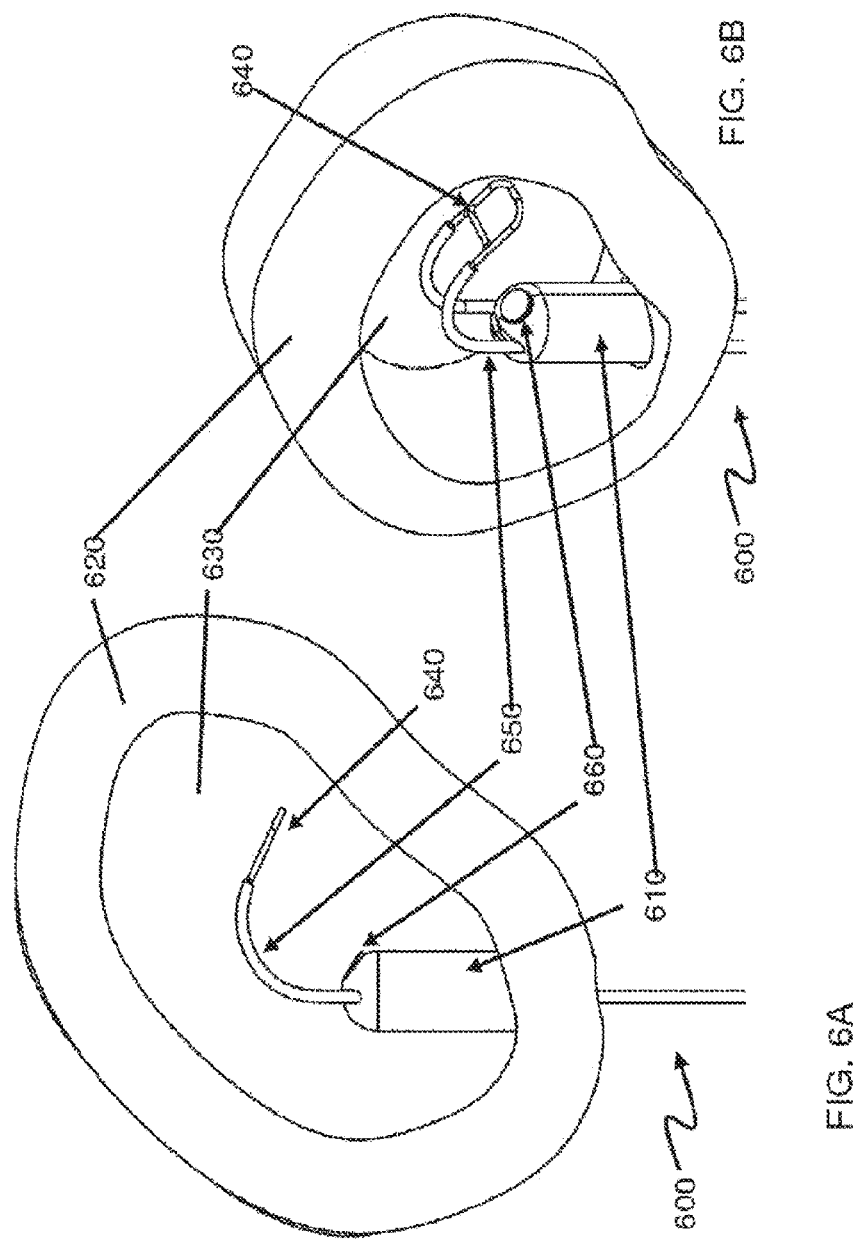

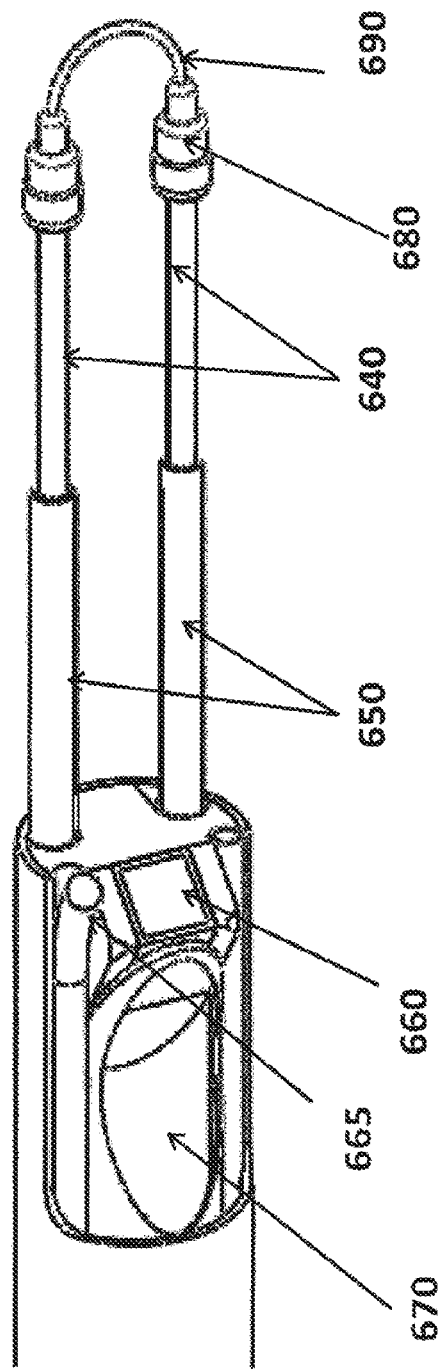

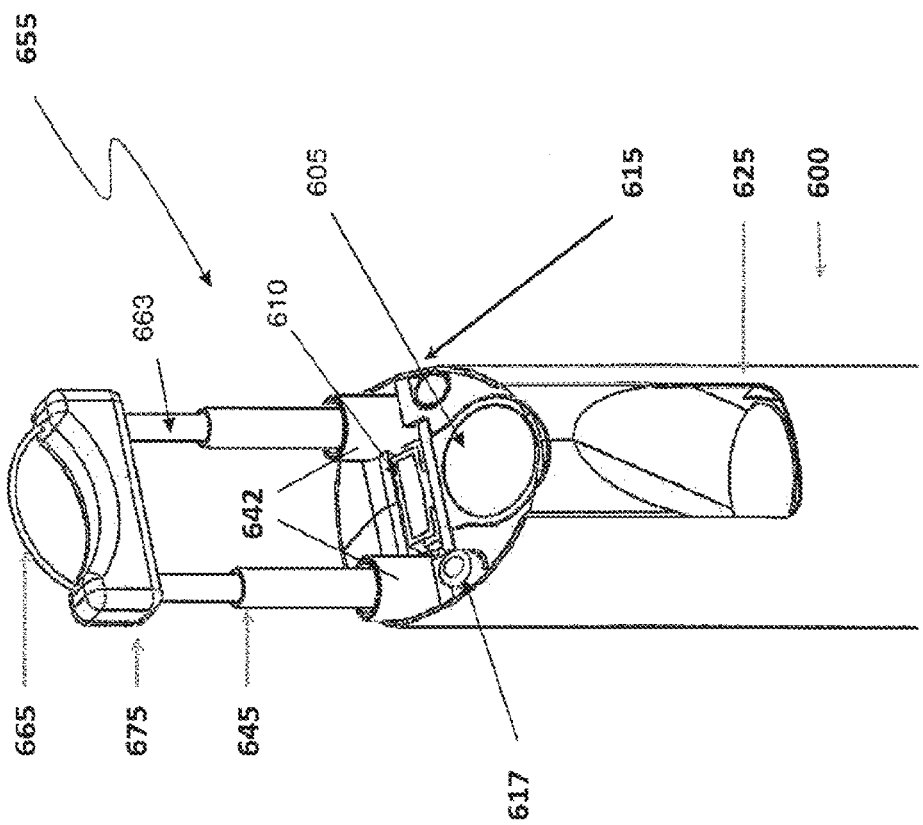

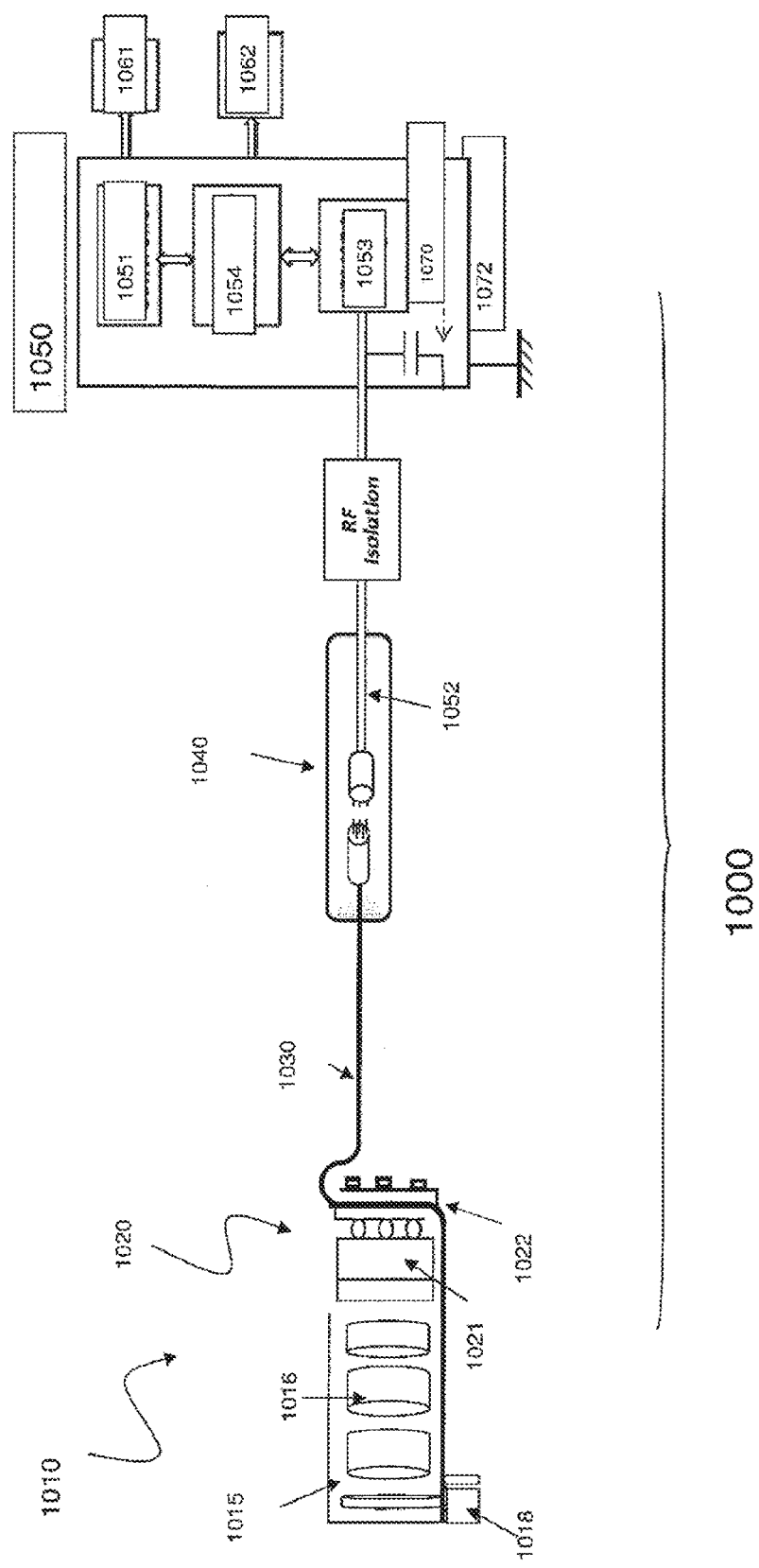

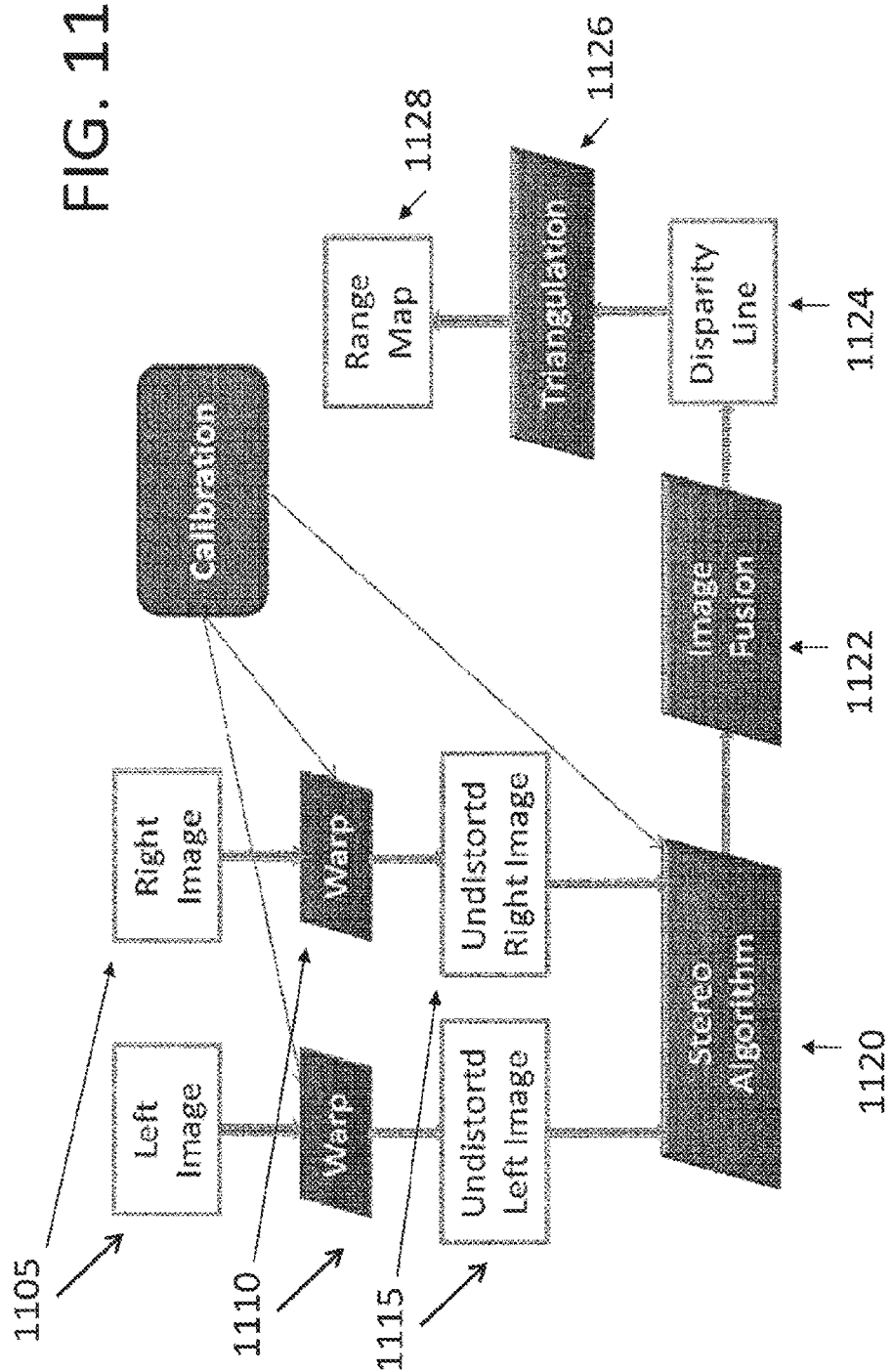

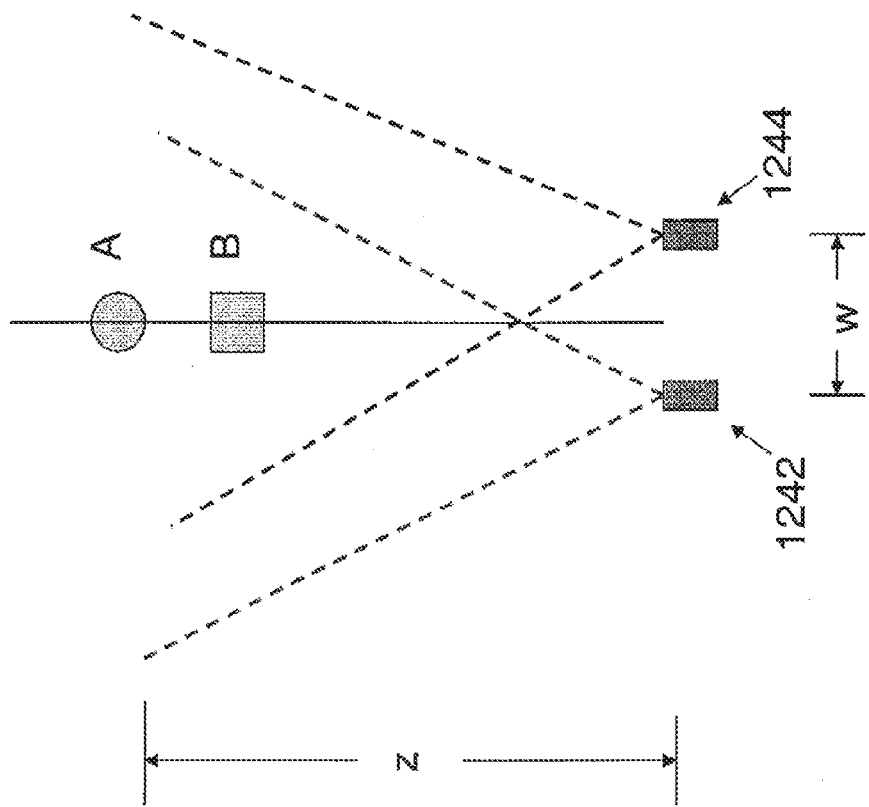
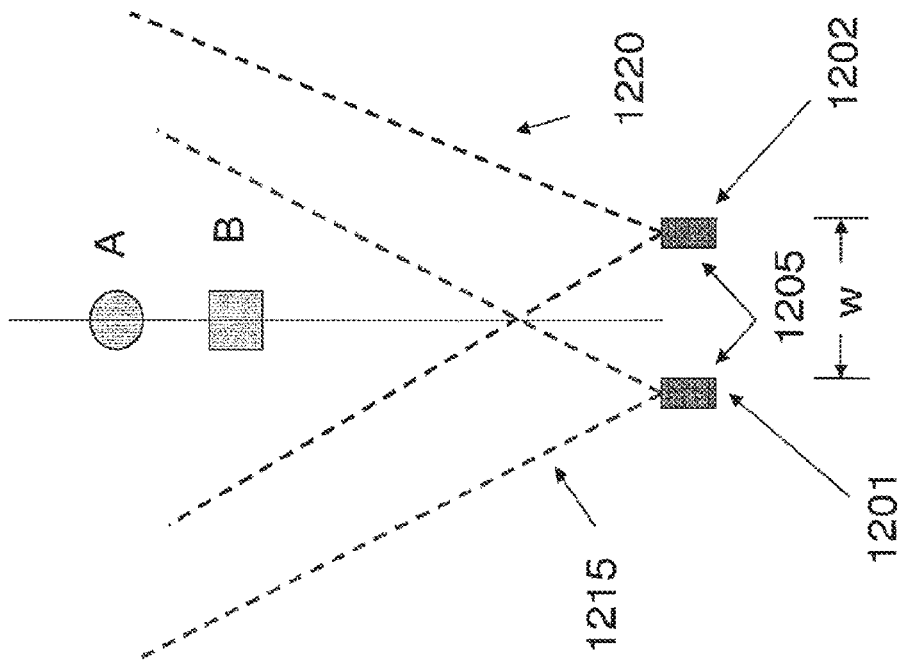
FIG. 12A
FIG. 12B

TISSUE MODIFICATION DEVICES AND METHODS OF USING THE SAME

CROSS-REFERENCE TO RELATED APPLICATIONS

The present application is a continuation of U.S. application Ser. No. 13/055,662 filed on Nov. 18, 2011, entitled TISSUE MODIFICATION DEVICES AND METHODS OF USING THE SAME, which is a United States National Phase Application under 35 U.S.C. § 371 of International Application No. PCT/US2009/051446, filed on Jul. 22, 2009, entitled TISSUE MODIFICATION DEVICES AND METHODS OF USING THE SAME, which claims priority to U.S. application Ser. No. 12/422,176 filed on Apr. 10, 2009, entitled TISSUE MODIFICATION DEVICES AND METHODS OF USING THE SAME, which claims the benefit to U.S. Provisional Application No. 61/082,774 filed Jul. 22, 2008, entitled ULTRA-SLIM STEERABLE ENDOSCOPE FOR TISSUE DISSECTION WITH VISUALIZATION. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

INTRODUCTION

Traditional surgical procedures, both therapeutic and diagnostic, for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

SUMMARY

Tissue modification devices are provided. Aspects of the devices include an elongated member having a proximal end and a distal end. The distal end of the elongated member is dimensioned to pass through a minimally invasive body opening and includes a distal end integrated visualization sensor and tissue modifier. In some instances, the devices further include an integrated articulation mechanism that imparts steerability to at least one of the visualization sensor, the tissue modifier and the distal end of the elongated member. Also provided are methods of modifying internal target tissue of a subject using the tissue modification devices.

BRIEF DESCRIPTION OF THE FIGURES

FIGS. 2A to 2C provide cross-sectional views of the distal ends of devices according to certain embodiments of the invention.

FIGS. 3A to 3E provide cross-sectional views of the distal ends of devices according to certain embodiments of the invention.

FIG. 4 provides an alternative view of the distal end of a device according to an embodiment of the invention, where the device is shown accessing the nucleus pulposus of an intervertebral disc.

FIGS. 6A to 6E provide various views of the distal end of a device according to one embodiment of the invention.

FIG. 10 shows a CMOS visualization sub-system that may be incorporated into a tissue modification system according to an embodiment of the invention.

FIG. 11 provides a block flow diagram of a stereoscopic image module, according to one embodiment.

FIG. 12A provides a single visualization sensor which is moved between two different positions to sequentially obtain image data, according to an embodiment. FIG. 12B provides slightly offset visualization positions of two different visualization sensors, according to an embodiment.

DETAILED DESCRIPTION

Figure 1A:
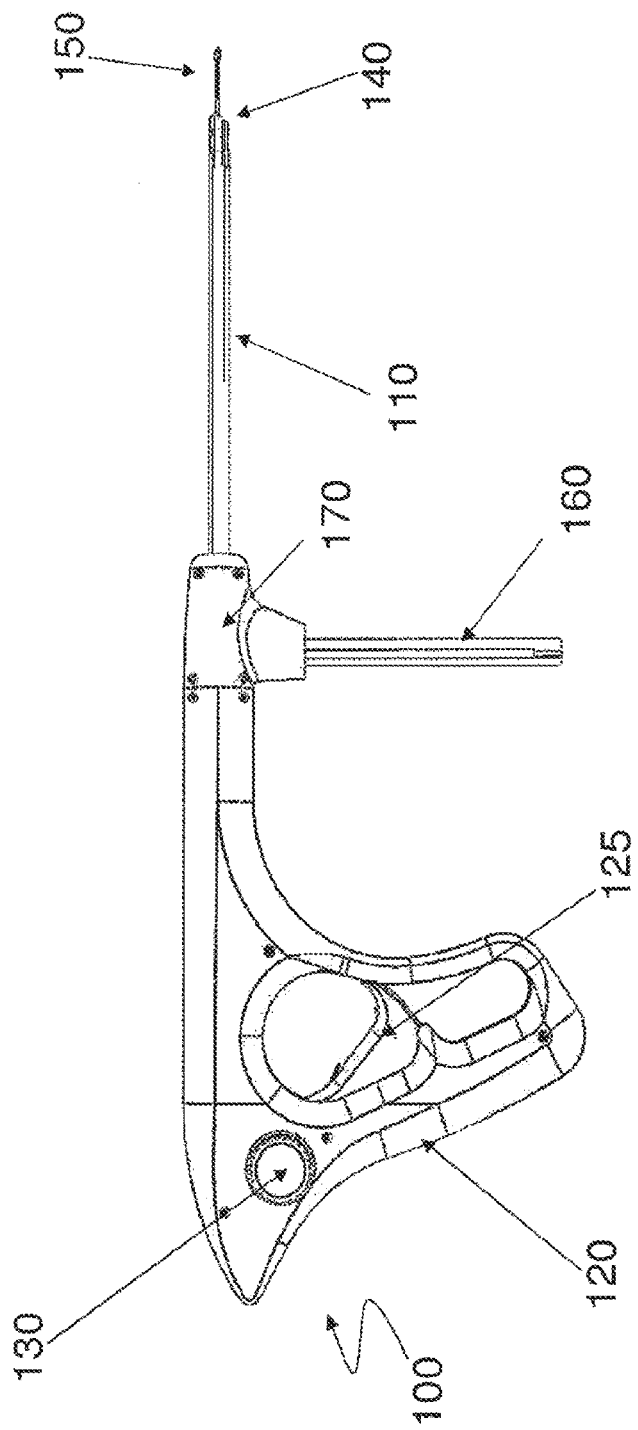
FIGS. 1A and B provide two different views of a disposable tissue modification device according to an embodiment of the invention.

Tissue modification devices are provided. Aspects of the devices include an elongated member having a proximal end and a distal end. The distal end of the elongated member is dimensioned to pass through a minimally invasive body opening and includes a distal end integrated visualization sensor and tissue modifier. In some instances, the devices further include an integrated articulation mechanism that imparts steerability to at least one of the visualization sensor, the tissue modifier and the distal end of the elongated member. Also provided are methods of modifying internal target tissue of a subject using the tissue modification devices.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, aspects of embodiments of the subject tissue modification devices are described first in greater detail. Next, embodiments of methods of modifying an internal target tissue of a subject in which the subject tissue modification devices may find use are reviewed in greater detail.

Tissue Modification Devices

Aspects of the invention include tissue modification devices useful for modifying an internal target tissue site, e.g., a spinal location that is near or inside of an intervertebral disc (IVD). As summarized above, the tissue modification devices are dimensioned such that at least the distal end of the devices can pass through a minimally invasive body opening. As such, at least the distal end of the devices may be introduced to an internal target site of a patient, e.g., a spinal location that is near or inside of an intervertebral disc, through a minimal incision, e.g., one that is less than the size of an incision employed for an access device having a outer diameter of 20 mm or smaller, e.g., less than 75% the size of such an incision, such as less than 50% of the size of such an incision, or smaller. In some instances, at least the distal end of the elongated member is dimensioned to pass through a Cambin's triangle. The Cambin's triangle (also known in the art as the Pambin's triangle) is an anatomical spinal structure bounded by an exiting nerve root and a traversing nerve root and a disc. The exiting root is the root that leaves the spinal canal just cephalad (above) the disc, and the traversing root is the root that leaves the spinal canal just caudad (below) the disc. Where the distal end of the elongated member is dimensioned to pass through a Cambin's triangle, at least the distal end of the device has a longest cross-sectional dimension that is 10 mm or less, such as 8 mm or less and including 7 mm or less. In some instances, the elongated member has an outer diameter that is 7.5 mm or less, such as 7.0 mm or less, including 6.7 mm or less, such as 6.6 mm or less, 6.5 mm or less, 6.0 mm or less, 5.5 mm or less, 5.0 mm or less.

As summarized above, tissue modification devices of the invention include an elongated member. As this component of the devices is elongated, it has a length that is 1.5 times or longer than its width, such as 2 times or longer than its width, including 5 or even 10 times or longer than its width, e.g., 20 times longer than its width, 30 times longer than its width, or longer. The length of the elongated member may vary, an in some instances ranges from 5 cm to 20 cm, such as 7.5 cm to 15 cm and including 10 to 12 cm. The elongated member may have the same outer cross-sectional dimensions (e.g., diameter) along its entire length. Alternatively, the cross-sectional diameter may vary along the length of the elongated member.

The elongated members of the subject tissue modification devices have a proximal end and a distal end. The term "proximal end", as used herein, refers to the end of the elongated member that is nearer the user (such as a physician operating the device in a tissue modification procedure), and the term "distal end", as used herein, refers to the end of the elongated member that is nearer the internal target tissue of the subject during use. The elongated member is, in some instances, a structure of sufficient rigidity to allow the distal end to be pushed through tissue when sufficient force is applied to the proximal end of the elongate member. As such, in these embodiments the elongated member is not pliant or flexible, at least not to any significant extent.

Depending on the particular device embodiment, the elongated member may or may not include one or more lumens that extend at least partially along its length. When present, the lumens may vary in diameter and may be employed for a variety of different purposes, such as irrigation, aspiration, electrical isolation (for example of conductive members, such as wires), as a mechanical guide, etc., as reviewed in greater detail below. When present, such lumens may have a longest cross section that varies, ranging in some in stances from 0.5 to 5.0 mm, such as 1.0 to 4.5 mm, including 1.0 to 4.0 mm. The lumens may have any convenient cross-sectional shape, including but not limited to circular, square, rectangular, triangular, semi-circular, trapezoidal, irregular, etc., as desired. These lumens may be provided for a variety of different functions, including as irrigation and/or aspiration lumens, as described in greater detail below.

As summarized above, the devices include a distal end integrated visualization sensor and a distal end integrated tissue modifier. As the visualization sensor is integrated at the distal end of the device, it cannot be removed from the remainder of the device without significantly compromising the structure and functionality of the device. Accordingly, the devices of the present invention are distinguished from devices which include a "working channel" through which a separate autonomous device, such as a tissue modifier, is passed through. In contrast to such devices, since the visualization sensor of the present device is integrated at the distal end, it is not a separate device from the elongated member that is merely present in a working channel of the elongated member and which can be removed from the working channel of such an elongated member without structurally compromising the elongated member in any way. The visualization sensor may be integrated with the distal end of the elongated member by a variety of different configurations. Integrated configurations include configurations where the visualization sensor is fixed relative to the distal end of the elongated member, as well as configurations where the visualization sensor is movable to some extent relative to the distal end of the elongated member. Movement of the visualization sensor may also be provided relative to the distal end of the elongated member, but then fixed with respect to another component present at the distal end, such as a distal end integrated tissue modifier. Specific configurations of interest are further described below in connection with the figures. In some instances, the devices may include two or more visualization sensors integrated at the distal end of the elongated member, e.g., as described in greater detail below.

Visualization sensors of interest include miniature imaging sensors that have a cross-sectional area which is sufficiently small for its intended use and yet retains a sufficiently high matrix resolution. For example, certain visualization sensors of the invention have a cross-sectional area (i.e., an x-y dimension, also known as packaged chip size) that is 2 mm×2 mm or less, such as 1.8 mm×1.8 mm or less, and yet have a matrix resolution of 400×400 or greater, such as 640×480 or greater. In some instances, the imaging sensors have a sensitivity that is 500 mV/Lux-sec or greater, such as 700 mV/Lux-Sec or greater, including 1000 mV/Lux-Sec or greater, where in some instances the sensitivity of the sensor is 2000 mV/Lux-Sec or greater, such as 3000 mV|Lux-Sec or greater. Imaging sensors of interest are those that include a photosensitive component, e.g., array of photosensitive elements that convert light into electrons, coupled to an integrated circuit. The integrated circuit may be configured to obtain and integrate the signals from the photosensitive array and output image data, which image data may in turn be conveyed to an extra-corporeal device configured to receive the data and display it to a user. The image sensors of these embodiments may be viewed as integrated circuit image sensors. The integrated circuit component of these sensors may include a variety of different types of functionalities, including but not limited to: image signal processing, memory, and data transmission circuitry to transmit data from the visualization sensor to an extra-corporeal location, etc. The miniature imaging sensors may further include a lens component made up of one or more lenses positioned relative to the photosensitive component so as to focus images on the photosensitive component. Where desired, the one or more lenses may be present in a housing. Specific types of miniature imaging sensors of interest include complementary metal-oxide-semiconductor (CMOS) sensors and charge-coupled device (CCD) sensors. The sensors may have any convenient configuration, including circular, square, rectangular, etc. Visualization sensors of interest may have a longest cross-sectional dimension that varies depending on the particular embodiment, where in some instances the longest cross sectional dimension (e.g., diameter) is 4.0 mm or less, such as 3.5 mm or less, including 3.0 mm or less, such as 2.5 mm or less, including 2.0 mm or less, including 1.5 mm or less, including 1.0 mm or less.

Imaging sensors of interest may be either front-side or backside illumination sensors, and have sufficiently small dimensions while maintaining sufficient functionality to be integrated at the distal end of the elongated members of the devices of the invention. Aspects of these sensors are further described in one or more the following U.S. Patents, the disclosures of which are herein incorporated by reference: U.S. Pat. Nos. 7,388,242; 7,368,772; 7,355,228; 7,345,330; 7,344,910; 7,268,335; 7,209,601; 7,196,314; 7,193,198; 7,161,130; and 7,154,137.

As the visualization sensor is a distal end integrated visualization sensor, it is located at or near the distal end of the elongated member. Accordingly, it is positioned at 3 mm or closer to the distal end, such as at 2 mm or closer to the distal end, including at 1 mm or closer to the distal end. In some instances, the visualization sensor is located at the distal end of the elongated member. The visualization sensor may provide for front viewing and/or side-viewing, as desired. Accordingly, the visualization sensor may be configured to provide image data as seen in the forward direction from the distal end of the elongated member. Alternatively, the visualization sensor may be configured to provide image data as seen from the side of the elongate member. In yet other embodiments, a visualization sensor may be configured to provide image data from both the front and the side, e.g., where the image sensor faces at an angle that is less than 90° relative to the longitudinal axis of the elongated member, e.g., as illustrated in FIGS. 6A to 6C, described in greater detail below.

Because the visualization sensor is a distal end integrated visualization sensor, the visualization sensor also includes functionality for conveying image data to an extracorporeal device, such as an image display device. In some instances, a signal cable (or other type of signal conveyance element) may be present to connect the image sensor at the distal end to a device at the proximal end of the elongate member, e.g., in the form of one or more wires running along the length of the elongate member from the distal to the proximal end. Alternatively, wireless communication protocols may be employed, e.g., where the imaging sensor is operatively coupled to a wireless data transmitter, which may be positioned at the distal end of the elongated member (including integrated into the visualization sensor, at some position along the elongated member or at the proximal end of the device, e.g., at a location of the proximal end of the elongated member or associated with the handle of the device).

In certain embodiments, a visualization sensor configuration as described in copending U.S. application Ser. No. 12/269,770 (the disclosure of which is herein incorporated by reference) is present in the device. In such embodiments, the device may include, at least during use, a visualization sensor configuration that is characterized by having two or more visualization sensors positioned at the distal end of the device. The two or more visualization sensors may be entirely integrated with the distal end of the device or distributed between the device and a second device, such as a separate access device or only on an access device. Accordingly, embodiments may include those systems where two or more visualization sensors are located at the distal end of the elongated member. Embodiments may also include those systems where one visualization element is located at the distal end of the elongated member and another visualization element is located at the distal end of the access device. Furthermore, embodiments may include those systems where two or more visualization elements are located at the distal end of the access device. It should be noted that while these particular visualization sensor configurations are described primarily in connection with a device that includes a distal end integrated tissue modification, also encompassed by the present invention are devices that include such a visualization sensor configuration but may not include integrated distal end tissue modifiers, e.g., as described in U.S. patent application Ser. No. 12/269,770 (the disclosure of which is herein incorporated by reference).

Where desired, the devices may include one or more illumination elements configured to illuminate a target tissue location so that the location can be visualized with a visualization sensor, e.g., as described above. A variety of different types of light sources may be employed as illumination elements, so long as their dimensions are such that they can be positioned at the distal end of the elongated member. The light sources may be integrated with a given component (e.g., elongated member) such that they are configured relative to the component such that the light source element cannot be removed from the remainder of the component without significantly compromising the structure of the component. As such, the integrated illumination element of these embodiments is not readily removable from the remainder of the component, such that the illumination element and remainder of the component form an interrelated whole. The light sources may be light emitting diodes configured to emit light of the desired wavelength range, or optical conveyance elements, e.g., optical fibers, configured to convey light of the desired wavelength range from a location other than the distal end of the elongate member, e.g., a location at the proximal end of the elongate member, to the distal end of the elongate member. As with the image sensors, the light sources may include a conductive element, e.g., wire, or an optical fiber, which runs the length of the elongate member to provide for power and control of the light sources from a location outside the body, e.g., an extracorporeal control device. In certain embodiments, the light sources may be configured to communicate wirelessly with an extracorporeal control device. Where desired, the light sources may include a diffusion element to provide for uniform illumination of the target tissue site. Any convenient diffusion element may be employed, including but not limited to a translucent cover or layer (fabricated from any convenient translucent material) through which light from the light source passes and is thus diffused.

Where desired, devices of the invention may include two or more illumination elements. In those embodiments of the invention where the system includes two or more illumination elements, the illumination elements may emit light of the same wavelength or they may be spectrally distinct light sources, where by "spectrally distinct" is meant that the light sources emit light at wavelengths that do not substantially overlap, such as white light and infra-red light. "White light" light sources are those light sources which are configured to illuminate a tissue location with white light, i.e., electromagnetic radiation of a wavelength that is visible to the human eye (about 400-700 nm), or up to 380-750 nm. Near-infra-red light sources are sources of light which are configured to illuminate a tissue location with near-infra-red light, i.e., near-infra-red radiation having wavelengths between about 700 nm and 1100 nm.

In certain embodiments where two or more distinct illumination elements are present, a controller may also be present which is configured to alternate illumination of the target tissue, e.g., an intervertebral disc or portion thereof, with the white light source and the near-infra-red source. By alternate is meant that at some point there is a switch from illumination with the white light source and illumination with the near-infrared light source. In these embodiments, the controller may also be configured to cause the image sensor(s) to obtain one or more images, e.g., stills or video, under each type of illumination, e.g., so as to obtain white light image data and infrared image data. The phrase "image data" refers to data that can be used by a processor to produce some type of human viewable image e.g., a still image or a video, on an appropriate display medium, e.g., a monitor.

In certain embodiments, a processor is configured to provide to a user multispectral image that is produced from image data obtained under white light illumination and near-infra-red illumination. The multi-spectral image may be generated to provide to a user a variety of different types of information not available to a user with image data obtained under a single spectra of illumination. For example, the multi-spectral image may be generated to provide a user with a three-dimensional effect that presents depth information to the user during use, e.g., during tissue dissection, irrigation and aspiration.

In certain embodiments, a processor may be configured to produce a video from the image data that is obtained under white light, under near-infra-red light or a combination of data taken under illumination of both kinds of light, i.e., to produce a multi-spectral or combined video. For example, if the target tissue site is relatively free of fluid, a user may desire to view the site under white light illumination. Alternatively, where the target tissue site is filled with fluid, a user may desire to view the site under near-infra-red illumination.

In certain embodiments, an illumination configuration made up of two or more illumination elements as described in copending U.S. application Ser. Nos. 12/269,770 and 12/269,772 (the disclosures of which are herein incorporated by reference) is present in the device. It should be understood that while embodiments of the invention having two or more light sources are described herein primarily with respect to minimally invasive tissue modification devices also having an integrated tissue modifier at the distal end, embodiments of the invention having two or more distal end illumination elements but lacking a distal end tissue modifier and/or visualization sensor (e.g., as described in U.S. application Ser. Nos. 12/269,770 and 12/269,772 (the disclosures of which are herein incorporated by reference)) are also included within the scope of the invention. Accordingly, embodiments may include those systems where two or more illumination elements are located at the distal end of the elongated member. Embodiments may also include those systems where one illumination element is located at the distal end of the elongated member and another illumination element is located at the distal end of a second device, such as an access device. Furthermore, embodiments may include those systems where two or more illumination elements are located at the distal end of a second device, such as an access device.

In addition to a distal end integrated visualization sensor, devices of embodiments of the invention further include an integrated distal end tissue modifier. As the tissue modifier is integrated at the distal end of the device, it cannot entirely be removed from the remainder of the device without significantly compromising the structure and functionality of the device. While the tissue modifier cannot entirely be removed from the device without compromising the structure and functionality of the device, components of the tissue modifier may be removable and replaceable. For example, an RF electrode tissue modifier may be configured such that the wire component of the tissue modifier may be replaceable while the remainder of the tissue modifier is not. Accordingly, the devices of the present invention are distinguished from devices which include a "working channel" through which a separate autonomous tissue modifier device, such as autonomous RF electrode device, is passed through. In contrast to such devices, since the tissue modifier of the present device is integrated at the distal end, it is not a separate device from the elongated member that is merely present in a working channel of the elongated member and which can be removed from the working channel of such an elongated member without structurally compromising the elongated member in any way. The tissue modifier may be integrated with the distal end of the elongated member by a variety of different configurations. Integrated configurations include configurations where the tissue modifier is fixed relative to the distal end of the elongated member, as well as configurations where the tissue modifier is movable to some extent relative to the distal end of the elongated member may be employed in devices of the invention. Specific configurations of interest are further described below in connection with the figures. As the tissue modifier is a distal end integrated tissue modifier, it is located at or near the distal end of the elongated member. Accordingly, it is positioned at 10 mm or closer to the distal end, such as at 5 mm or closer to the distal end, including at 2 mm or closer to the distal end. In some instances, the tissue modifier is located at the distal end of the elongated member.

Tissue modifiers are components that interact with tissue in some manner to modify the tissue in a desired way. The term modify is used broadly to refer to changing in some way, including cutting the tissue, ablating the tissue, delivering an agent(s) to the tissue, freezing the tissue, etc. As such, of interest as tissue modifiers are tissue cutters, tissue ablators, tissue freezing/heating elements, agent delivery devices, etc. Tissue cutters of interest include, but are not limited to: blades, liquid jet devices, lasers and the like. Tissue ablators of interest include, but are not limited to ablation devices, such as devices for delivery ultrasonic energy (e.g., as employed in ultrasonic ablation), devices for delivering plasma energy, devices for delivering radiofrequency (RF) energy, devices for delivering microwave energy, etc. Energy transfer devices of interest include, but are not limited to: devices for modulating the temperature of tissue, e.g., freezing or heating devices, etc. In some embodiments, the tissue modifier is not a tissue modifier that achieves tissue modification by clamping, clasping or grasping of tissue such as may be accomplished by devices that trap tissue between opposing surfaces (e.g., jaw-like devices). In these embodiments, the tissue modification device is not an element that is configured to apply mechanical force to tear tissue, e.g., by trapping tissue between opposing surfaces. In some embodiments, tissue modification comprises an action other than just removal by low pressure irrigation or aspiration, for example where some other act is performed on the tissue beyond low pressure irrigation and/or aspiration. In some embodiments, the tissue modifier is distinct from a probe element or device that is configured to move tissue without any modification to the tissue other than simple displacement or repositioning, such as through retraction, atraumatic movement, etc.

In some instances, the tissue modifier includes at least one electrode. For example, tissue modifiers of interest may include RF energy tissue modifiers, which include at least one electrode and may be configured in a variety of different ways depending on the desired configuration of the RF circuit. An RF circuit can be completed substantially entirely at target tissue location of interest (bipolar device) or by use of a second electrode attached to another portion of the patient's body (monopolar device). In either case, a controllable delivery of RF energy is achieved. Aspects of the subject tissue modification devices include a radiofrequency (RF) electrode positioned at the distal end of the elongated member. RF electrodes are devices for the delivery of radiofrequency energy, such as ultrasound, microwaves, and the like. In some instances, the RF electrode is an electrical conductor for delivering RF energy to a particular location, such as a desired target tissue. For instance, in certain cases, the RF electrode can be an RF ablation electrode. RF electrodes of the subject tissue modification devices can include a conductor, such as a metal wire, and can be dimensioned to access an intervertebral disc space. RF electrodes may be shaped in a variety of different formats, such as circular, square, rectangular, oval, etc. The dimensions of such electrodes may vary, where in some embodiments the RF electrode has a longest cross-sectional dimension that is 7 mm or less, 6 mm or less 5 mm or less, 4 mm or less, 3 mm or less or event 2 mm or less, as desired. Where the electrode includes a wire, the diameter of the wire in such embodiments may be 180 um, such as 150 um or less, such as 130 um or less, such as 100 um or less, such as 80 um or less. A variety of different RF electrode configurations suitable for use in tissue modification and include, but are not limited to, those described in U.S. Pat. Nos. 7,449,019; 7,137,981; 6,997,941; 6,837,887; 6,241,727; 6,112,123; 6,607,529; 5,334,183. RF electrode systems or components thereof may be adapted for use in devices of the present invention (when coupled with guidance provided by the present specification) and, as such, the disclosures of the RF electrode configurations in these patents are herein incorporated by reference. Specific RF electrode configurations of interest are further described in connection with the figures, below.

In some instances, the tissue modifier is supplied with current from an RF energy source. The voltage signal driving the current to the tissue modifier may be definable as a sine, square, saw-tooth, triangle, pulse, non-standard, complex, or irregular waveform, or the like, with a well-defined operating frequency. For example, the operating frequency can range from 1 KHz to 50 MHz, such as from 100 KHz to 25 MHz, and including from 250 KHz to 10

MHz. In some embodiments, the RF voltage signal is a sine wave with operating frequency 460 kHz. Furthermore, the tissue modifier's operating frequency can be modulated by a modulation waveform. By "modulated" is meant attenuated in amplitude by a second waveform, such as a periodic signal waveform. The modulation waveform may be definable as a sine, square, saw-tooth, triangle, pulse, non-standard, complex, or irregular waveform, or the like, with a well-defined modulation frequency. For example, the modulation frequency can range from 1 HZ to 10 kHz, such as from 1 HZ to 500 Hz, and including from 10 HZ to 100 Hz. In some embodiments, the modulation waveform is a square wave with modulation frequency 70 Hz.

In some embodiments, a RF tuner is included as part of the RF energy source. The RF tuner includes basic electrical elements (e.g., capacitors and inductors) which serve to tailor the output impedance of the RF energy source. The term "tailor" is intended here to have a broad interpretation, including affecting an electrical response that achieves maximum power delivery, affecting an electrical response that achieves constant power (or voltage) level under different loading conditions, affecting an electrical response that achieves different power (or voltage) levels under different loading conditions, etc. Furthermore, the elements of the RF tuner can be chosen so that the output impedance is dynamically tailored, meaning the RF tuner self-adjusts according to the load impedance encountered at the electrode tip. For instance, the elements may be selected so that the electrode has adequate voltage to develop a plasma corona when the electrode is placed in a saline solution (with saline solution grounded to return electrode), but then may self-adjust the voltage level to a lower threshold when the electrode contacts tissue (with tissue also grounded to return electrode, for example through the saline solution), thus dynamically maintaining the plasma corona at the electrode tip while minimizing the power delivered to the tissue and the thermal impact to surrounding tissue. RF tuners, when present, can provide a number of advantages. For example, delivering RF energy to target tissue through the distal tip of the electrode is challenging since RF energy experiences attenuation and reflection along the length of the conductive path from the RF energy source to the electrode tip, which can result in insertion loss. Inclusion of a RF tuner, e.g., as described above, can help to minimize and control insertion loss.

Devices of the invention may include a linear mechanical actuator for linearly translating a distal end element of the device, such as the tissue modifier (e.g., a RF electrode) relative to the distal end of the elongate member. By "linearly translating" is meant moving the tissue modifier along a substantially straight path. As used herein, the term "linear" also encompasses movement of the tissue modifier in a non-straight (i.e., curved) path. For instance, the path of movement of the tissue modifier can be deflected from a substantially straight path if the electrode encounters a tissue of a different density (such as, cartilage, bone, etc.), or if the conformation of the tissue the electrode is passing through is not straight, etc.

When actuated by a linear mechanical actuator, the tissue modifier is cyclically displaced from a "neutral" position along its axial extension to positions displaced distally or proximally from the neutral position, with maximum displacement from the neutral position corresponding to the vibratory amplitude. Thus, the linear mechanical actuator actuates the tissue modifier through a distance equal to twice the vibratory amplitude and ranging from a distal extreme position to a proximal extreme position. In certain embodiments, the tissue modifier can be extended by the linear mechanical actuator from the distal end of the elongated member by 0.1 mm or more, such as 0.5 mm or more, including 1 mm or more, for instance 2 mm or more, such as 5 mm or more. This back and forth movement of the tissue modifier relative to the distal end of the elongated member that is implemented by the linear mechanical actuator is described herein in terms of linear translation frequency. It is noted that the above described distal and proximal extreme positions refer to those positions implemented solely by the linear mechanical actuator. In some embodiments, the linear mechanical actuator may be the only means for translating the electrode. In other embodiments, e.g., as described in greater detail below, the linear mechanical actuator may provide vibratory amplitude that is superimposed on another independent control over electrode translation which moves the electrode over a distance significantly greater than the vibratory amplitude, e.g. 10 mm or more, such as 20 mm or more, including 30 mm or more, for instance 40 mm or more. In this case, the tissue modifier may be extended beyond the range defined by the above described linear mechanical actuator distal and proximal extreme positions. For example, a manual control (e.g., a thumbwheel or analogous structure) may be provided on the device which permits a user to move the tissue modifier relative to the distal end in a movement that is distinct from that provided by the linear mechanical actuator.

Accordingly, devices of the invention may include a linear mechanical actuator configured to linearly translate the tissue modifier relative to the distal end at linear translation frequency. The linear mechanical actuator can be any of a variety of actuators convenient for use in the subject devices for linearly translating the tissue modifier relative to the distal end of the elongated member. For instance, the linear mechanical actuator can be a voice coil motor (VCM), solenoid, pneumatic actuator, electric motor, etc. The linear mechanical actuator is operatively coupled to the tissue modifier. By "operatively coupled" is meant that the linear mechanical actuator is connected to the tissue modifier such that linear movement by the actuator is transferred to the tissue modifier thereby extending the tissue modifier from the distal end of the elongated member or retracting the tissue modifier towards the distal end of the elongated member depending on the direction of movement by the linear actuator.

When present, the linear actuator provides for linear translation of the tissue modifier at a linear translation frequency. In some instances, the linear translation frequency is 10 Hz or greater, such as 25 Hz or greater, including 50 HZ or greater, such as 100 Hz or greater. In some embodiments, the linear translation frequency is 70 Hz. In certain cases, the translation of the tissue modifier between the distal and proximal extreme positions occurs with a predetermined linear translation frequency while in other embodiments the linear translation frequency may not be predetermined. The translation frequency (whether or not predetermined) may depend on various factors, such as but not limited to, the type of tissue being modified, the amount of tissue being modified, the location of the tissue, the proximity of surrounding tissues, the conformation of the tissue, the type of procedure being performed, the nature of the linear mechanical actuator, the DC voltage applied to the actuator, the amplitude of the AC voltage applied to the actuator, etc. For example, in certain embodiments, the linear translation frequency is definable as a standard waveform, such as a sine waveform. In some cases, the sine waveform is an HZ sine waveform, such that the linear translation frequency ranges from 1 HZ to 500 Hz, such as from 1 HZ to 250 Hz, and including from 10 HZ to 100 Hz. In other cases, the linear translation frequency is definable as a nonstandard, complex, or irregular waveform, or the like. For example, the linear translation frequency can be definable as a waveform comprising periods that have varying frequencies, a waveform comprising periods that have varying amplitudes, a waveform comprising periods that have varying frequencies and varying amplitudes, a superposition of two or more waveforms, and the like.

In some embodiments, the tissue modification device is configured to synchronize the linear mechanical actuation with the modulated RF waveform. By "synchronize" is meant that two or more events are timed to operate in a coordinated manner. For example, two or more waveforms can be timed to operate in a coordinated manner. In some embodiments, the modulation frequency equals the linear translation frequency, and the modulation waveform is phase-shifted relative to the linear translation waveform. Synchronization of these waveforms may be achieved using a variety of different protocols and may implement one or more controllers of different formats, including hardware, software, and combinations thereof. For instance, a single common controller may generate two waveforms that are phase-shifted; alternatively, separate controllers can be arranged in a master-slave configuration to generate two waveforms that are phase-shifted; alternatively, one controller can generate a waveform, hardware (e.g., an optoelectronic encoder, a mechanical encoder, a hall sensor, or the like) can be used to trigger on a physical embodiment (such as mechanical rotation) of that waveform, and a second controller can generate a second waveform with adjustable phase shift from the trigger signal. The phase shift of the modulation waveform relative to the linear translation waveform can be positive (phase lead) or negative (phase lag), and can have magnitude 0° to 360° or more, such as 0° to 180°, including 60° to 120°. In certain embodiments of the invention, the modulation waveform lags the linear translation waveform by 90°.

As discussed above, the tissue modifier (e.g., a RF electrode) has distal and proximal extreme positions of its cyclic linear translation. In certain embodiments, the tissue modifier is configured to deliver RF energy to an internal target tissue while at a position other than the distal extreme position. Thus, in these cases, the modulation waveform is synchronized with the linear translation waveform such that the tissue modifier is energized when the tissue modifier is at a position other than the distal extreme position, such as while the tissue modifier is at or near the proximal extreme position. For example, as discussed above, the modulating waveform may be phase-shifted relative to the linear translation waveform.

Cyclic linear translation of the tissue modification device can facilitate a variety of functions with multiple benefits. For instance, cyclic linear translation of the tissue modifier at a fast rate relative to manually controlled translation (e.g., at a frequency greater than 10 Hz) will tend to physically advance the tissue modifier into soft tissue due to the compliance of the soft tissue, while hard tissue will resist deformation and will thus not allow the tissue modifier to physically advance into the hard tissue. Consequently, the electrode will push back against the elongated body as it encounters hard tissue, thus producing tactile feedback to the user. In some embodiments, synchronization of the tissue modifier's modulation waveform with its linear translation waveform provides additional benefits. For instance, rapid retraction of the electrode from hard tissue that it encounters will leave the tissue modifier physically separated from the hard tissue by a gap as the tissue modifier approaches the proximal extreme position. In some embodiments, the tissue modifier tip is activated only when the tissue modifier is at or near the proximal extreme position, as mentioned above. This has the effect of preferentially delivering the tissue modification energy to soft, compliant tissue as opposed to hard, stiff tissue. Stated otherwise, this provides tissue discrimination based on elastic modulus. In the case of spinal surgery applications requiring removal of nuclear material, such as fusion, total disc replacement, and partial disc replacement, synchronization of the modulation waveform with the linear translation waveform facilitates the delivery of tissue modification energy to the nucleus pulposus (soft, compliant tissue) while minimizing the delivery of tissue modification energy to the disc annulus (hard, stiff tissue) and the endplates of the vertebral bodies (hard, stiff tissue). In addition, cyclic linear translation of the tissue modifier helps to prevent a condition where the electrode sticks to tissue as it ablates it, resulting in increased thermal effects to the surrounding tissue, ineffective or discontinuous tissue dissection, buildup of charred or otherwise modified tissue on the tissue modifier tip, or a combination thereof. Additionally, cyclic linear translation of the tissue modifier helps chop the dissected tissue into smaller pieces, thus facilitating aspiration of the dissected tissue.

In some instances, the device includes one or more sensors configured to obtain linear translation data. By linear translation data is meant information about the linear translation of the RF electrode, where such information may include information about the direction of translation, velocity of translation, acceleration/deceleration of translation, etc. The sensor or sensors, when present, may be positioned at any convenient location of the elongate member, e.g., at the distal end, etc., so long as the sensor or sensors are positioned so that the desired linear translation data may be obtained. Any of a variety of different types of sensors may be employed, where sensors of interest include, but are not limited to: optical encoders, mechanical encoders, optoelectronic sensors, Hall effect sensors, position sensors, motion detection sensors, and the like.

Additional details regarding linear translation are provided in U.S. application Ser. No. 12,467,122, the disclosure of which application is herein incorporated by reference. It should be understood that while the linear mechanical actuator element is described herein primarily with respect to devices that include integrated distal end visualization, such as depicted in FIG. 1, also encompassed within the scope of the invention are devices that include distal end linear translation of any element that is positioned at the distal end of the device.

Depending on the nature of the tissue modifier, the devices will include proximal end connectors for operatively connecting the device and tissue modifier to extracorporeal elements required for operability of the tissue modifier, such as extracorporeal RF controllers, mechanical tissue cutter controllers, liquid jet controllers, etc.

In some embodiments, an integrated articulation mechanism that imparts steerability to at least one of the visualization sensor, the tissue modifier and the distal end of the elongated member is also present in the device. By "steerability" is meant the ability to maneuver or orient the visualization sensor, tissue modifier and/or distal end of the elongated member as desired during a procedure, e.g., by using controls positioned at the proximal end of the device. In these embodiments, the devices include a steerability mechanism (or one or more elements located at the distal end of the elongated member) which renders the desired distal end component maneuverable as desired through proximal end control. As such, the term "steerability", as used herein, refers to a mechanism that provides a user steering functionality, such as the ability to change direction in a desired manner, such as by moving left, right, up or down relative to the initial direction. The steering functionality can be provided by a variety of different mechanisms. Examples of suitable mechanisms include, but are not limited to one or more wires, tubes, plates, meshes or combinations thereof, made from appropriate materials, such as shape memory materials, music wire, etc. In some instances, the distal end of the elongated member is provided with a distinct, additional capability that allows it to be independently rotated about its longitudinal axis when a significant portion of the operating handle is maintained in a fixed position, as discussed in greater detail below. The extent of distal component articulations of the invention may vary, such as from −180 to +180°; e.g., −90 to +90°. Alternatively, the distal probe tip articulations may range from 0 to 360°, such as 0 to +180°, and including 0 to +90°, with provisions for rotating the entire probe about its axis so that the full range of angles is accessible on either side of the axis of the probe, e.g., as described in greater detail below. Articulation mechanisms of interest are further described in published PCT Application Publication Nos. WO 2009029639; WO 2008/094444; WO 2008/094439 and WO 2008/094436; the disclosures of which are herein incorporated by reference. Specific articulation configurations of interest are further described in connection with the figures, below.

In certain embodiments, devices of the invention may further include an irrigator and aspirator configured to flush an internal target tissue site and/or a component of the device, such as a lens of the visualization sensor. As such, the elongated member may further include one or more lumens that run at least the substantial length of the device, e.g., for performing a variety of different functions, as summarized above. In certain embodiments where it is desired to flush (i.e., wash) the target tissue site at the distal end of the elongated member (e.g. to remove ablated tissue from the location, etc.), the elongated member may include both irrigation lumens and aspiration lumens. Thus, the tissue modification device can comprise an irrigation lumen located at the distal end of the elongated member, and the tissue modification device can include an aspiration lumen located at the distal end of the elongated member. During use, the irrigation lumen is operatively connected to a fluid source (e.g., a physiologically acceptable fluid, such as saline) at the proximal end of the device, where the fluid source is configured to introduce fluid into the lumen under positive pressure, e.g., at a pressure ranging from 0 psi to 60 psi, so that fluid is conveyed along the irrigation lumen and out the distal end. While the dimensions of the irrigation lumen may vary, in certain embodiments the longest cross-sectional dimension of the irrigation lumen ranges from 0.5 mm to 5 mm such as 0.5 mm to 3 mm, including 0.5 mm to 1.5 mm. During use, the aspiration lumen is operatively connected to a source of negative pressure (e.g., a vacuum source) at the proximal end of the device. While the dimensions of the aspiration lumen may vary, in certain embodiments the longest cross-sectional dimension of the aspiration lumen ranges from 1 mm to 7 mm, such as 1 mm to 6 mm, including 1 mm to 5 mm. In some embodiments, the aspirator comprises a port having a cross-sectional area that is 33% or more, such as 50% or more, including 66% or more, of the cross-sectional area of the distal end of the elongated member. In some instances, the negative pressure source is configured to draw fluid and/or tissue from the target tissue site at the distal end into the aspiration lumen under negative pressure, e.g., at a negative pressure ranging from 300 to 600 mmHg, such as 550 mmHg, so that fluid and/or tissue is removed from the tissue site and conveyed along the aspiration lumen and out the proximal end, e.g., into a waste reservoir. In certain embodiments, the irrigation lumen and aspiration lumen may be separate lumens, while in other embodiments, the irrigation lumen and the aspiration lumen can be included in a single lumen, for example as concentric tubes with the inner tube providing for aspiration and the outer tube providing for irrigation. When present, the lumen or lumens of the flushing functionality of the device may be operatively coupled to extra-corporeal irrigation devices, such as a source of fluid, positive and negative pressure, etc. Where desired, irrigators and/or aspirators may be steerable, as described above.

Where desired, the devices may include a control structure, such as a handle, operably connected to the proximal end of the elongated member. By "operably connected" is meant that one structure is in communication (for example, mechanical, electrical, optical connection, or the like) with another structure. When present, the control structure (e.g., handle) is located at the proximal end of the device. The handle may have any convenient configuration, such as a hand-held wand with one or more control buttons, as a hand-held gun with a trigger, etc., where examples of suitable handle configurations are further provided below.

In some embodiments, the distal end of the elongated member is rotatable about its longitudinal axis when a significant portion of the operating handle is maintained in a fixed position. As such, at least the distal end of the elongated member can turn by some degree while the handle attached to the proximal end of the elongated member stays in a fixed position. The degree of rotation in a given device may vary, and may range from 0 to 360°, such as 0 to 270°, including 0 to 180°.

Devices of the invention may be disposable or reusable. As such, devices of the invention may be entirely reusable (e.g., be multi-use devices) or be entirely disposable (e.g., where all components of the device are single-use). In some instances, the device can be entirely reposable (e.g., where all components can be reused a limited number of times). Each of the components of the device may individually be single-use, of limited reusability, or indefinitely reusable, resulting in an overall device or system comprised of components having differing usability parameters.

Devices of the invention may be fabricated using any convenient materials or combination thereof, including but not limited to: metallic materials such as tungsten, stainless steel alloys, platinum or its alloys, titanium or its alloys, molybdenum or its alloys, and nickel or its alloys, etc.; polymeric materials, such as polytetrafluoroethylene, polyimide, PEEK, and the like; ceramics, such as alumina (e.g., STEATITE™ alumina, MAECOR™ alumina), etc.

In addition, devices of the invention may include a distal end integrated nonvisualization sensor. In other words, the devices may include one or more nonvisualization sensors that are integrated at the distal end of the elongated member. It should be understood that while the non-visualization sensor is described herein primarily with respect to tissue modification devices having a non-visualization sensor at a distal end, other minimally invasive devices may also include a non-visualization sensor at a distal end.

The one or more non-visualization sensors are sensors that are configured to obtain non-visual data from a target location. Non-visual data of interest includes, but is not limited to: temperature, pressure, pH, elasticity, impedance, conductivity, distance, size, etc. Non-visualization sensors of interest include those configured to obtain one or more types of the non-visual data of interest. Examples of sensors that may be integrated at the distal end include, but are not limited to: temperature sensors, pressure sensors, pH sensors, impedance sensors, conductivity sensors, elasticity sensors, etc. Specific types of sensors include, but are not limited to: thermistors, strain gauges, membrane containing sensors, MEMS sensors, electrodes, light sensors, etc. The choice of a specific type of sensor will depend on the nature of the non-visual data of interest. For example, a pressure sensor can detect the force applied to a target tissue as it is deformed to determine the elastic modulus of the target tissue. A temperature sensor can be employed to detect locally elevated temperatures (which can be used to differentiate different types of tissue, such as to different normal and tumor tissue (where tumors exhibit increased bloodflow and therefore a higher temperature)). A properly collimated laser beam could be used to determine the distance to objects in the device field of view or the length scale of objects in the device field of view. When present, the integrated non-visualization sensor or sensors may be configured to complement other distal end components of the devices, so as to minimize any impact on the outer dimension of the distal end, e.g., in ways analogous to those described above in connection with integrated illumination elements.

Devices of the invention may also include components which are shielded—e.g., shielded from an ambient RF field. It should be understood that while the feature of RF shielding is described herein primarily with respect to tissue modification devices having RF-shielding, other minimally invasive devices may also include RF-shielding.

In certain embodiments, a visualization module including one or more visualization sensors may comprise an RF-shield. The RF-shielded visualization sensor module is integrated with the elongated member. As the RF-shielded visualization sensor module is integrated with the elongated member, it cannot be removed from the remainder of the elongated member and device without significantly compromising the structure and functionality of the device. Accordingly, the devices of the present invention are distinguished from devices which include a 'working channel" through which a separate autonomous device is passed through. In contrast to such devices, since the RF-shielded visualization sensor module of the present device is integrated with the elongated member, it is not a separate device from the elongated member that is merely present in a working channel of the elongated member and which can be removed from the working channel of such an elongated member without structurally compromising the elongated member in any way. The visualization sensor module may be integrated with the elongated member by a variety of different configurations. Integrated configurations include configurations where the visualization sensor of the visualization sensor module is fixed relative to the distal end of the elongated member, as well as configurations where the visualization sensor of the visualization sensor module is movable to some extent relative to the distal end of the elongated member. Movement of the visualization sensor of the visualization sensor module may also be provided relative to the distal end of the elongated member, but then fixed with respect to another component present at the distal end, such as a distal end integrated tissue modifier.

As the visualization sensor module is RF-shielded, the visualization sensor module includes an RF shield that substantially inhibits, if not completely prevents, an ambient RF field from reaching and interacting with circuitry of the visualization sensor. As such, the RF shield is a structure which substantially inhibits, if not completely prevents, ambient RF energy (e.g., as provided by a distal end RF electrode) from impacting the circuitry function of the visualization sensor.

The RF shield of the visualization sensor module may have a variety of different configurations. The RF shield may include an enclosure element or elements which serve to shield the circuitry of the visualization sensor from an ambient RF field. In some instances, the RF shield is a grounded conductive enclosure component or components which are associated with the visualization sensor, conductive member and other components of the visualization sensor module. In some instances, the visualization sensor of the visualization sensor module is present in a housing, where the housing may include a grounder outer conductive layer which serves as an RF shield component. In these instances, the RF shield is an outer grounded conductive layer. The conductive enclosure or enclosures of the RF-shielded visualization sensor module may be fabricated from a variety of different conductive materials, such as metals, metal alloys, etc., where specific conductive materials of interest include, but are not limited to: copper foils and the like. In certain instances, the RF shield is a metallic layer. This layer, when present, may vary in thickness, but in some instances has a thickness ranging from 0.2 mm to 0.7 mm, such as 0.3 mm to 0.6 mm and including 0.4 mm to 0.5 mm.

Further details regarding RF shielded visualization sensor modules are provided in U.S. patent application Ser. No. 12/437,865, the disclosure of which is herein incorporated by reference. It should be noted that while the RF shielded visualization sensor module is described primarily in connection with devices that include distal end integrated tissue modifiers, also coming within the scope of the invention are devices that include such visualization sensor modules but lack distal end tissue modifiers.

Tissue modification devices of the invention may be configured to be hand-held. Accordingly, in certain instances the tissue modification devices have a mass that is 1.5 kg or less, such as 1 kg or less, including 0.5 kg or less, e.g., 0.25 kg or less.

Figure 1B:
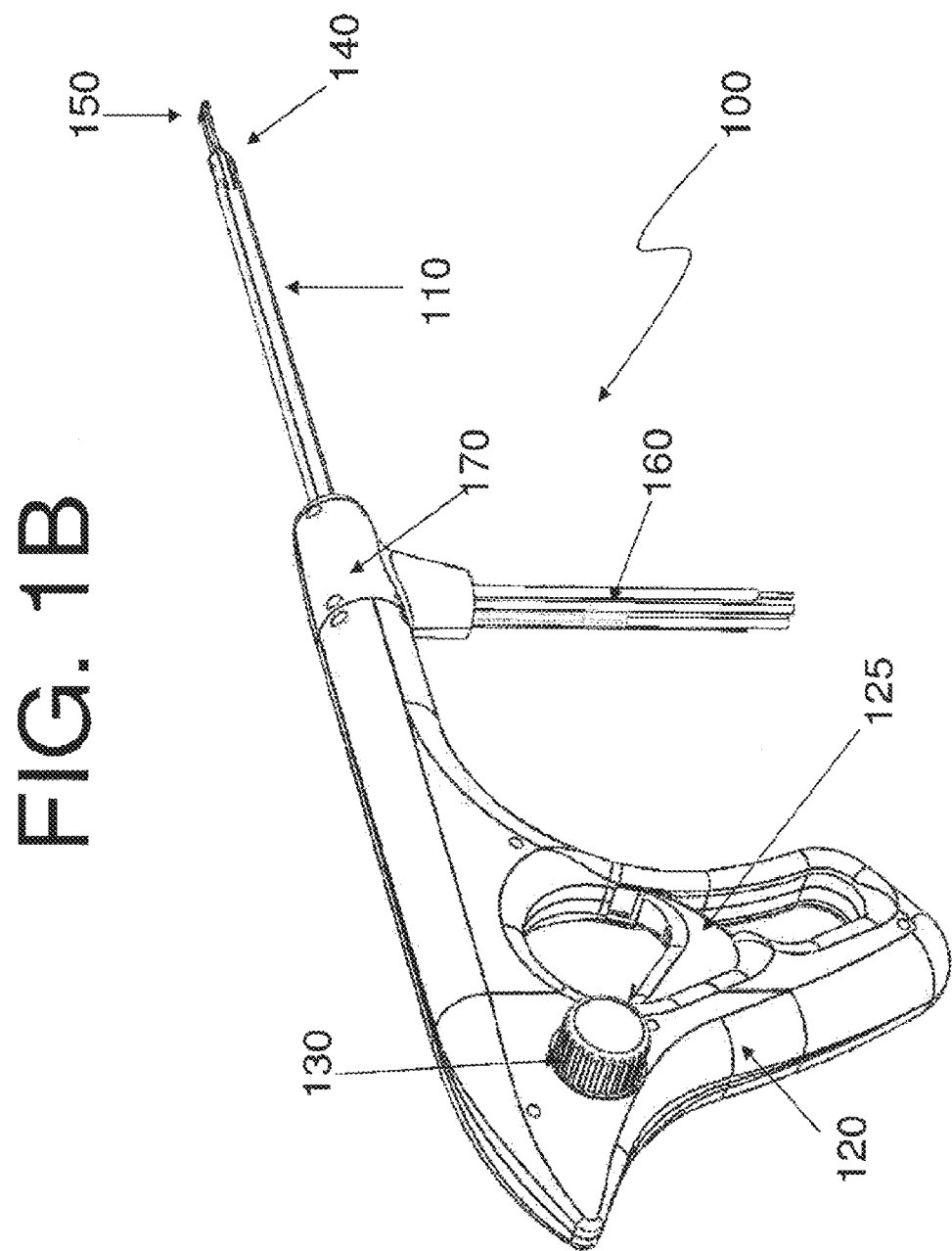

Various aspects of device embodiments of the invention have been described in varying detail above. Device embodiments will now be described in further detail in terms of figures. FIGS. 1A and 1B provide two different side views of a device 100 according to one embodiment of the invention. Device 100 includes an elongated member 110 and an operating handle 120 at the proximal end of the elongated member 110. The operating handle has a gun configuration and includes a trigger 125 and thumbwheel 130 which provide a user with manual operation over certain functions of the device, e.g., RF electrode positioning and extension. Located at the distal end of the elongated member is an integrated visualization sensor 140 and tissue modifier 150. Control elements 160 (which may include aspiration and irrigation lumens, control/power wires, etc.) exit the handle 120 at the distal end region 170, which region 170 is rotatable relative to the remainder of the handle 120. A variety of additional components may be present at the distal end of the elongated member, which additional elements may include irrigators, aspirators, articulation mechanisms, etc. as described generally above. More details regarding the distal end of elongate member 140 may be seen in FIG. 6D.

Figure 2B:
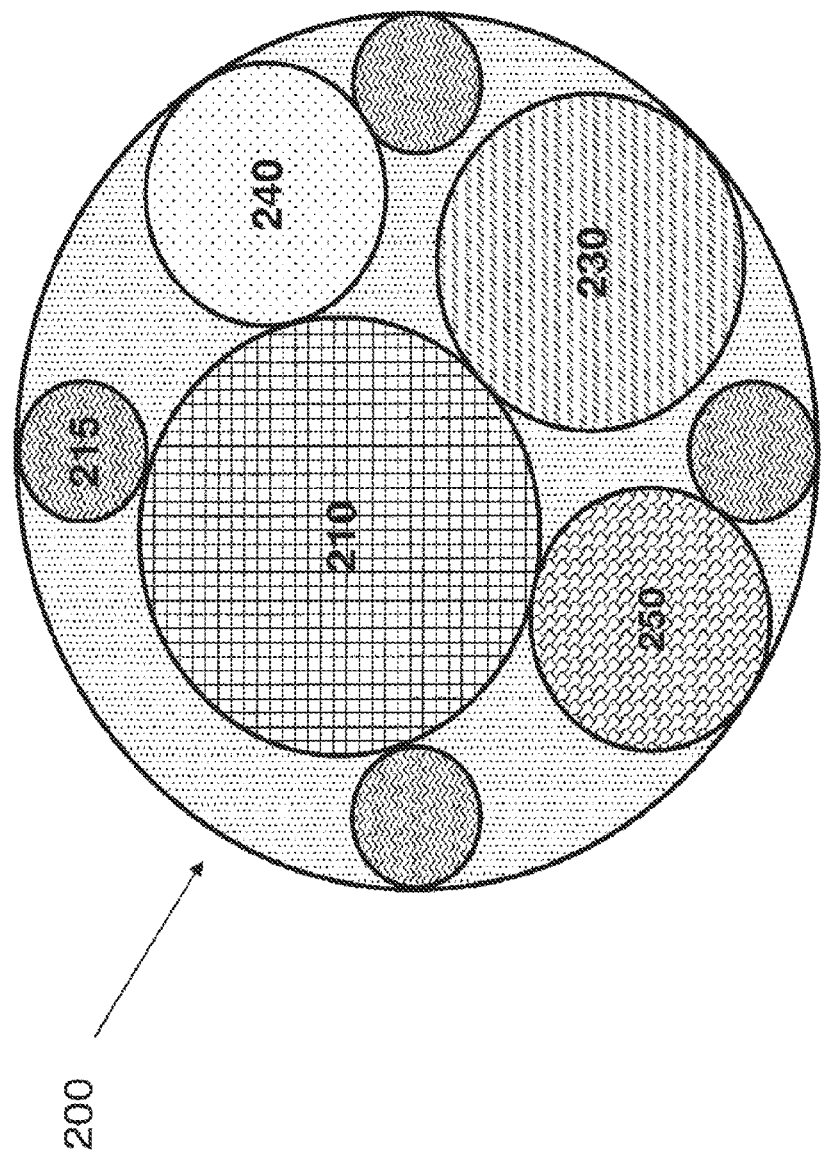
Figure 2C:
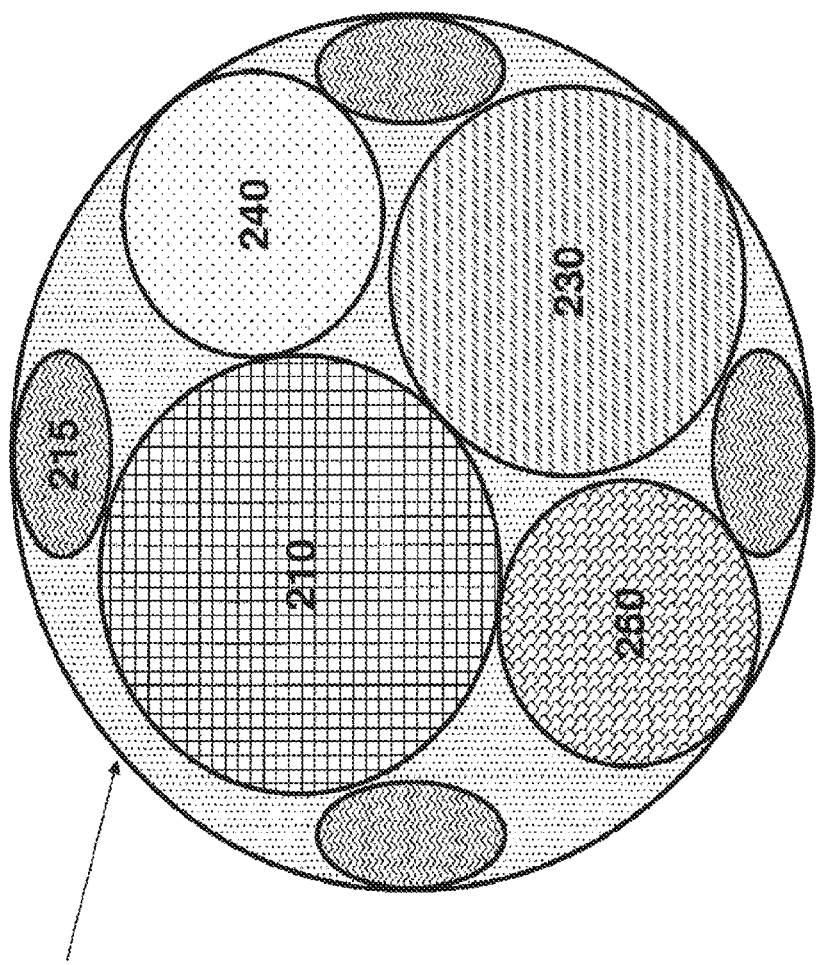

FIGS. 2A to 2C provide cross-sectional views of the distal ends of elongated members according to three different embodiments of the device. Each of these views shows how the visualization sensor and tissue modifier may be integrated at the distal end despite the limited size of the distal end.

FIG. 2A shows an example cross-section of the distal end 200 of an elongated member of a device according one embodiment of the invention. Distal end 200 includes an integrated CMOS visualization sensor 210, which has a 2.5 mm diameter. Also shown are guide-wires 215 which have a 1 mm diameter and provide for articulation of the distal end of the device. Integrated mechanical cutter 230 has a 1.58 mm diameter. Light source 240 has a 1.33 mm diameter. Also shown is lumen 250 which provides for aspiration and irrigation. FIG. 2A is drawn to scale, demonstrating that integrated visualization, tissue modification, illumination and irrigation can be positioned at the distal end of an elongated member that has a 5.00 mm outer diameter.

FIG. 2B shows the cross-section of a distal end of elongated member that is analogous to that shown in FIG. 2A, with the exception that smaller diameter guidewires (0.80 mm) are employed. As a result, light source 240 may have a 1.50 mm diameter and mechanical cutter 230 may have a 1.92 mm diameter. Like the embodiment shown in FIG. 2A, FIG. 2B is drawn to scale, demonstrating that integrated visualization, tissue modification, illumination and irrigation can be positioned at the distal end of an elongated member that has a 5.00 mm outer diameter.

FIG. 2C shows the cross-section of a distal end of elongated member that is analogous to that shown in FIG. 2A, with the exception that smaller non-circular cross-section guidewires (1.20 mm×0.60 mm) are present. As a result, light source 240 may have a 1.63 mm diameter and mechanical cutter 230 may have a 2.22 mm diameter. Like the embodiment shown in FIG. 2A, FIG. 2C is drawn to scale, demonstrating that integrated visualization, tissue modification, illumination and irrigation can be positioned at the distal end of an elongated member that has a 5.00 mm outer diameter.

FIG. 3A shows an example cross-section a distal end of a device according to an embodiment of the invention. FIG. 3A illustrates the distal end of a device 300 having a distal end outer diameter of 6.6 mm, where the drawing is to scale. The distal end of device 300 includes an integrated camera 320 (e.g., a CMOS sensor) having an outer diameter of 2.8 mm and two fiber optic light sources 330 each having an outer diameter of 1.3 mm. Also integrated at the distal end are electrode cutters 340 (having dimensions of 2.0 mm×0.7 mm) each associated with an irrigation lumen 350 (having dimensions of 1.2 mm×0.8 mm). In addition, the distal end includes central aspiration lumen 360 which has a rectangular configuration and dimensions of 5.0 mm×1.8 mm. In FIG. 3A, the integrated camera 320 is overlapping with other elements, which illustrates how the camera cross-section only occupies space at the most distal portion of the device 300. Overlapping portions of cross sections of other components, including the aspiration lumen 360, would be terminated or diverted laterally before reaching the proximal end of the camera. During use of the device for removal of tissue from a target tissue location, the following steps may be performed. First the distal end 300 of the device is introduced into the target tissue dissection region through access device 310. Access device 310 may be any convenient device, such as a conventional retractor tube. Access device 310 as shown in FIG. 3A has an inner diameter of 7.0 mm and an outer diameter of 9.5 mm. At this stage, orientation of camera 320 is biased to one side (left side in figure). During insertion, the electrode 340 on the side opposite the viewing field of the camera (right side in figure) is distally translated so that it emerges distally from the distal tip of the device 300. Also during insertion, the distally translated electrode 340 is activated by supplying RF current and irrigating conducting fluid, resulting in tissue dissection during insertion of the device. For further tissue dissection on the side to which the camera is biased (left side in figure), the electrode 340 on the same side as the viewing field of the camera (left side in figure) is distally translated so that it emerges laterally from the endoscope probe on the proximal side of the camera. While being translated, the same electrode (left side in figure) is activated by supplying RF current and irrigating conducting fluid, resulting in tissue dissection. At this point, the entire end of the device 300 may be translated proximally and distally until the desired tissue dissection is obtained. When finished with tissue dissection at the first location, the device may be rotated 180 degrees and further tissue removed using the steps described above.

Figure 3B:
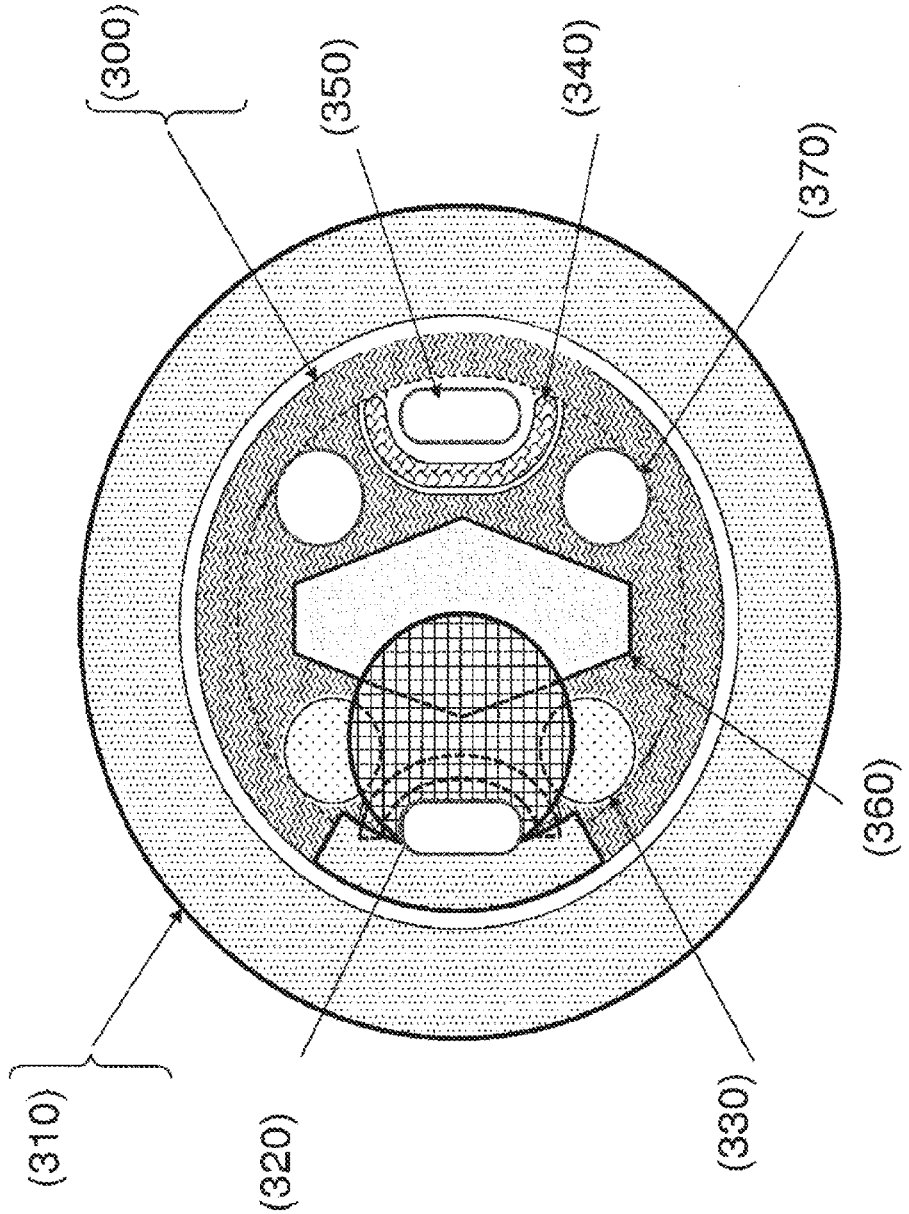

FIG. 3B shows an example cross-section of the distal end of a device 300 similar to that in FIG. 3A, except that it includes additional irrigation lumens 370 (outer diameter 1.2 mm) in addition to the irrigation lumens 350 (dimensions of 1.5 mm×0.9 mm) associated with the electrodes 340 (dimensions 2.5 mm×1.1 mm). Also, the geometry of the aspiration tube is hexagonal rather than rectangular to maximize use of space for this geometry (dimensions 4.2 mm×2.3 mm). The drawing is to scale, and shows another example of what can be integrated at the distal end of a device having a 6.6 mm outer. As shown, the cross section of the camera 320 is overlapping with other elements as in FIG. 3A, which shows how the camera cross-section only occupies space at the most distal portion of the device. Overlapping portions of other cross sections, including the light sources, one of the electrodes, and the aspiration tube, would be terminated or diverted laterally before reaching the proximal end of the camera. Operating this device may include the same steps as described above in connection with the device of FIG. 3A, except that additional irrigation could be used to help flush out dissected tissue and to clean the camera lens using the additional irrigation lumens 370.

FIG. 3C shows an example cross-section of the distal end 300 of a device similar to that in FIG. 3B, except that the orientation one of the electrodes 340 is reversed and the geometry of the aspiration tube 360 is trapezoidal rather than hexagonal to maximize use of space for this geometry. The drawing is to scale, and shows another example of components that can be integrated into a 6.6 mm outer diameter device distal end. In FIG. 3C, the dimensions of the components are the same as that of FIG. 3B, with the exception that irrigation lumens 370 have an outer diameter of 1.1 mm, the dimensions of aspiration lumen 360 are 4.2 mm×2.7 mm, the dimensions of electrodes 340 are 2.5 mm×11 mm and the dimensions of electrode irrigation lumens 350 are 1.5 mm×0.9 mm. As in the devices shown in FIGS. 3A and 3B, the camera cross section is overlapping with other elements, which shows how the camera cross-section 320 only occupies space at the most distal portion of the probe. Overlapping portions of other cross sections, including the light sources, one of the electrodes, and the aspiration tube, would be terminated or diverted laterally before reaching the proximal end of the camera 320. Operating this device may include the same steps as described above in connection with the device of FIGS. 3A and 3B.

Figure 3D:
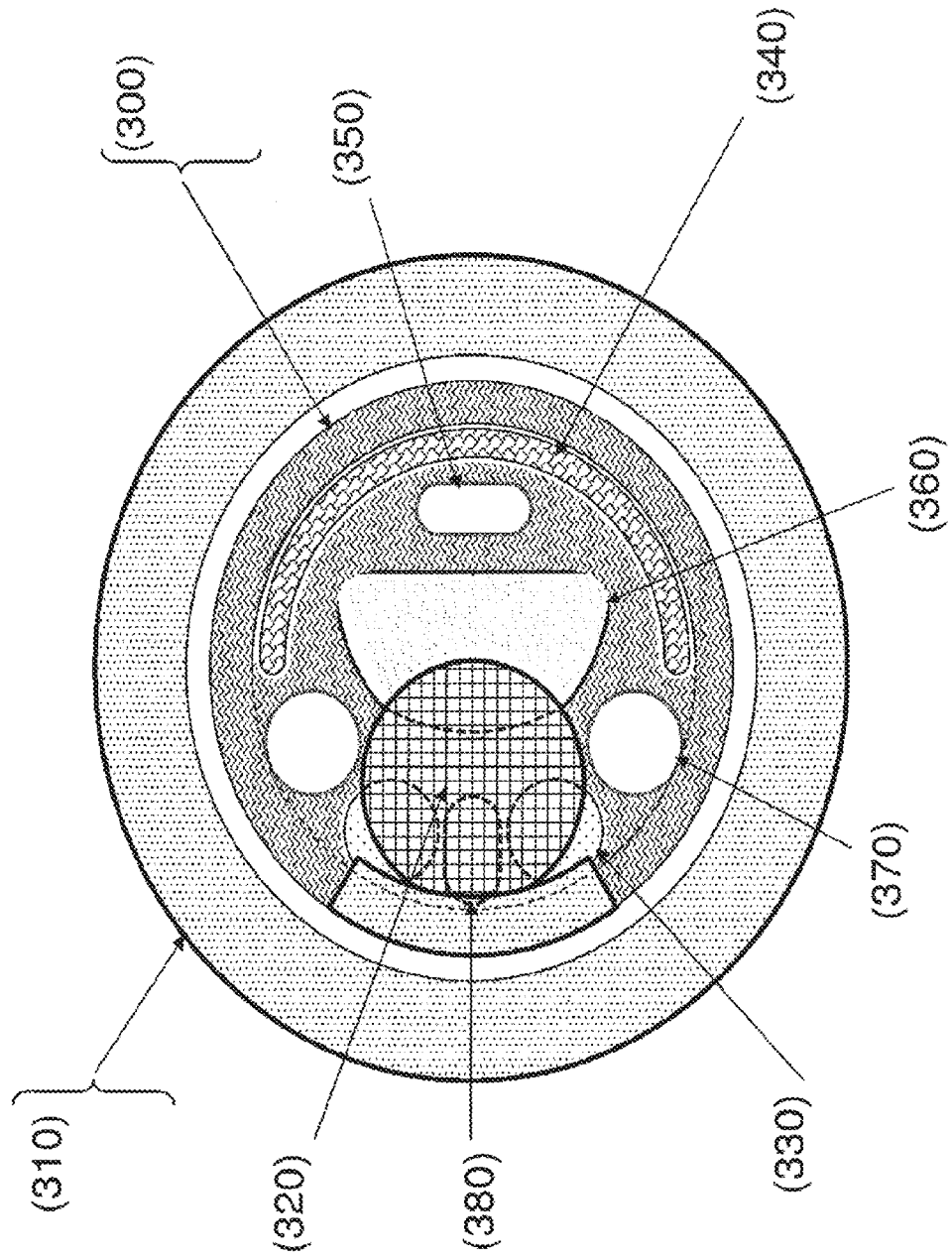

FIG. 3D shows an example cross-section of the distal end 300 of a device that is similar to that in FIG. 3C, except that only one electrode 340 (dimensions 5.4 mm diameter×0.35 mm thick) is used and it is much larger than the electrode present in the device shown in FIG. 3C. The electrode irrigation lumen is also dimensioned differently, having dimensions of 1.5 mm×0.6 mm. In FIG. 3C, integrated camera 320 is shown with camera cables 380 (having dimensions of (1.5 mm×0.8 mm). Also, the geometry of the aspiration lumen is a semi-circular rather than trapezoidal to maximize use of space for this geometry, where the dimensions of the aspiration lumen are 3.4 mm×2.1 mm. The drawing is to scale, and shows an example of the components that can be integrated at the distal end of a device that has a 6.6 mm outer diameter. The device is shown present in an access tube having a 7.2 mm inner diameter and a 9.5 mm outer diameter. In FIG. 3D, the camera 320 cross section is overlapping with other elements as in FIGS. 3A to 3C, demonstrating that the camera 320 cross-section only occupies space at the most distal portion of the probe. Overlapping portions of other cross sections, including the light sources and the aspiration tube, would be terminated or diverted laterally before reaching the proximal end of the camera. Operating this device may include the same steps as described above in connection with the device of FIGS. 3A to 3C, except that the single electrode serves the function of both electrodes in FIGS. 3A to 3C. The electrode is distally translated only a short distance for distal cutting, and then it is distally translated farther to cause it to extend laterally to the side viewed by the camera for tissue dissection on that side.

FIG. 3E shows an example cross-section of the distal probe tip similar to that in FIG. 3D, except that one of the irrigation channels is replaced by a probe tool 390, having an outer diameter of 1.2 mm, which is employed to manipulate tissue and expose target tissue regions for visualization and/or modification by a tissue modifier, such as the electrode device 340. The drawing is to scale, and shows another example of components that can be integrated at the distal end of a device having a 6.6 mm outer diameter. Operating this device may include the same steps as described above in connection with the device of FIGS. 3A to 3D, except that the probe is also available for probing the tissue dissection region and for assisting in desired tissue dissection.

FIG. 4 provides a side view of a device according to an embodiment of the invention, where the device includes a side-viewing integrated camera at its distal end.

In FIG. 4, device 400 includes integrated camera 410 having a side-viewing or biased lens 420, which provides a field of view which includes components from both the forward and side views of the device. As shown, the side-viewing camera is angled at a degree ranging from 15 to 65° relative to the longitudinal axis of the elongated member. Device 400 also includes an integrated tissue cutter 430 (e.g., in the form of an RF electrode) and integrated light source 435. Device 400 is shown in relation to intervertebral disc 440, where the distal end of the device 400 extends through the annulus fibrosis 450 into the nucleus pulposus 460.

Figure 5:
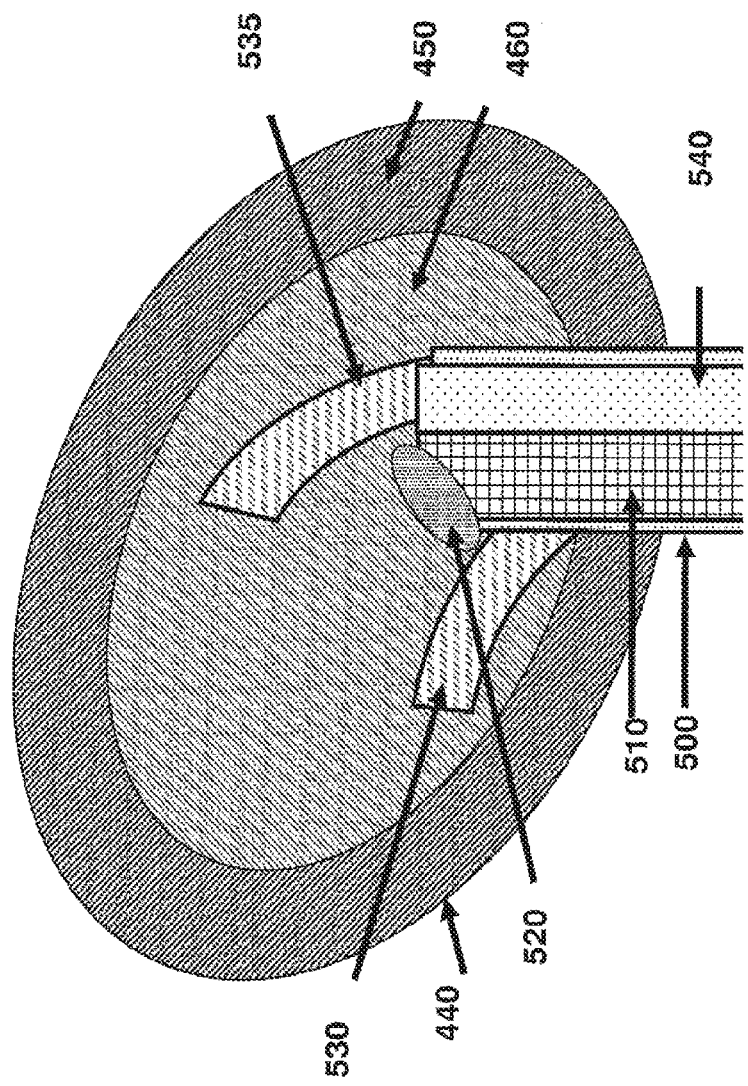
FIG. 5 provides an alternative view of the distal end of a device according to an embodiment of the invention, where the device is shown accessing the nucleus pulposus of an intervertebral disc.

FIG. 5 provides a side view of a device 500 according to an embodiment of the invention, where the device includes a side-viewing integrated camera 510 at its distal end and two steerable electrodes 530 and 535. In FIG. 5, device 500 includes integrated camera 510 having a side-viewing or biased lens 520. Device 500 also includes an integrated electrodes 530 and 535 which are steerable (e.g., being fabricated from a shape-memory material) and integrated light source 540. Device 500 is shown in relation to intervertebral disc 540, where the distal end of the device 500 extends through the annulus fibrosis 450 into the nucleus pulposus 460.

FIGS. 6A and 6B are isometric views of an embodiment of the distal end of a tissue modification device illustrating the invention inserted into the intervertebral disc space. The tissue modification device 600 includes an elongated member 610 inserted through the disc annulus 620 into the nucleus pulposus 630 of the intervertebral disc space. The tissue modification device 600 also includes an RF electrode 640 extended from the distal end of guidetubes 650, which are extended from the distal end of the elongated member 610. The guidetubes 650 are extended from the distal end of the elongated member 610 and have a curved shape, which facilitates access of the RF electrode 640 to the entire intervertebral disc space. The tissue modification device 600 also includes an integrated CMOS visualization element 660 at the distal end of the elongated member 610.

FIGS. 6A and 6B provide views of an RF electrode that is steerable at its distal end. In the embodiment depicted in FIGS. 6A and 6B, the steering functionality of the RF electrode is provided by a shape-memory element in conjunction with a guidetube. The term "shape-memory" as used herein refers to a material that can return to its original shape after being deformed. In certain embodiments, the shape-memory element comprises a shape-memory alloy, such as, but not limited to, a nickel-titanium (e.g., NITINOL) alloy, a copper-zinc-aluminum-nickel alloy, a copper-aluminum-nickel alloy, or the like. For example, the steering functionality of the RF electrode can be provided by wires comprising a shape-memory alloy. The shape-memory wires can be attached to the RF electrode such that when the RF electrode is extended from the distal end of the elongated member, the shape-memory wires take on a predetermined conformation, thus moving the RF electrode into substantially the same conformation. In certain cases, the shape-memory element is provided in conjunction with a guidetube. The guidetube can be a tube (i.e., a cylinder with a hollow central lumen) provided within the elongated member for housing the RF electrode and for guiding the direction of the RF electrode. Thus, the RF electrode can be provided within the central lumen of the guidetube. The guidetube can be composed of any convenient biocompatible material, such as plastic, rubber, metal, and the like. The guidetube can be provided with one or more shape-memory elements, such as wires comprising a shape-memory alloy, as described above. In certain embodiments, the guidetube is a shape-memory guidetube, such as a guidetube comprising a shape-memory alloy.

In some cases, the guidetube is slidably positioned in the elongated member, and may be extended from the distal end of the elongated member. In some cases, the shape-memory guidetube has a curved shape when extended from the distal end of the elongated member, such that the guidetube extends at an angle from the longitudinal axis of the elongated member. For example, when the guidetube is fully extended from the distal end of the elongated member, the guidetube may form an arc shape where the guidetube comprises an arc of 1° to 360°, such as 30° to 180°, including 60° to 120°. As described above, the guidetube can be provided with an RF electrode in the central lumen of the guidetube. In some instances, the guidetube is configured to facilitate the RF electrode's access to the entire intervertebral disc space. In certain instances, accessibility to the entire IVD space is facilitated by articulation of one or more of the RF electrode, the guidetube, and the elongated member. In addition, the RF electrode can be slidably positioned in the guidetube, and may be extended from the distal end of the guidetube. The elongated member, the RF electrode and/or the guidetube can be independently rotated, providing additional accessibility within the IVD space.

In certain embodiments, the tissue modification device includes two or more guidetubes, where the guidetubes are slideably translateable with respect to the elongated member. In some cases, the guidetubes are slideably translateable with respect to each other, which facilitates extending the RF electrode at an angle from the longitudinal axis of the elongated member or deforming the electrode tip into a new shape or configuration. Thus, one guidetube can be extended or retracted with respect to the distal end of the elongated member independent of the other guidetube(s). For instance, the movement of each guidetube can be controlled by the user, such that the user can extend, retract or steer each guidetube individually.

In some cases, the RF electrode comprises a wire slidably positioned in a shape memory guidetube that is slidably positioned in the elongated member. In certain instances, the RF electrode comprises an exposed portion positioned between first and second ends, where the first and second ends are each positioned in a shape-memory guidetube. By "exposed" is meant that a portion of the RF electrode is able to make electrical contact with the desired target tissue. In these cases, the first and second ends are linearly translatable, where the first and second ends are translatable in unison, such that the first and second ends can be extended and retracted from the distal end of the elongated member at the same rate. In other instances, the first and second ends are linearly translatable with respect to each other, such that the first and second ends can be extended and retracted from the distal end of the elongated member at different rates or to different positions of extension from the distal end of the elongated member. This facilitates the movement of the exposed portion of the RF electrode at an angle from the longitudinal axis of the elongated member. For example, when the RF electrode is extended from the distal end of the elongated member, the angle between the RF electrode and the longitudinal axis of the elongated member can be from 1° to 270°, such as 30° to 180°, including 60° to 120°.

Figure 6E:
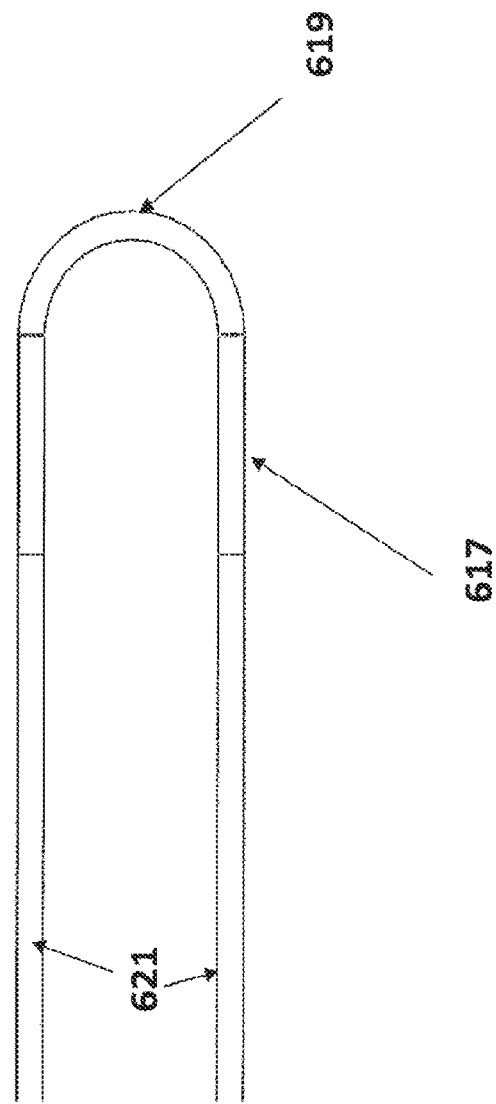

As shown in FIGS. 6A and 6B, the RF electrode 640 is a U-shaped structure that includes a distal cutting end (the exposed region), bounded on each side by a ceramic member. This U-shaped configuration is further illustrated in FIG. 6E. The ceramic members 617 flanking each side of the distal cutting end 619 may be joined (e.g., such that they have a cross-bar configuration as shown in FIGS. 6A and 6B) or be separate component from each other (e.g., as shown in FIG. 6E). These components may be fabricated from any convenient ceramic material, including but not limited to alumina, such as STEATITE™ alumina, MAECOR™ alumina, and the like. In FIG. 6E, the extended length of region 619 may vary, ranging from 2 to 20 mm, such as 2 to 10 mm and including 2 to 6 mm. The diameter of the wire making up region 619 may vary, and in certain embodiments is 180 um, such as 150 um or less, such as 130 um or less, such as 100 gm or less, such as 80 gm or less. While the distal cutting end or region 619 may be fabricated from a variety of materials, in some instances this portion of the electrode is fabricated from a material that is different from the material of the electrode wires 621. Materials of interest from which the distal cutting end 619 may be fabricated include, but are not limited to tungsten, tungsten alloys, e.g., tungsten rhenium, steel, tungsten coated with noble metals, such as Pt, Au, etc., and the like.

FIG. 6C provides a view of the distal end of device that is analogous to that shown in FIGS. 6A and 6B. FIG. 6C shows how a variety of components including an integrated CMOS visualization sensor 660, irrigation lumens 665, aspiration lumen 670, and steerable RF electrode 640 can be incorporated into the distal end of an elongated member having an outer diameter that is 7.0 mm or less, such as 6.5 mm or less.

Electrode 640 is made up of electrode wires extending from electrode guidetubes 650. Separating the electrode wires from the distal cutting end 690 are ceramic electrode crimp elements 680. Electrode wires 640 and guidetubes 650 are shown in an extended configuration in FIG. 6C but each independently may be fabricated from a shape memory material so as to assume a curved configuration (as shown in FIGS. 6A and 6B) and therefore impart steerability to the RF electrode. As shown in FIG. 6C, aspiration lumen 670 opens to the side of the device 600 and is positioned just proximal of the CMOS visualization sensor 660 so that all of the disparate components may be integrated at the distal end of the device.

FIG. 6D provides a three-dimensional view of one embodiment of a distal end of tissue modification device 600 (having a 6.5 mm outer dimension) of the invention. In FIG. 6D, the distal end of the device includes and integrated circular CMOS visualization sensor 605 and integrated LED 610. Also shown is a first forward facing irrigation lumen 615 and a second irrigation lumen 617 which is slightly extended from the distal end and is side facing so that fluid emitted from lumen 617 is flowed across CMOS visualization sensor 605 to clean the sensor of debris, when needed. Also shown is an aspiration lumen 625 positioned proximal the irrigation lumens 615 and 617 and integrated CMOS visualization sensor 605, where the aspiration lumen 605 is configured to aspirate fluid and tissue debris from a target tissue site during use. The distal end further includes an integrated steerable RF electrode assembly 655. RF electrode assembly 655 includes NITINOL shape memory guide tubes 645 extending from insulated (e.g., RF shielded) guide lumens 642. The RF electrode further includes a tungsten cutting wire 665 joined at each end to a NITINOL shape memory electrode wire 663 by a ceramic arc stop 675. As shown, the diameter of the cutting wire 665 is smaller than the diameter of the electrode wires 663, where the difference in size may vary and may range from 100 to 500 um, such as 300 to 400 gm.

Figure 7:
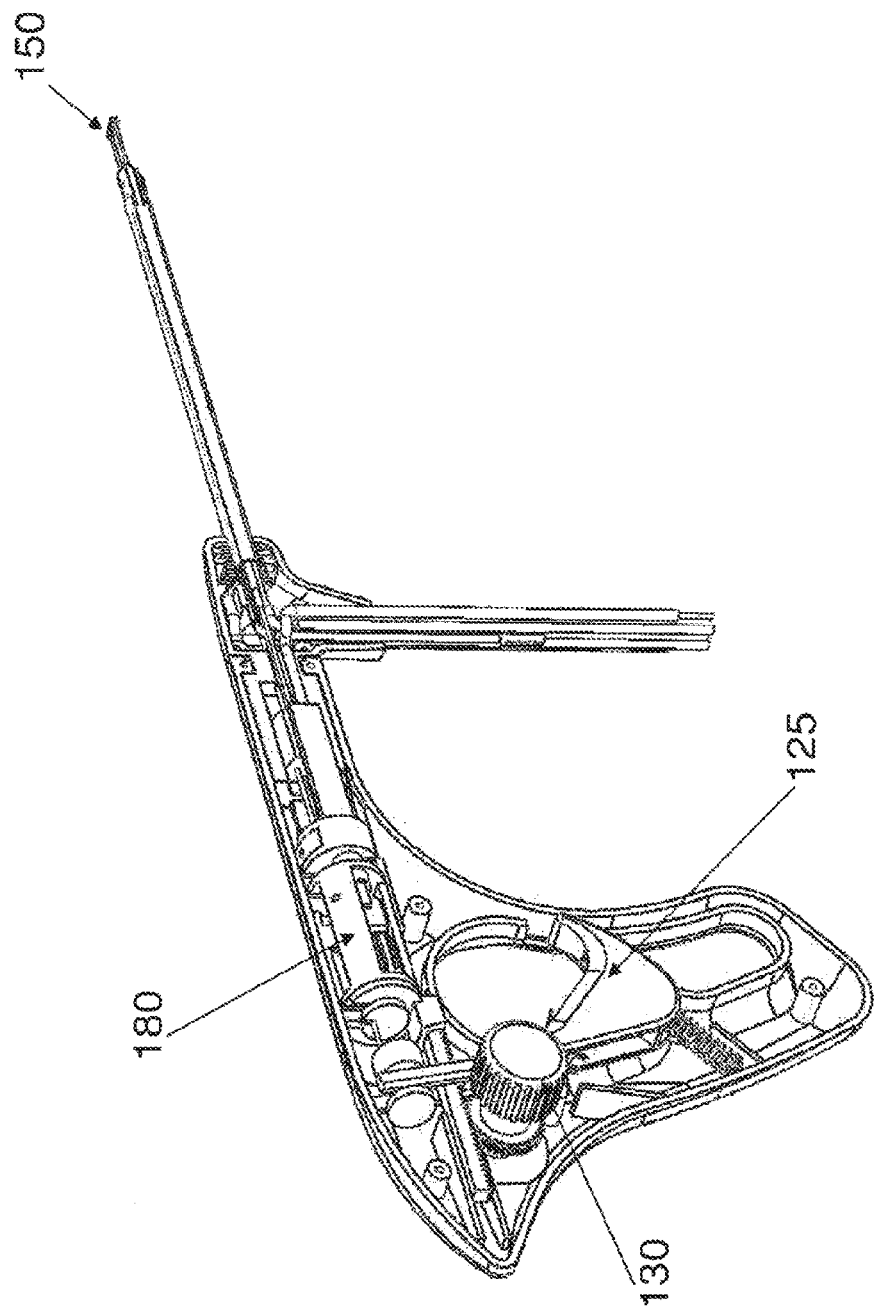
FIG. 7 provides a cutaway view of the device shown in FIGS. 1A and 1B.

FIGS. 1A and 1B, reviewed above, provide different views of a device according to an embodiment of the invention, where the device includes a distal end as shown in FIG. 6D. FIG. 7 provides a cutaway view of the devices shown in FIGS. 1A and 1B. As shown in FIG. 7, the device includes trigger element 125 which translates the guidetubes relative to the distal end of the elongated member. Also shown is thumbwheel 130 which provides for manual movement of the electrode relative to the distal end. The cutaway view of FIG. 7 shows mechanical actuator 180 which provides for linear translation of electrode 150 positioned at the distal end of the elongated member.

Figure 19:
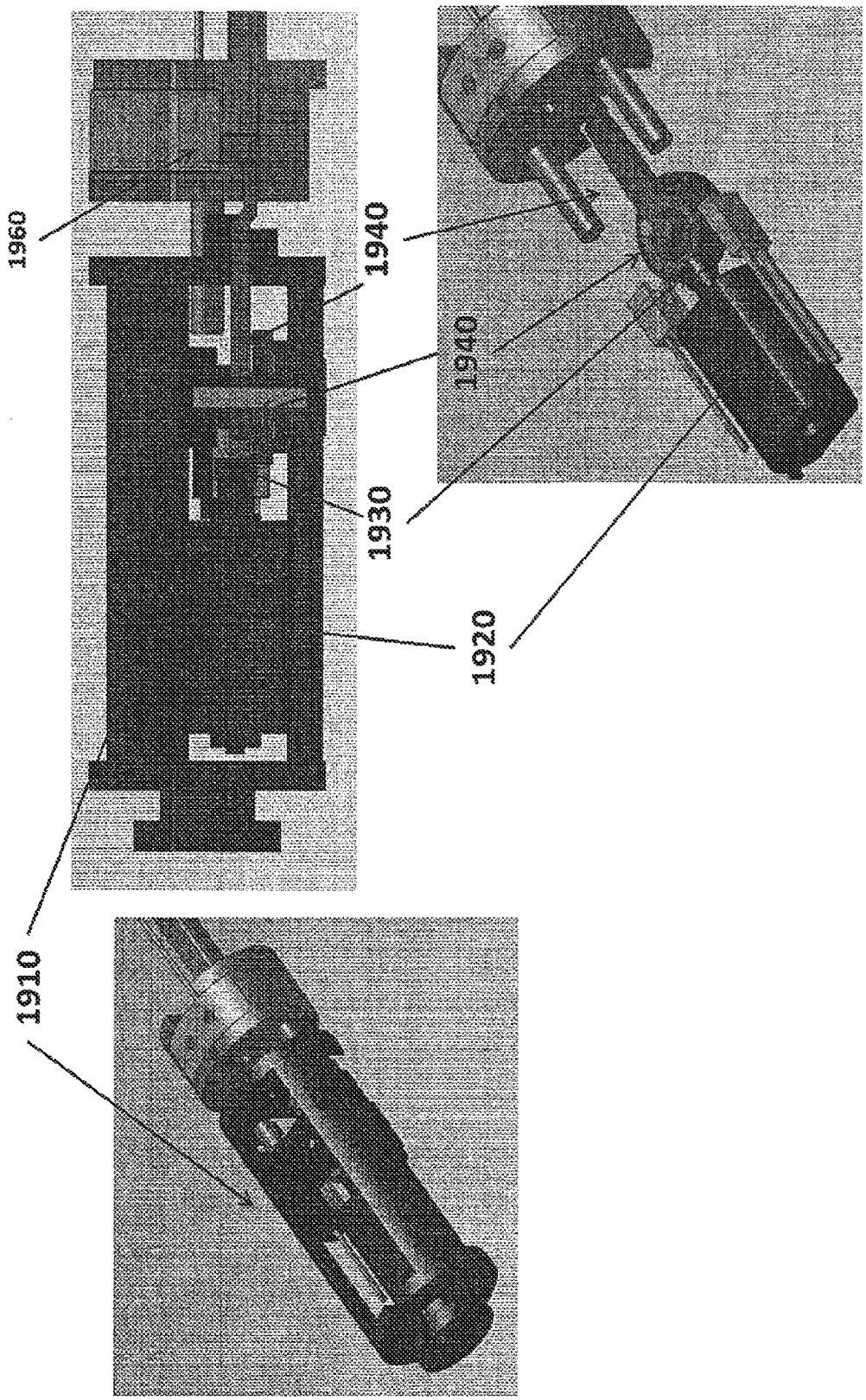
FIG. 19 provides various views of an electric motor linear actuator that may be present in devices of the invention to provide for linear translation of the RF electrode, according to an embodiment.

As described generally above, certain embodiments of devices of invention include linear mechanical actuators, e.g., as described in U.S. patent application Ser. No. 12/467,122, the disclosure of which is herein incorporated by reference. FIG. 19 provides various views of an electric motor linear actuator that may be present in devices of the invention to provide for linear translation of the RF electrode. As shown in FIG. 19, the device includes a motor carriage 1910 that houses an electric motor 1920. Electric motor 1920 includes small bevel gear 1930 which is in operative relationship with large bevel gear 1940. Large bevel gear 1940 is, in turn, operatively connected to cam follower 1950 which is operatively connected to the RF electrode at transmission point 1960.

Systems

Aspects of the subject invention include tissue modification systems, where the systems include a tissue modification device, e.g., as described above, operatively connected to one or more extra-corporeal control units (i.e., extra-corporeal controllers). Extra-corporeal control units may include a number of different components, such as power sources, irrigation sources, aspiration sources, image data processing components, image display components (such as monitors, printers, and the like), data processors, e.g., in the form of computers, data storage devices, e.g., floppy disks, hard drives, CD-ROM DVD, flash memory, etc., device and system controls, etc.

Figure 8:
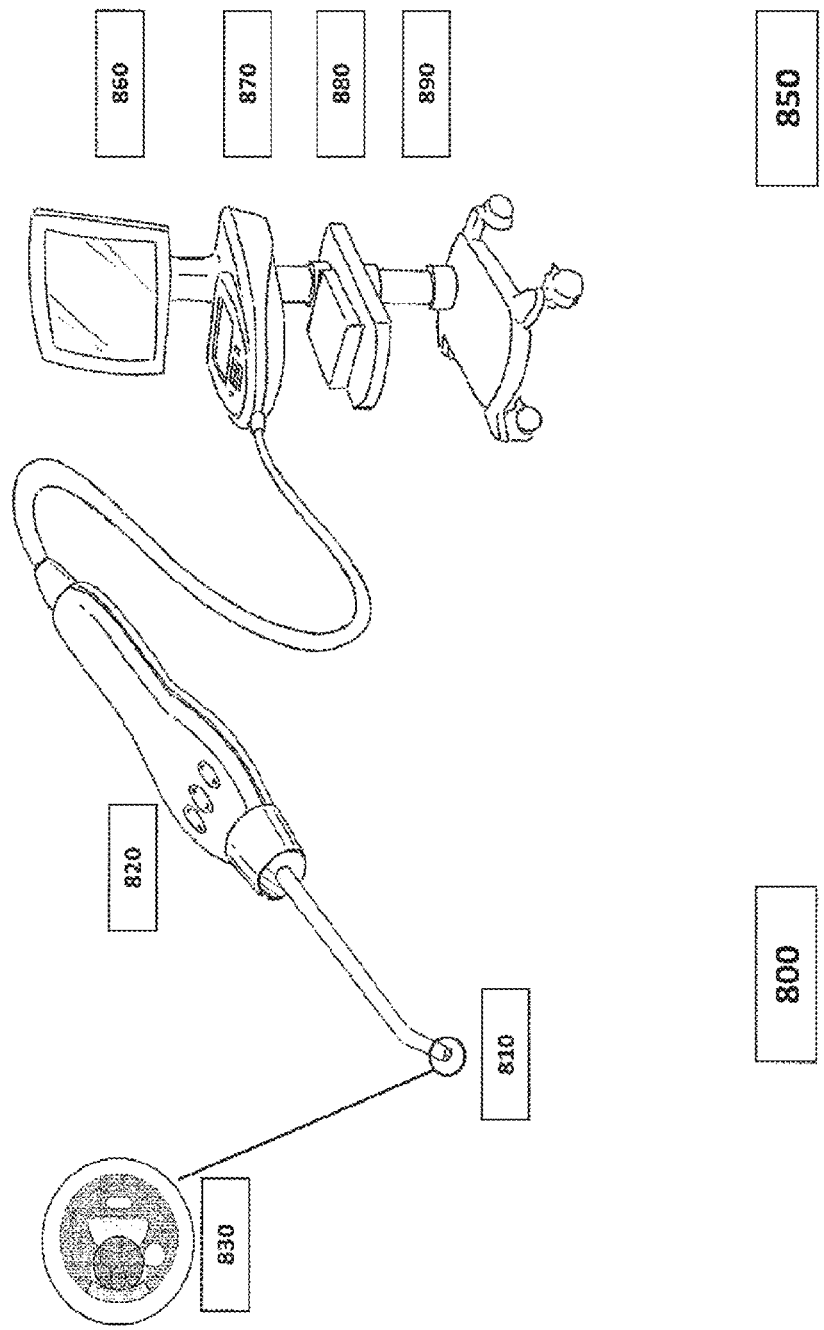
FIG. 8 provides a depiction of a system according to one embodiment of the invention, where the system includes both a disposable tissue modifier device and an extracorporeal control unit.

An example of a system according to an embodiment of the invention is shown in FIG. 8. In FIG. 8 the system includes hand-held tissue modification device 800 and extra-corporeal control unit 850. Hand-held device 800 includes distal end 810 and handle 820 configured to be held in the hand of an operator. Positioned at the distal end 810 are the integrated visualization and tissue modification components (as well as other components), as shown by cross-section 830. Extra-corporeal control unit 850 includes image display 860 (e.g., a liquid crystal display monitor), video digital signal processor 870, energy source 880 (e.g., configured to operate an RF tissue modification member) and irrigation/aspiration system 890. The hand-held device 800 and extra-corporeal control unit 850 are operatively connected to each other by a cable.

Figure 9:
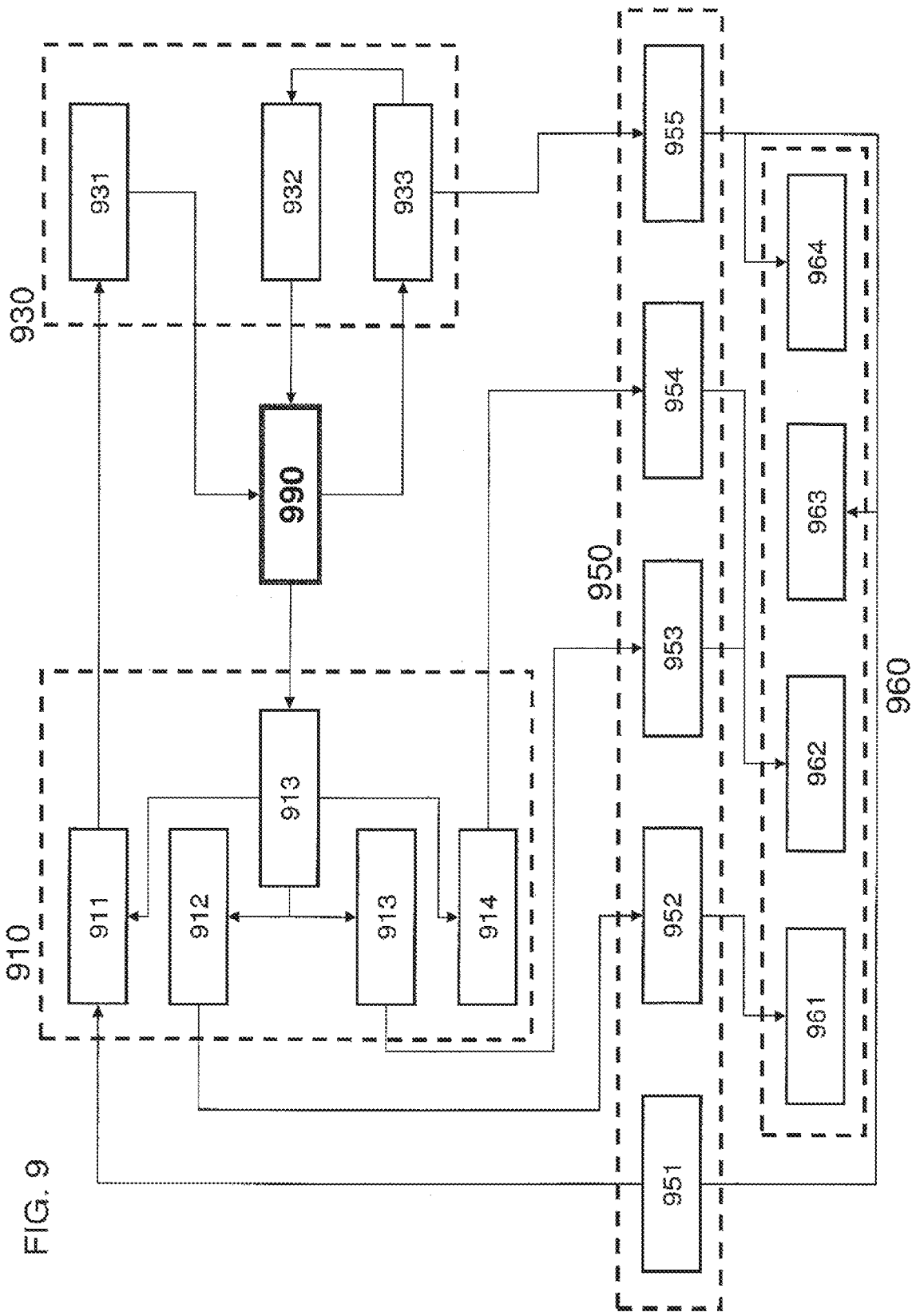
FIG. 9 provides a block diagram showing the architecture of a system according to one embodiment of the invention and how that system interacts with a user.

FIG. 9 provides a diagrammatic view of the architecture of a system according to one embodiment of the invention and how the various components of the system may interact with a user, such as a surgeon, during use. In FIG. 9, extra-corporeal control unit 910 includes a video processing unit 911, an RF electrode power source 912, an irrigation source 913 and an aspiration source 914. Each of these components is operatively connected to electrical controls 915, with which the user 990 may interact to operate the system as desired. Also shown is tissue modification device 950 which includes an integrated visualization sensor 951, an RF electrode 952, an irrigation lumen 953, an aspiration lumen 954 and an articulation mechanism 955. The tissue modification device 950 provides a number of functionalities 960, including tissue dissection 961, tissue removal 962, tissue discrimination 963 and accessibility 964. The system provides numerous user interface opportunities 930; including image display 931, tactile feedback 932 and mechanical controls 933.

Within a given system, the integrated distal end visualization sub-system may have a variety of different configurations. FIG. 10 provides an example of an embodiment of an integrated visualization sub-system that includes a distal end CMOS visualization sensor. As shown in FIG. 10, visualization sub-system 1000 includes distal end CMOS visualization sensor 1010 that includes lens housing 1015 component operatively coupled to integrated circuit component 1020. As shown in the figure, lens housing 1015 includes a lens set 1016. Also shown at the distal end is LED 1018 which provides illumination for a target tissue location during use. Integrated circuit component 1020 includes CMOS sensor integrated circuit 1021 and rigid printed circuit board 1022. The sub-components of lens housing/light source component 1015 are operatively coupled to flexible cable 1030 which provides for operative connection of the CMOS visualization system at the distal end of the device via the handle 1040 to the video processing sub-system 1050. In the handle 1040 the flexible cable operatively connects to a shielded cable 1052 which provides for RF isolation. As shown in FIG. 10, the various components are shielded from RF, e.g., by coating the elements with a conductive material which is then connected to a ground. For example, lens housing 1015 and cable 1030 are RF shielded. RF shielded cable 1052 connects to video processing sub-system 1050 which includes a variety of functional blocks, such as host controller 1051 (coupled to PC 1061), digital signal processor 1054 (coupled to LCD 1062) and CMOS visualization sensor bridge 1053. As shown in FIG. 10, video processing sub-system 1050 is ground to earth 1072 by connection to metal case 1070.

Systems of the invention may include a number of additional components in addition to the tissue modification devices and extra-corporeal control units, as described above. Additional components may include access port devices; root retractors; retractor devices, system component fixation devices; and the like; etc. Of interest are systems that further access devices as described in co-pending U.S. application Ser. Nos. 12/269,770; 12/269,772; and 12/269,775; the disclosures of which are herein incorporated by reference.

Figure 16:
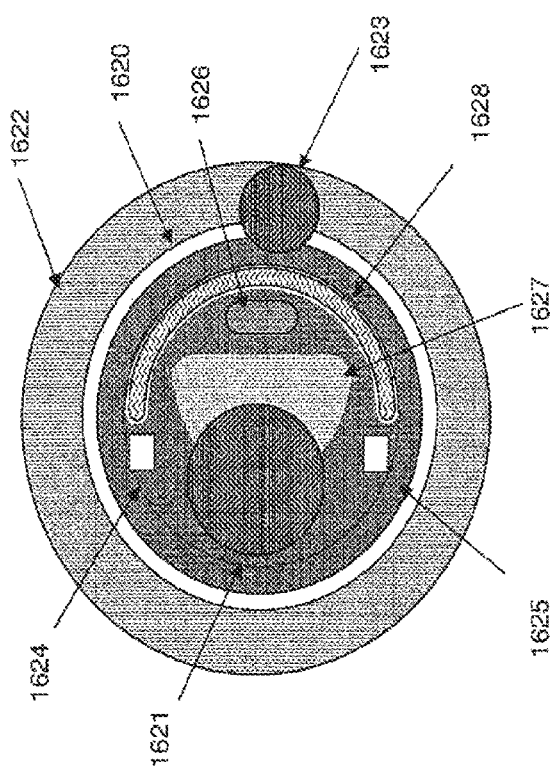
FIG. 16 provides a cross-sectional view of the distal ends of an elongated member of a minimally invasive tissue modification device and an access device, according to one embodiment.

As reviewed above, some embodiments of the invention include systems which include an access device. In such embodiments, two or more visualization elements may be distributed among the distal ends of the elongated member and the access device. FIG. 16 provides a cross-sectional view of the distal ends of an elongated member of a minimally invasive tissue modification device and an access device, according to one embodiment. In FIG. 16, distal end of elongated member 1620 includes first imaging sensor 1621 while distal end of access device 1622 includes a second imaging sensor 1623. Also shown at the distal end of elongated member 1620 are first and second I-EDS, 1624 and 1625. Also shown is an irrigation lumen 1626 and aspiration lumen 1627. In addition, the device includes a tissue modifier in the form of a dissection electrode 1628 (e.g., RF electrode). In the system shown in FIG. 16, the first imaging sensor 1621 provides visualization of the target tissue site. The second imaging sensor 1623 is positioned on an access device (although it could be positioned at a variety of locations on the access device or the elongated member). The orientation of second imaging sensor 1623 is such that imaging sensor 1623 provides imaged data of the elongated member, e.g., of the distal end of the elongated member during placement, etc. Any convenient positioning as use may be achieved.

Figure 17:
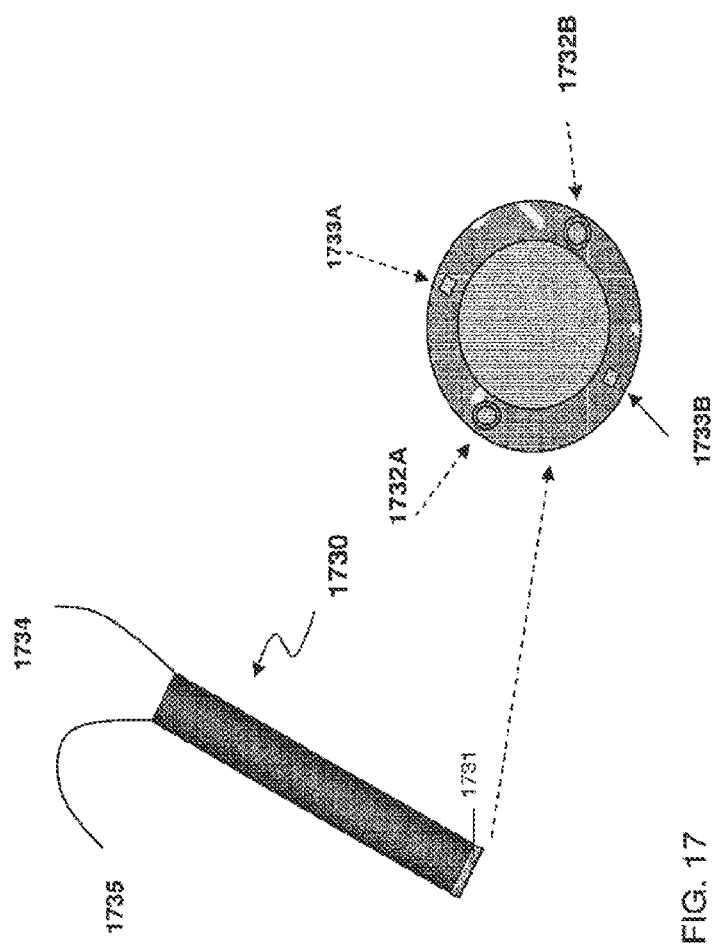
FIG. 17 provides different views of an access device, according to an embodiment.

FIG. 17 provides different views of an access device according to an embodiment. As shown in FIG. 17, access device 1730 includes a distal end 1731. Positioned at distal end 1731 are two cameras 1732A and 1732B and two illumination sources, e.g., LEDs or light fibers, 1733A and 1733B. Running the length of the access device and exiting the proximal end are wires 1734 and 1735 for provide power and control to the cameras and visualization elements, e.g., via coupling to a control device.

Figure 18:
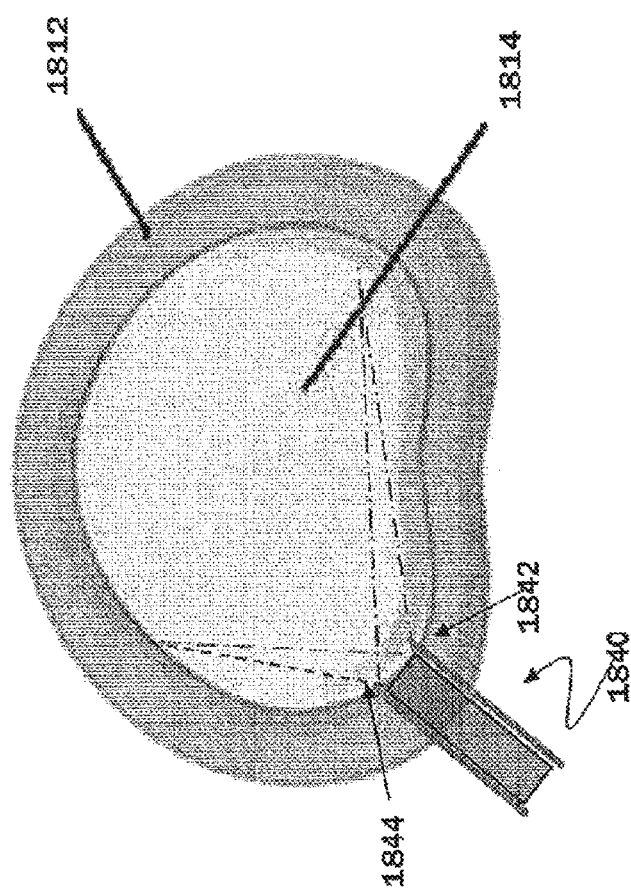
FIG. 18 provides a device having two cameras positioned in the same cross-section of the distal end of the device, according to an embodiment.

The multiple visualization and/or illumination elements of the devices may be positioned relative to each other in a variety of different ways. By selective positioning of these elements coupled, as desired, with specific image data processing techniques, unique views of the target tissue site may be obtained. For example, as illustrated in FIG. 18, two cameras 1842 and 1844 may be positioned in the same cross-section of the distal end of an imaging device 1840 (e.g., a minimally invasive tissue modification device and/or access device). Image data from the two cameras can, in such an embodiment, be combined to obtain a panoramic view of the target tissue site, in this case the nucleus pulposus 1814, within the annulus fibrosis 1812. This configuration also allows one to obtain a stereoscopic view of the target tissue site, e.g., by synchronizing the image data from the two cameras.

Placement of the visualization elements in different cross sections of the devices and/or on different devices can also provide for advantages in imaging. For example, FIG. 16 provides an illustration of a distal end of a system made up of a minimally invasive tissue modification device slidably positioned within an internal passageway of an access device, such as a retractor tube. In the embodiment depicted in FIG. 16, the primary camera 1621 is on the cross section of the tissue modification device, and the secondary camera 1623 is on the wall of the access device. Both cameras can be arranged to have certain orientations, as desired, such as forward viewing or angled or side viewing. Illuminations can also be arranged such that different views of the same object can be revealed. For example, the light source can be somewhat collimated or focused in a certain direction to give a better view of the surgical blades, electrodes or the local tissue appearance.

Image Processing Modules

Embodiments of devices and systems of the invention may include one or more different types of image processing modules. In some instances, devices of the invention may include a stereoscopic image module including one or more visualization sensors at a distal end. By stereoscopic image module is meant a functional module that provides a stereoscopic image from image data obtained by the device. As such, the module provides a user via the monitor with the perception of a three-dimensional view of an image produced from the image data obtained by the device. The module is described in terms of "images", and it should be understood that the description applies equally to still images and video. The device may include two or more distinct visualization sensors or a single visualization sensor via which the image data is collected and employed by the stereoscopic image module to provide the stereoscopic image. Where the elongated member includes first and second visualization sensors, the stereoscopic imaging module is configured to process imaged data provided by the first and second visualization sensors to produce the stereoscopic image.

In such embodiments, any convenient stereoscopic image processing program may be employed. FIG. 11 illustrates a block flow diagram of a technique to produce stereoscopic images from image data, according to one embodiment. Left and right image data are obtained (as represented by blocks 1105), either sequentially from a single visualization sensor that is moved from a first position to a second position or, if two visualization sensors are present, sequentially or simultaneously. The left and right Image data account for the different locations and perspectives associated with each respective position of the same visualization sensor or respective positions of the two distinct visualization sensors. The image data for the first and second images may include distortions, and an algorithm may be employed, for example, in which the left and right image data are first warped as shown via a calibration element to remove lens distortion, as represented by blocks 1110. Any convenient algorithm may be employed. Algorithms of interest include those described in "Geometric Calibration of Digital Cameras through Multi-view Rectification" by Luca Lucchese (Image and Vision Computing, Vol. 23, Issue 5, May 2005, pp. 517-539); and Levenberg-Marquardt algorithm, "Correction of Geometric Lens Distortion through Image Warping" by Lucchese (ISPA 2003, Proceeding of the 3rd International Symposium on Image and Signal Processing and Analysis, 18-20 Sep. 2003, Vol. 1, pp. 516-521). The resultant undistorted left and right images, represented by blocks 1115, are then processed with stereo and image fusion algorithms to construct a stereoscopic image, as represented at blocks 1120, 1122, 1124, 1126, 1128. Any convenient stereo and image fusion algorithms may be employed, such as but not limited to those described in: "Scene Reconstruction from Multiple Cameras" by Richard Szeliski (Microsoft Vision Technology Group; see also, http://research,,mäcrosoft.com/pubs/75687/Szeliski-ICIP00.pdf); "A parallel matching algorithm for stereo vision", by Y. Nishimoto and Y. Shirai (IJCAI-1985-Volume 2, pg. 977; see also, http://jcai.org/Past%20Proceedings/IJCAI-85.VOL2/PDF/059.pdf); "Image Fusion Using Wavelet Transform", by Zhu Shu-long (Institute of Surveying & Mapping; Commission Working Group IV/7; see also, http://www.isprs.org/commission4/proceedingsC2/pdfpapers/162.pdf); "Disparity field and depth map coding for multiview 3D image generation", by D. Tzovaras (Image Communication, Signal Processing; 1998, vol. 11, no. 3, pp. 205-230); etc.

Stereo algorithms compute range information to objects seen by the visualization sensors by using triangulation. Objects seen at different viewpoints will result in the object at different locations in the image data for the first and second visualization sensors. The disparity, or image difference, is used in determining depth and range of objects. Corresponding pixel points within the image data for the first and second visualization sensors may be identified and used in the determination of disparity line, as represented by block 1124. Because the first and second visualization sensors are at different locations and hence have different perspectives, the same object present in image data for the first and second visualization sensor may be at different pixel coordinate locations. Triangulation may be implemented, as represented by block 1126, based on geometry associated with the locations of the first and second visualization sensors may be used to determine depth and range of objects seen by the visualization sensors. Triangulation computations are applied to derive range data, and the resultant range (or depth) map can be overlayed on the image display, as desired. This is represented at block 1128 in FIG. 11. Stereoscopic images taking into account three-dimensional depth information can thus be reconstructed from image data from the first and second visualization sensor.

FIG. 12B illustrates slightly offset visualization positions, according to certain embodiments. FIG. 12B illustrates two visualization sensors, i.e., 1242 for a first view of objects A and B and 1244 for a second view of objects A and B. The depth and range of the object is found in a similar manner as for FIG. 12A, as described below. Further details regarding aspects of stereoscopic image modules that employ image data obtained by two or more distinct visualization sensors may be found in U.S. application Ser. No. 12/269,770; the disclosure of which is herein incorporated by reference.

Also of interest are stereoscopic image modules that are configured to provide a stereoscopic image from data obtained by a single image sensor. In such embodiments, the image sensor is configured to provide to the stereoscopic image module consecutive offset image data of the target tissue location, which consecutive offset image data are then employed by the stereoscopic image module to provide the desired stereoscopic image. By consecutive offset image data is meant image data that includes at least data from a first view of a target tissue location and data from a second view of the same target location, where the second view is offset from the first view. The second view may be offset from the first view by any convenient distance, for example 1 mm or less, including 0.5 mm or less. The first and second offset views may be obtained using any convenient approach. In one approach, the single visualization sensor is moved from a first position to a second position in order to obtain the desired offset image data. The single visualization sensor may be moved from the first to the second positions using any convenient manner, e.g., by a mechanical element that physically moves the sensor from the first to the second position. In yet other embodiments, the desired offset views may be obtained with a single visualization sensor operatively coupled to an optical guide system (which may include one or more of lenses, mirrors, filters, etc.) configured to provide the desired first and second offset views. For example, the first and second offset views may be provided to the single visualization sensor by including a first and second lens systems which alternately convey image data to the visualization sensor. The offset views may also be provided, for example, by including a single lens system with mirrors configured to provide the lens with two or more different views. The frequency with which the first and second offset views are obtained may vary, where in some instances the frequency may range from 1 to 30 frames/sec, such as 1 to 15 frames/sec. Various systems may be implemented to provide multiple views with a single camera. Systems of interest include, but are not limited to, those described in: "Scalable Multi-view Stereo Camera Array for Real World Real-Time Image Capture and Three Dimensional Displays" by S. Hill (Massachusetts Institute of Technology, Program in Media Arts and Sciences School of Architecture and Planning; May 7, 2004; see also, http://web.media.mit.edu/~vmb/papers/hillms.pdf); "Single Camera Stereo Using Planar Parallel Plate" by Chunyu Gao, et al. (Beckman Institute, University of Illinois at Urbana-Champaign; see also, http://vision.ai.uiuc.edu/newpubs/Stereo PPP Gao.pdf); and, "3-D Reconstruction Using Mirror Images Based on a Plane Symmetry Recovering Method" by Mitsumoto, H., et al. (IEEE Transaction on Pattern Analysis and Machine Intelligence; Vol. 14; Issue No. 9, September 1992, pp. 941-946).

FIG. 12A illustrates a single visualization sensor 1205 which is moved to two different positions (1201 and 1202) to sequentially obtained image data, which sequentially obtained image data is employed by a stereoscopic image module to produce a stereoscopic image of objects A and B. The first and second visualization positions 1201 and 1202 are at an offset width W from one another, which may vary, ranging in some instances from 1 mm or less, such as 0.5 mm or less. Objects A and B located at a focal plane distance Z are seen at different perspectives for the first and second positions (shown by dotted lines 1215, 1220, respectively). The difference in viewing perspectives is reflected in the image data obtained by the single image sensor from the first and second positions. As shown, first visualization sensor 1205 sees objects A & B off to the right of center when in position 1201 and sees objects A and B off to left of center when in position 1202. The disparity between the two views is used to determine depth and range of objects A and B.

Figure 13:
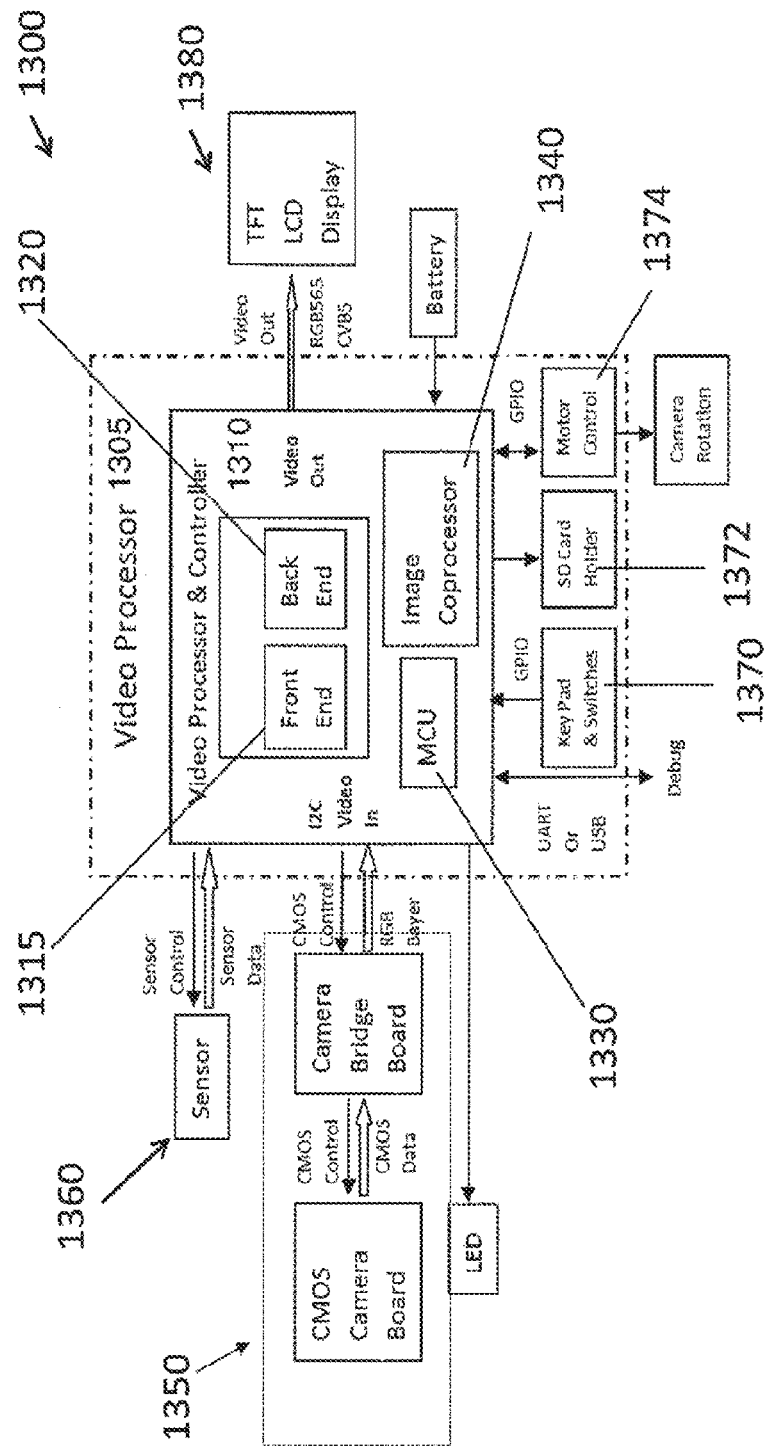
FIG. 13 provides a functional block diagram of a portion of a system including a video processor module, according to one embodiment.

The stereoscopic image module may be implemented in a video processor module configured to receive image data obtained by the one or more visualization sensors. The stereoscopic image module processes the image data to provide stereoscopic image data for display on a display. FIG. 13 illustrates a functional block diagram of a portion of the system 1300 including a video processor module 1305, according to one embodiment. Video processor module 1305 includes a processor/controller module 1310 which is in communication with sensor module 1360, camera module 1350, and display 1380. Processor/controller module 1310 comprises front end module 1315, back end module 1320, microcontroller 1330, and image coprocessing module 1340. Image coprocessing module 1340 includes, for example, stereoscopic image module and performs the previously described functions and operations of the stereoscopic image module.

Camera module 1350 may include a single visualization sensor, or two or more distinct visualization sensors which provide image data. Front end module 1315 includes circuitry for receiving the image data from the camera module 1350. The image data received from camera module 1350 is processed by stereoscopic image module (i.e., by image coprocessing module 1340) to provide stereoscopic image data. For example, as previously described, the image data from each distinct visualization sensor may be warped to correct image distortion, and fused to construct a single stereo image taking into account three-dimensional depth information. Back end module 1320 includes circuitry for sending the stereoscopic image data to display 1380. Display 1380 displays a three-dimensional view of the image data for the user to see.

Video processor module 1305 may be electrically coupled with camera module 1350 via an I2C bus, for example, with camera module 1350 configured as the slave and microcontroller 1330 as the master. Microcontroller 1330 may be configured to send camera control data to the camera module 1350. The camera control data may comprise information requests (e.g., for information relating to testing/debugging, for calibration data, etc.) or provide commands for controlling the camera module 1350 (e.g., controlling the two or more distinct visualization sensors, etc.).

Sensor module 1360 may include one or more sensors and/or tools previously described. The one or more sensors and/or tools implemented may provide sensor data related to their specific function and application. The sensor data is received by processor/controller module 1310 and may be used in a variety of ways depending on the specific function of the sensor(s) and/or tool(s) and their application. For instance, sensor data may be used by processor/controller module 1310 to provide information to a user (e.g. parameter data, calibration data, measurement readings, warnings, etc., to be displayed on display 1380 or to illuminate one or more I-EDS), to account for feedback signals for more accurate control of a specific sensor(s) and/or tool(s), to store in memory, to further process into additional related information, etc. Microcontroller 1330 may also control the sensor module 1360 via the I2C bus or General Purpose Input/Output (GPIO) interface by sending sensor control data (e.g., to control and/or calibrate the specific sensors and/or tools implemented).

Processor/controller module 1310 further comprises various modules for interfacing with external devices and peripherals. For example, as shown in FIG. 13, processor control module includes a key pad and switches circuitry 1370 for receiving input signals from the user key pad and switches on the device; SD card holder circuitry 1372 for sending/receiving data stored in memory devices, and motor control circuitry 1374 for controlling the camera rotation. Microcontroller 1330 may be configured with, for example, a GPIO to communicate with the various circuitry. Furthermore, the video processor module 1 305 may include a communication interface for implementing testing or debugging procedures—e.g., UART, USB, etc.

The visualization systems discussed above may include image processing components that manipulate image data in some fashion, e.g., to refine the data, the obtain information from the data, to take one or more actions based on the obtained information, etc. The image processing components may be physically embodied in any convenient part of the system, e.g., in an extra-corporeal processing unit, in a minimally invasive device, etc. It should be understood that while the image processing components are described herein primarily with respect to minimally invasive tissue modification devices having image processing components (or communicating with devices having image processing components), other minimally invasive devices may also implement image processing components (or communicate with devices having image processing components).

Additional details regarding stereoscopic image processing modules are provided in U.S. application Ser. Nos. 12/269,770 and 12/501,336; the disclosures of which are herein incorporated by reference. It should also be understood that while the stereoscopic image module is described herein primarily with respect to minimally invasive tissue modification devices having an integrated tissue modifier at the distal end, other minimally invasive devices may also implement a stereoscopic image module of the invention, where such devices may include a distal end integrated tissue modifier and yet still come within the scope of these embodiments of the invention.

In some embodiments, an image processing module that compares image data to a reference may be present. The image processing modules of these particular embodiments are processing modules that are configured to receive image data and compare the received image data with a reference that includes at least one of color descriptor data and anatomical descriptor data to make a determination as to whether an alert signal should be generated.

The image data that is received by the image processing module may vary. In certain instances the image data is a data obtained from a visualization sensor. The received image data may be data for one or more still images, or video data. Accordingly, the image data may be used by the image processing component to produce and output still images or video. When the image data is video data, the image processing module may be configured to perform its functions in real-time, such that the image processing module is configured to process the video data in real-time. The term "real-time" is used in the conventional sense to mean that the image processing module compares the received image data with the reference at the same rate as the image data is received.

In certain embodiments, the received image data includes a comparator component. The comparator component is a component that may be employed to compare the received image data with the reference (where the reference is described in greater detail below). This comparator component may be any convenient data component that allows the received image data to be accurately compared with data for one or more images of the reference. While any convenient comparator component may be employed, in certain instances the comparator component is made up of one or more predetermined fiducial elements in the image. The one or more predetermined fiducial elements in the image may be virtual points or actual structures which are present in the image. In either case, the fiducial element, based on its location in the image, may be at a known position in the image relative to the visualization sensor that is employed to obtain the image. As such, where the fiducial element is a virtual point, the virtual point may be a point in space in the image that is calculated relative to the visualization sensor that obtains the image. Any convenient protocol for determining this virtual fiducial element may be employed. Alternatively, where the fiducial element is an actual structure in the image, the actual structure in the image may be a structure of the device that appears in the image and is at a known position relative to the visualization sensor of the device.

In some instances, the fiducial element of the one or more images of the received image data is an actual structural element of the device that is employed to obtain the image data. The structural element of the device may be any device component that appears in the image obtained by the visualization sensor. In some instances, the structural element serves no purpose other than to be the fiducial element in images obtained by the visualization sensor. For example, the structural element may be a wire or analogous structure that projects from the distal end of the device into the field of view of the visualization sensor and is therefore captured in the image data obtained by the visualization sensor. In yet other embodiments, the structural element serves one or more purposes other than just as the fiducial element of the image. For example, the structural element may be a tissue modifier, such as a RF electrode, e.g., as described in greater detail below. In these embodiments, the structural element serves one or more additional functions, such as tissue modification. Any structure of the device that is in the field of view of the camera may serve as the structural element and therefore as the fiducial element.

As summarized above, the image processing module is configured to compare the received image data with a reference. The term "reference" is used herein to refer to data in any format, e.g., saved as one or more image files, etc., that is for one or more reference images, e.g., where the data can be used by an appropriate processor to produce one or more reference images. As such, a reference includes at least a first set of reference image data for a first reference image. In some instances a reference also includes a second set of reference image data for a second reference image. In such embodiments, a reference may include sets of reference image data for multiple reference images, e.g., 2 or more, 5 or more, 10 or more, 25 or more, 50 or more, 100 or more, 1000 or more, 1500 or more, 2000 or more, 5000 or more, 10,000 or more etc., reference images.

Reference images are predetermined images of a region of interest. As the reference images are predetermined, they are images that have been produced independently of the image data that is received by the image processing module. In some instances, the reference images are images that exist prior to obtainment of the image data that is received by the image processing module. The reference images may be images that are obtained from the same subject (e.g., person) that is being visualized during a given procedure (e.g., where the reference images were obtained from the subject prior to a given procedure) or from a different subject (e.g., person).

Alternatively, the reference images may be produced de novo, such that they are not produced from image data obtained from any actual subject but instead are designed, e.g., by using manual or computer assisted graphic protocols.

Reference images that make up the reference may differ from each other in a number of ways. For example, any two given reference images may be images of regions of interest of different internal tissue locations. In such a reference, the reference may include first and second pre-determined images that differ from each other with respect to a predetermined internal tissue location. For example, the reference may include images of at least a first tissue location and a second tissue location. The first and second tissue locations may be locations that a given device may be expected to image during a given procedure, such as during a surgical procedure. In some instances, the reference includes multiple images of different locations that a given visualization sensor should image during a given procedure if the procedure is performed correctly. The reference may also include images of different tissue locations that a visualization sensor should not see during a given procedure, e.g., images of tissue locations that should not be viewed by the sensor if the given procedure of interest is being performed correctly. Accordingly, some references may include multiple images that track the location of a device when correctly and incorrectly positioned during an entire procedure, such as an entire surgical procedure.

The sets of image data in the reference may include one or more color descriptor data and anatomical descriptor data. By color descriptor data is meant data which is based on the particular color of a given internal tissue site and components thereof. For example, an internal tissue site may include one or more tissues that each has a distinct color. For example, different tissues such as muscle, nerve, bone, etc., may have different colors. This distinct color may be present in the reference image as color descriptor data, and employed by the image processing module. By anatomical descriptor data is meant data which is based on the particular shape of one or more tissue structures at the internal tissue site. For example, different tissues such as muscle, nerve, bone, etc., have different shapes. These different shapes are present in the image data as anatomical descriptor data.

As summarized above, the image processing module compares received image data of an internal tissue site (e.g., obtained during a given procedure of interest) with the reference. The comparison performed by the image processing module may be achieved using any convenient data processing protocol. Data processing protocols that may be employed in this comparison step may compare the received image data and reference based on color descriptor data and/or anatomical descriptor data. Data comparison protocols of interest include, but are not limited to: mean absolute difference between the descriptors of data and stored values such as mean color intensity, and, the degree of correlation between principle axis of the structure and stored values.

In performing this comparison step, the image processing module may be configured to automatically select the appropriate images from a reference to compare against the received image data. In some instances, the image processing module is configured to compare the received image data with the reference by selecting an appropriate set of reference image data based on a determined positional location of the device. For example, the image processing module may obtain positional information about the device (e.g., as may be obtained from sensors on the device or manually input and associated with a given image) and then select reference images that are for the same positional location as the device when the device obtained the image data being received. Alternatively, the image processing module may automatically select appropriate sets of image data based on similarity parameters. For example, the image processing module may automatically select the most similar sets of image data from the reference to use in the comparison step.

The image processing module compares the received image data with the reference in order to determine whether an alert signal should be generated. In other words, the output of the image processing module is a decision as to whether an alert signal should be generated. If an image processing module determines that an alert signal should be generated, it may generate the alert signal or instruct a separate module of the system to produce an alert signal.

The alert signal, when generated, may vary depending on the nature of the system. An alert signal may be a warning signal about a given system parameter or a signal that confirms to an operator of the system that a given system parameter of interest is acceptable. In some embodiments, an alert signal may include functional information about a device. For example, in these embodiments an alert signal may include information that a given device is functioning properly, e.g., that a tissue modifier is not compromised in some manner, etc. For example, one problem that may occur during a surgical procedure is that a RF electrode breaks or is missing. The image processing module can automatically detect this occurrence and generate an alert signal that provides information to a user that the RF electrode as broken. In some embodiments, an alert signal may include positional information about a device. For example, an alert signal may include information as to whether or not a given device (or component thereof such as a tissue modifier) is correctly spatially positioned. In these embodiments, the alert signal may contain information that a tissue modifier of the device is contacting non-target tissue, such that the tissue modifier is not correctly spatially positioned.

The system may be configured to employ an alert signal in a variety of different ways. The system may be configured to provide the alert signal to a user of the system, e.g., via an alert signal output of the system. In addition or alternatively, the system may be configured to automatically modulate one or more operational parameters of the system based on the generation of an alert signal. For example, where the image processing module determines that a tissue modifier is contacting non-target tissue and therefore generates an alert signal, the alert signal may automatically modulate operation of the tissue modifier, e.g., by turning it off. In some instances, the alert signal may automatically shut the system down.

Figure 14:
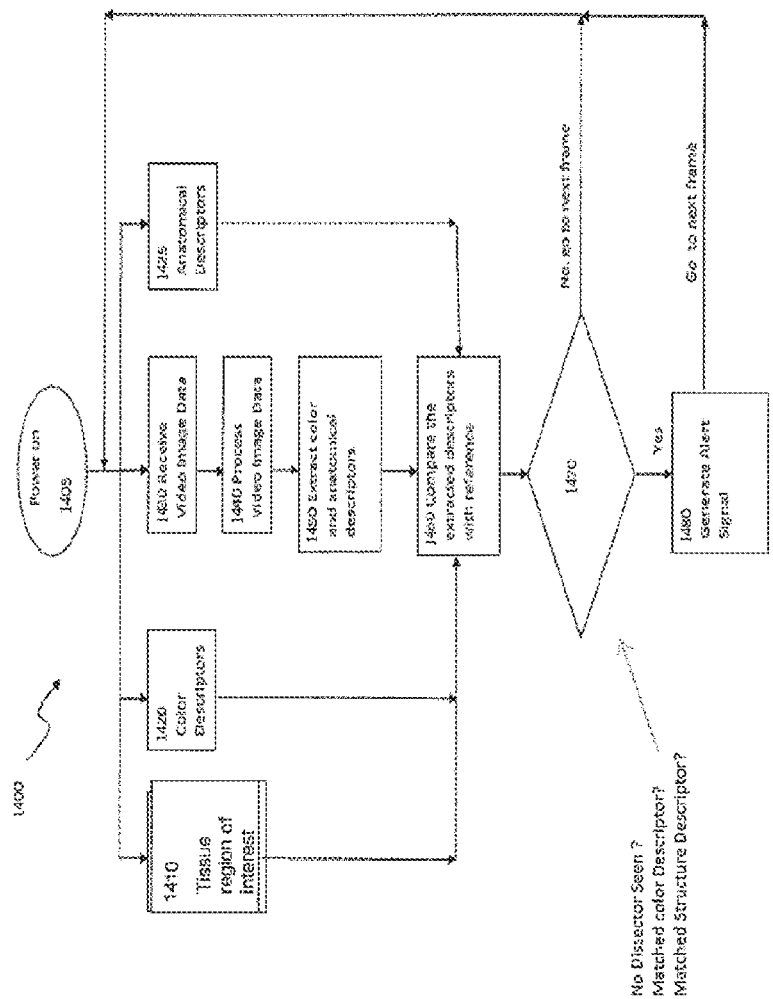
FIG. 14 provides a flow diagram of an image processing module, according to an embodiment.

The image processing module may be implemented as software, e.g., digital signal processing software; hardware, e.g., a circuit; or combinations thereof, as desired. FIG. 14 provides a flow diagram of an image processing module, according to an embodiment. In FIG. 14, the image processing module 1400 is powered on at 1405. Following power on at step 1405, the system loads the reference made up of sets of image data corresponding to regions of interest 1410, as well as color descriptors 1420 and anatomical descriptors 1425. Next, the system receives video image data at step 1430 and processes the received video image data at step 1440. For each given frame of the video, the image processing module 1400 extracts color and anatomical descriptors at step 1450 and uses these extracted descriptors to compare the received image data with the reference descriptors. At step 1470, the system decides whether or not to generate an alert signal. The system may decide whether or not to generate an alert signal based on a number of different alert signal thresholds. An alert signal threshold is a value for an image parameter, e.g., structural elements in the image (for example tissue modifiers), color descriptors, structure descriptors, etc. If the threshold is not exceeded (for example, the system finds the correct color or structures are present in the image), the image processing module may move on to the next frame of the video image data, as shown. Alternatively, if the threshold is exceeded, such that at least one of correct color and/or structure is not present in the image, the image processing module generates an alert signal at step 1480. The alert signal may include a number of different types of information, such as provide a simple warning to a user (such as surgeon) that something with the system and/or procedure is wrong, such as whether the tissue modifier is compromised, the tissue modifier is incorrectly positioned, etc. In these instances, the user may use the alert signal as an indication to halt or modify the procedure parameters. In some instances, the alert signal may automatically modify the operating parameters of the system in some manner, e.g., by automatically modifying the operating parameters of the tissue modifier, by turning the system off, etc.

Additional details regarding such image processing modules that are configured to compare to a reference are provided in U.S. application Ser. No. 12/437,186, the disclosure of which is herein incorporated by reference. It should be noted that while the image processing modules of these embodiments have been described in terms of their use with devices that include integrated distal end tissue modifiers, also encompassed within these particular embodiments of the invention are devices that do not include integrated distal end tissue modification, as the image processing module may be employed with a variety of different types of devices.

As reviewed above, in certain embodiments, a processor may be configured to produce a video from the image data that is obtained under white light, under near-infrared light or a combination of data taken under illumination of both kinds of light, i.e., to produce a multi-spectral or combined video. For example, if the target tissue site is relatively free of fluid, a user may desire to view the site under white light illumination. Alternatively, where the target tissue site is filled with fluid, a user may desire to view the site under near-infra-red illumination.

Figure 15:
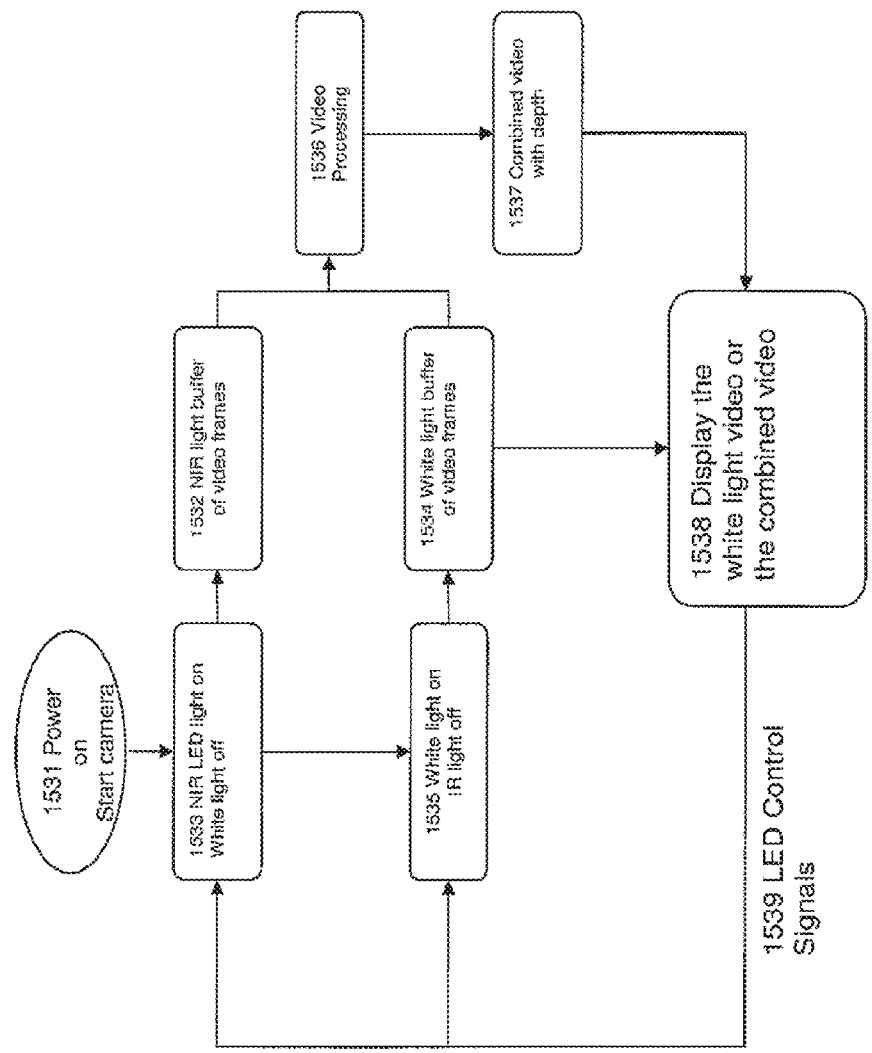
FIG. 15 provides for a schematic of the operational framework of a processor configured to produce video from image data obtained under white and/or near-infra-red light, according to an embodiment.

FIG. 15 provides for a schematic of the operational framework of a processor configured to produce video from image data obtained under white and/or near-infra-red light, according to an embodiment. As illustrated in FIG. 15, following power on 1531 of the camera, the camera obtains an NIR light buffer of video frames 1532 with the NIR LED on and the white light off 1533. In addition, the camera obtains a white light buffer of video frames 1534 with the NIR LED off and the white light on 1535. The resultant video data is processed at step 1536 to produce combined video with depth 1537. At step 1538, a user is given a choice of viewing a white light video obtained solely under white light illumination, or a combined video of a video obtained under white light illumination and a video obtained under near-infra-red illumination. By combined video is meant a video image that incorporates image data obtained under both white light illumination and near-infra-red illumination. Though not shown in FIG. 15, the processor may also be configured to provide a user with a choice of viewing only near-infra-red image data. User choice may be employed to control LEDs, as illustrated at step 1539.

Methods

Aspects of the subject invention also include methods of imaging and/or modifying an internal target tissue of a subject. Accordingly, aspects of the invention further include methods of imaging an internal tissue site with tissue modification devices of the invention. A variety of internal tissue sites can be imaged with devices of the invention. In certain embodiments, the methods are methods of imaging an intervertebral disc in a minimally invasive manner. For ease of description, the methods are now primarily described further in terms of imaging IVD target tissue sites. However, the invention is not so limited, as the devices may be used to image a variety of distinct target tissue sites.

With respect to imaging an intervertebral disc or portion thereof, e.g., exterior of the disc, nucleus pulposus, etc., embodiments of such methods include positioning a distal end of a minimally invasive intervertebral disc imaging device of the invention in viewing relationship to an intervertebral disc or portion of there, e.g., nucleus pulposus, internal site of nucleus pulposus, etc. By viewing relationship is meant that the distal end is positioned within 40 mm, such as within 10 mm, including within 5 mm of the target tissue site of interest.

Methods of invention may include obtaining image data of an internal tissue site with a visualization sensor and then forwarding the image data to an image processing module of a system of the invention. Methods of invention may also include receiving image data into a system that includes an image processing module of the invention. The methods may further include viewing an image produced from the image data received by the image processing module.

Positioning the distal end in viewing device in relation to the desired target tissue may be accomplished using any convenient approach, including through use of an access device, such as a cannula or retractor tube, which may or may not be fitted with a trocar, as desired. Following positioning of the distal end of the imaging device in viewing relationship to the target tissue, the target tissue, e.g., intervertebral disc or portion thereof, is imaged through use of the illumination and visualization elements to obtain image data. Image data obtained according to the methods of the invention is output to a user in the form of an image, e.g., using a monitor or other convenient medium as a display means. In certain embodiments, the image is a still image, while in other embodiments the image may be a video.

In certain embodiments, the methods include a step of tissue modification in addition to the tissue viewing. For example, the methods may include a step of tissue removal, e.g., using a combination of tissue cutting and irrigation or flushing. For example, the methods may include cutting a least a portion of the tissue and then removing the cut tissue from the site, e.g., by flushing at least a portion of the imaged tissue location using a fluid introduced by an irrigation lumen and removed by an aspiration lumen.

The internal target tissue site may vary widely. Internal target tissue sites of interest include, but are not limited to, cardiac locations, vascular locations, orthopedic joints, central nervous system locations, etc. In certain cases, the internal target tissue site comprises spinal tissue.

The subject methods are suitable for use with a variety of mammals. Mammals of interest include, but are not limited to: race animals, e.g. horses, dogs, etc., work animals, e.g. horses, oxen etc., and humans. In some embodiments, the mammals on which the subject methods are practiced are humans.

An example of a method which employs the device depicted in FIG. 3A includes the following steps. First the distal end 300 of the device is introduced into the target tissue dissection region through access device 310. Access device 310 may be any convenient device, such as a conventional retractor tube. Access device 310 as shown in FIG. 3A has an inner diameter of 7.0 mm and an outer diameter of 9.5 mm. At this stage, orientation of camera 320 is biased to one side (left side in figure). During insertion, the electrode 340 on the side opposite the viewing field of the camera (right side in figure) is distally translated so that it emerges distally from the distal tip of the device 300. Also during insertion, the distally translated electrode 340 is activated by supplying RF current and irrigating conducting fluid, resulting in tissue dissection during insertion of the device. For further tissue dissection on the side to which the camera is biased (left side in figure), the electrode 340 on the same side as the viewing field of the camera (left side in figure) is distally translated so that it emerges laterally from the endoscope probe on the proximal side of the camera. While being translated, the same electrode (left side in figure) is activated by supplying RF current and irrigating conducting fluid, resulting in tissue dissection. At this point, the entire end of the device 300 may be translated proximally and distally until the desired tissue dissection is obtained. When finished with tissue dissection at the first location, the device may be rotated 180 degrees and further tissue removed using the steps described above.

Utility

The subject tissue modification devices and methods find use in a variety of different applications where it is desirable to image and/or modify an internal target tissue of a subject while minimizing damage to the surrounding tissue. The subject devices and methods find use in many applications, such as but not limited to surgical procedures, where a variety of different types of tissues may be removed, including but not limited to: soft tissue, cartilage, bone, ligament, etc. Specific procedures of interest include, but are not limited to, spinal fusion (such as Transforaminal Lumbar Interbody Fusion (TI-IF)), total disc replacement (TDR), partial disc replacement (PDR), procedures in which all or part of the nucleus pulposus is removed from the intervertebral disc (IVD) space, arthroplasty, and the like. As such, methods of the invention also include treatment methods, e.g., where a disc is modified in some manner to treat an existing medical condition. Treatment methods of interest include, but are not limited to: annulotomy, nucleotomy, discectomy, annulus replacement, nucleus replacement, and decompression due to a bulging or extruded disc. Additional methods in which the imaging devices find use include those described in United States Published Application No. 20080255563.

In certain embodiments, the subject devices and methods facilitate the dissection of the nucleus pulposus while minimizing thermal damage to the surrounding tissue. In addition, the subject devices and methods can facilitate the surgeon's accessibility to the entire region interior to the outer shell, or annulus, of the IVD, while minimizing the risk of cutting or otherwise causing damage to the annulus or other adjacent structures (such as nerve roots) in the process of dissecting and removing the nucleus pulposus.

Furthermore, the subject devices and methods may find use in other procedures, such as but not limited to ablation procedures, including high-intensity focused ultrasound (HIFU) surgical ablation, cardiac tissue ablation, neoplastic tissue ablation (e.g. carcinoma tissue ablation, sarcoma tissue ablation, etc.), microwave ablation procedures, and the like. Yet additional applications of interest include, but are not limited to: orthopedic applications, e.g., fracture repair, bone remodeling, etc., sports medicine applications, e.g., ligament repair, cartilage removal, etc., neurosurgical applications, and the like.

Devices of the invention may provide variable tactile feedback to the operator depending on tissue type. For example, in embodiments where a distal end structure, such as a tissue modifier (e.g., a RF electrode) is linearly translated by a mechanical linear actuator (e.g., as described above), the operator may experience different tactile properties depending on the type of tissue that is being contacted by the linearly translating distal end structure. These different tactile properties may then be employed by the user to differentiate between different types of tissue. In other words, devices of invention may provide different sensations to an operator, such as a surgeon, during use depending on the nature of the tissue with the distal end of the device is in contact. As such, devices and methods of the invention also find use in tissue discrimination applications, where the devices are employed to determine the particular nature of the internal tissue with which the distal end of the device is in contact, e.g., whether the distal end of the device is in contact with soft tissue, cartilage, bone, etc.

As reviewed above, in some embodiments synchronization of the tissue modifier's modulation waveform with its linear translation waveform provides additional benefits. For instance, rapid retraction of the electrode from hard tissue that it encounters will leave the tissue modifier physically separated from the hard tissue by a gap as the tissue modifier approaches the proximal extreme position. In some embodiments, the tissue modifier tip is activated only when the tissue modifier is at or near the proximal extreme position, as mentioned above. This has the effect of preferentially delivering the tissue modification energy to soft, compliant tissue as opposed to hard, stiff tissue. Stated otherwise, this provides tissue discrimination based on elastic modulus. In the case of spinal surgery applications requiring removal of nuclear material, such as fusion, total disc replacement, and partial disc replacement, synchronization of the modulation waveform with the linear translation waveform facilitates the delivery of tissue modification energy to the nucleus pulposus (soft, compliant tissue) while minimizing the delivery of tissue modification energy to the disc annulus (hard, stiff tissue) and the endplates of the vertebral bodies (hard, stiff tissue). In addition, cyclic linear translation of the tissue modifier helps to prevent a condition where the electrode sticks to tissue as it ablates it, resulting in increased thermal effects to the surrounding tissue, ineffective or discontinuous tissue dissection, buildup of charred or otherwise modified tissue on the tissue modifier tip, or a combination thereof. Additionally, cyclic linear translation of the tissue modifier helps chop the dissected tissue into smaller pieces, thus facilitating aspiration of the dissected tissue.

Kits

Also provided are kits for use in practicing the subject methods, where the kits may include one or more of the above devices, and/or components of the subject systems, as described above. The kit may further include other components, e.g., guidewires, access devices, fluid sources, etc., which may find use in practicing the subject methods. Various components may be packaged as desired, e.g., together or separately.

In addition to above mentioned components, the subject kits may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention Therefore, is not intended to be limited to the exemplary embodiments shown and described herein. Rather, the scope and spirit of present invention is embodied by the appended claims.

What is claimed is:

1. A tissue modification device, comprising:
   a rigid elongated member comprising a proximal end and a distal end, the distal end dimensioned to be passed through a minimally invasive body opening;
   a radiofrequency electrode positioned on the rigid elongated member, the radiofrequency electrode configured to deliver radiofrequency energy to a tissue, the radiofrequency energy comprising a frequency;
   a mechanical actuator, the mechanical actuator configured to extend the radiofrequency electrode beyond the distal end of the rigid elongated member at a linear translation frequency; and
   a controller configured to synchronize the linear translation frequency to operate in a coordinated manner with the radiofrequency energy frequency such that the radiofrequency electrode is configured to deliver radiofrequency energy only while at a position other than when the radiofrequency electrode is at a fully extend oscillation position.

2. The device of claim 1, wherein the linear translation frequency is configured such that the device provides variable tactile feedback to an operator depending upon a type of tissue in contact with the radiofrequency electrode.

3. The device of claim 1, wherein the radiofrequency electrode is configured to stop delivery of radiofrequency energy when the radiofrequency electrode reaches the fully extend oscillation position.

4. The device of claim 3, wherein the linear translation frequency is configured such that radiofrequency energy is preferentially delivered to soft tissue.

5. The device of claim 1, wherein the electrode is configured to deflect at an angle from a longitudinal axis passing through the elongated member.

6. The device of claim 1, wherein the electrode is configured to translate in both a distal direction away from the center of the elongated member and a proximal direction toward the center of the elongated member.

7. The device of claim 1, wherein the mechanical actuator is selected from the group of a voice coil motor, a solenoid, and a pneumatic actuator.

8. The device of claim 1, wherein the linear translation frequency is 50 Hz or greater.

9. The device of claim 1, wherein the radiofrequency energy frequency is equal to the linear translation frequency.

10. The device of claim 1, wherein the radiofrequency energy further comprises a waveform, the waveform phase-shifted relative to a linear translation waveform of the linear actuator.

11. The device of claim 1, further comprising a sensor positioned at the distal end of the elongated member, the sensor configured to collect data on the linear translation of the radiofrequency electrode.

12. The device of claim 11, wherein the sensor comprises an accelerometer.

13. The device of claim 11, wherein the sensor comprises an optical encoder.

14. The device of claim 1, wherein the radiofrequency electrode is circular.

15. The device of claim 1, further comprising a visualization sensor positioned at the distal end of the elongated member.

16. The device of claim 1, further comprising a physiological sensor configured to collect physiological data.

17. The device of claim 16, wherein a controller is configured to transmit the physiological data to an image display component, wherein the image display component is configured to provide the physiological data to a user.

18. The device of claim 1, wherein the device further comprises an integrated articulation mechanism that imparts steerability to the distal end of the elongated member.

19. The device of claim 18, wherein the distal end of the elongated member is rotatable about its longitudinal axis.

* * * * *

UNITED STATES PATENT AND TRADEMARK OFFICE
CERTIFICATE OF CORRECTION

Page 1 of 1

PATENT NO.         : 12,035,889 B2
APPLICATION NO.    : 16/000731
DATED              : July 16, 2024
INVENTOR(S)        : James S. Cybulski et al.

It is certified that error appears in the above-identified patent and that said Letters Patent is hereby corrected as shown below:

In the Claims

On Column 40, Line 3: In Claim 1, delete "extend" and insert -- extended --.

On Column 40, Line 11 (Approx.): In Claim 3, delete "extend" and insert -- extended --.

Signed and Sealed this
Eighth Day of October, 2024

Katherine Kelly Vidal
*Director of the United States Patent and Trademark Office*